(12) United States Patent
Randolph et al.

(10) Patent No.: US 6,613,358 B2
(45) Date of Patent: Sep. 2, 2003

(54) SUSTAINED-RELEASE COMPOSITION INCLUDING AMORPHOUS POLYMER

(76) Inventors: Theodore W. Randolph, 7916 Sussex Ct., Niwot, CO (US) 80503; Mark C. Manning, 1112 Live Oak Ct., Fort Collins, CO (US) 80525; Richard F. Falk, 1266 NW. Knoxville, Apt. D., Bend, OR (US) 97701

( * ) Notice: Subject to any disclaimer, the term of this patent is extended or adjusted under 35 U.S.C. 154(b) by 55 days.

(21) Appl. No.: 09/877,330

(22) Filed: Jun. 7, 2001

(65) Prior Publication Data

US 2002/0132007 A1 Sep. 19, 2002

Related U.S. Application Data

(63) Continuation of application No. 09/403,412, filed as application No. PCT/US99/06198 on Mar. 18, 1999, now abandoned.
(60) Provisional application No. 60/166,230, filed on Nov. 18, 1999, and provisional application No. 60/078,390, filed on Mar. 18, 1998.

(51) Int. Cl.$^7$ .............................. A61K 9/16; A61F 2/00
(52) U.S. Cl. ...................... 424/489; 424/423; 424/426; 424/427; 424/434; 424/435; 514/772.3; 514/781; 514/937; 514/951
(58) Field of Search ................................ 424/423, 426, 424/427, 428, 434, 435, 464, 489

(56) References Cited

U.S. PATENT DOCUMENTS

| | | | |
|---|---|---|---|
| 3,941,763 A | 3/1976 | Sarantakis | 260/112.5 |
| 4,308,280 A | 12/1981 | Sportoletti et al. | 424/311 |
| 4,526,938 A | 7/1985 | Churchill et al. | 525/415 |
| 4,582,820 A | 4/1986 | Teng | 514/3 |
| 4,873,187 A | 10/1989 | Taub | 435/5 |
| 5,010,183 A | 4/1991 | Macfarlane | 536/27 |
| 5,043,280 A | 8/1991 | Fischer et al. | 435/235.1 |
| 5,364,884 A | 11/1994 | Varma et al. | 514/551 |
| 5,445,832 A | 8/1995 | Orsolini et al. | 424/491 |
| 5,770,559 A | 6/1998 | Manning et al. | 514/2 |

FOREIGN PATENT DOCUMENTS

WO      94/08599      4/1994

OTHER PUBLICATIONS

Ahern et al., "Control of oligomeric enzyme thermostability by protein engineering," *Proc. Natl. Acad. Sci USA* 84: 675–679 (1987).
Arakawa and Timasheff, "Preferential Interactions of Proteins with Salts in Concentrated Solutions," *Biochemistry* 21: 6545–6552 (1982).
Arakawa and Timasheff, "Stabilization of Protein Structure by Sugars," *Biochemistry* 21: 6536–6544 (1982).
Baker et al., "The Structure of 2Zn Pig Insulin Crystals at 1.5 Å Resolution," *Phil. Trans. R. Soc. London* B319: 369–456 (1989).
Brems et al., "Equilibrium Denaturation of Insulin and Proinsulin," *Biochemistry* 29: 9289–9293 (1990).
Casal et al., "Subunit Interface of Triosephosphate Isomerase: Site–Directed Mutagenesis and Characterization of the Altered Enzyme," *Biochemistry* 26: 1258–1264 (1987).
Cory et al., "Use of an Aqueous Soluble Tetrazolium/Formazan Assay for Cell Growth Assays in Culture," *Cancer Commun.*, 3: 207–2112 (1991).
Davis et al., "Preparation and Characterization of Antibodies with Specificity for the Amino–Terminal Tetrapeptide Sequence of the Platelet–Derived Connective Tissue Activating Peptide–III," *Biochem. Intl.*, 10: 394–414 (1985).
Erikson et al., "Solid–Phase Peptide Synthesis," in *The Proteins*, 3rd ed., vol. 2, Neurath et al. (eds.), pp. 257–527 (1976).
Ettinger and Timasheff, "Optical Activity of Insulin. I. On the Nature of the Circular Dichroism Bands," 10: 824–83 (1971).
Finn et al., "The Synthesis of Peptides by Solution Methods and Emphasis on Peptide Hormones," in *The Proteins*, 3rd ed., vol. 2, Neurath et al. (eds.), pp. 105–253, Academic Press, New York (1976).
Fraser et al., "Topoisomerase IIα Promoter Trans–Activation Early in Monocytic Differentiation of HL–60 Human Leukemia Cells," *Mol. Pharmacol.* 47:696–706 (1995).
Johnson, "Protein Secondary Structure and Circular Dichroism: A Practical Guide," *Genetics* 7: 205–214 (1990).
Miyajima et al., "Effect of polymer crystallinity on papaverine release from poly (1–lactic acid) matrix," *J. Controlled Release* 49: 207–215 (1997).
Melberg and Johnson, "Changes in Secondary Structure Follow with Dissociation of Human Insulin Hexamers: A Circular Dichroism Study," *Genetics* 8: 280–286 (1990).
Merrifield, "Solid–Phase Peptide Synthesis," in *Chem. Polypeptides*, Katsoyannis and Panayotis (eds.), pp. 335–361 (1973).
Merrifield, "Solid Phase Peptide Synthesis. I. The Synthesis of a Tetrapeptide," *J. Am. Chem. Soc.*, 85: 2149–2154 (1963).
Mitsunobu, "The Use of Diethyl Azodicarboxylate and Triphenylphosphine in Synthesis and Transformation of Natural Products," *Synthesis*, pp. 1–28 (1981).
Pocker and Biswas, "Conformational Dynamic of Insulin in Solution. Circular Dichroic Studies," *Biochemistry* 19: 5043–5049 (1980).

(List continued on next page.)

*Primary Examiner*—James M. Spear
(74) *Attorney, Agent, or Firm*—Medlen & Carroll LLP

(57) ABSTRACT

Provided is a sustained release composition for sustained release of a pharmaceutical substance. The composition includes a biocompatible polymer that is highly amorphous and a pharmaceutical substance in a hydrophobic ion complex with an amphiphilic material. Also provided is a compressed antisolvent method for manufacturing the composition, various product forms incorporating the composition and various uses for the composition.

48 Claims, 35 Drawing Sheets

OTHER PUBLICATIONS

Sambrook et al., *Molecular Cloning: A Laboratory Manual*, Cold Spring Harbor Laboratory, (1989).

Stewart and Young, *Solid Phase Peptide Synthesis*, Freeman and Company, San Francisco (1969) (Title and Copyright Pages Only).

van Stokkum et al., "Estimation of Protein Secondary Structure and Error Analysis from Circular Dichroism Spectra," *Anal. Biochem.*, 191:110–118 (1990).

Weitzel et al., "Insulinähnliche Aktivität von Arginylverbindungen in vitro," *Hoppe Seylers Z. Physiol. Chem.*, 352:1617–1630 (1971).

Wlodawer et al., "Structure of Bovine Pancreatic Trypsin Inhibitor. Results of Joint Neutron and X–ray Refinement of Crystal Form II," *J. Mol. Biol.*, 180: 301–329 (1984).

Wlodawer et al., "Comparison of Two Highly Refined Structures of Bovine Pancreatic Trypsin Inhibitor," *J. Mol. Biol.*, 193:145–156 (1987).

Stratton et al., "Drug Delivery Matrix Containing Native protein Precipitates Suspended in a Poloxamer Gel," *J. Pharm. Sci.*, 86: 1006–1010 (1997).

Falk et al., "Controlled release of ionic compounds from poly (L–lactide) microspheres produced by precipitation with a compressed antisolvent," *J. Controlled Release* 44:77–85 (1997).

Matsuura et al., "Structure and Stability of Insulin Dissolved in 1–Octanol," *J. Am. Chem. Soc.*, 115: 1261–1264 (1993).

Meyer et al., "Generation of soluble and active subtilisin and α–chymotrypsin in organic solvents via hydrophobic ion pairing," *Int. J. Peptide Prot. Res.*, 47: 177–181 (1996).

Meyer et al., "Solution Behavior of α–Chymotrypsin Dissolved in Nonpolar Organic Solvents Via Hydrophobic Ion Pairing," *Biopolymers* 35: 451–456 (1995).

Meyer et al., "Selective Precipitation of Interleukin–4 Using Hydrophobic Ion Pairing: A Method for Improved Analysis of Proteins Formulated with Large Excesses of Human Serum Albumin," *Pharm. Res.*, 11: 1492–1495 (1994).

Powers et al., "Enhanced Solubility of Proteins and Peptides in Nonpolar Solvents Through Hydrophobic Ion Pairing," *Biopolymers* 33: 927–932 (1993).

Randolph et al., "Sub–micrometer–sized biodegradable particles of poly (L–lactic acid) via the gas antisolvent spray precipitation process," *Biotechnol. Prog.*, 9: 429–435 (1993).

Nielsen, *Mechanical Properties of Polymers*, (New York: Reinhold Publishing Corporation) pp. 235–236 (1962).

ARGININE ESTER SYNTHESIS -- GENERAL ROUTE (L)-arginine (free base)     thionyl chloride (L)-arginine acid chloride + hydrochloric acid + sulfur dioxide (L)-arginine acid chloride     alcohol (L)-arginine-ester hydrochloride Vilsmeier route dimethylformamide + thionyl chloride  ROH solvent ⟶ dimethylchloroforminium chloride + (L)-arginine free base (L)-arginine acid chloride + dimethylformamide + HCl

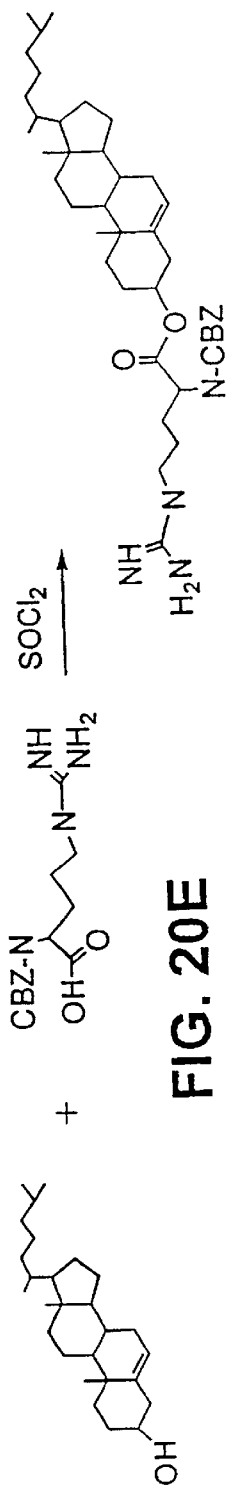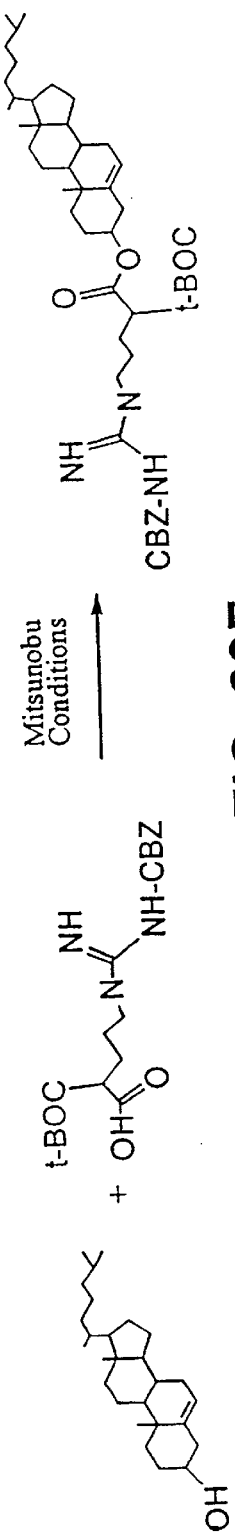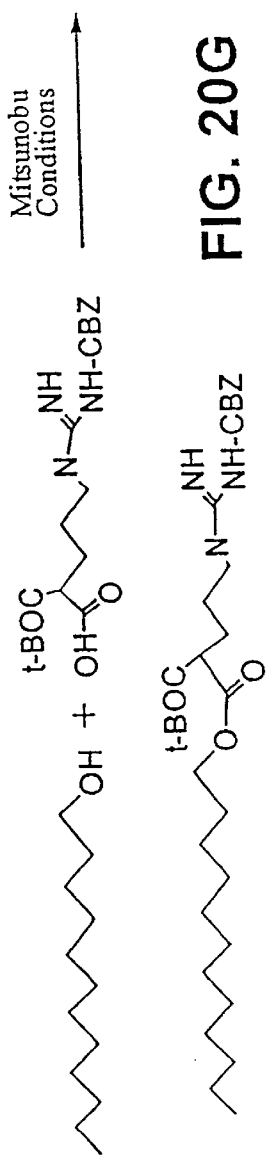
FIG. 20E
FIG. 20F
FIG. 20G

CONTINUE AS IN FIGURE 21E

SUSTAINED-RELEASE COMPOSITION INCLUDING AMORPHOUS POLYMER

The present application is a Continuation of U.S. patent application Ser. No. 09/403,412, filed on Mar. 8, 2000 now abandoned which is a 371 of PCT/US99/06198 filed Mar. 18, 1999 which claims benefit of No. 60/166,230 filed Nov. 18, 1999 and claims benefit of No. 60/078,390 filed Mar. 18, 1998.

FIELD OF THE INVENTION

The present invention concerns a highly amorphous sustained-release composition for sustained release of a pharmaceutical substance; an antisolvent precipitation method for making the composition: products made using the composition: and uses of the composition.

BACKGROUND OF THE INVENTION

Pharmaceutical substances may be introduced into a human or animal host for therapeutic or curative purposes in a number of ways. In many pharmaceutical applications, the pharmaceutical substance is administered in the form of solid particles. For example, a micropump may be used in some applications for prolonged treatment by slowly injecting a suspension of small particles in a liquid. Also, small particles having both a pharmaceutical substance and a biodegradable polymer may be placed within issue for sustained release of the pharmaceutical substance, with the biodegradable polymer acting to control the release of the pharmaceutical substance. Furthermore, in pulmonary delivery applications, small particles may be inhaled to lodge in tissue of the lungs, permitting the pharmaceutical substance to then enter the circulatory system or to be released for local treatment Often, however, problems are encountered in attempting to make particles having the desired properties for a particular pharmaceutical application. For example, when particles having a biodegradable polymer and a pharmaceutical substance are prepared, the pharmaceutical substance often concentrates near the surface of the particles. This effect may cause a sudden, undesirable release of the pharmaceutical substance when it is initially introduced into the host. Also, when using a micropump for continuous injection of a suspension over a prolonged period, the solid particles tend to settle over time, which may cause an undesirable variation in the rate of delivery of the pharmaceutical substance.

With respect to pulmonary delivery applications, current methods for delivering the pharmaceutical substance in small particles typically result in a majority of the pharmaceutical substance being wasted. In one method, called nebulization, a liquid having the pharmaceutical substance in solution is sprayed at a high velocity and inhaled. Alternatively, nebulization may involve spraying a powder as fine particles propelled by a carrier gas, with the particles being inhaled. Particles administered by both these nebulization methods. However, may have a wide distributor of droplet or particle sizes, resulting in a very low utilization of the pharmaceutical substance. Particles, or droplets, which are too large tend to lodge in the throat and mouth during inhalation and are not, therefore, effective for delivering the pharmaceutical substance to the lungs. Particles, or droplets, which are too small tend not to impact on the lung tissue, but rather tend to be exhaled. As much as 80 to 90 percent or more, of the pharmaceutical substance may, therefore, be wasted and only a small portion of the pharmaceutical substance which is administered may actually reach the desired target in the lung.

Many of these problems with delivery of particles of a pharmaceutical substance result from limitations on methods used to make the particles. One method for making particles of a pharmaceutical substance, called lyophilization, involves rapid freezing of the pharmaceutical substance with water, followed by rapid dehydration of the frozen material to produce dry particles of the pharmaceutical substance. This technique has been used with proteins and other polypeptides, but the low temperatures involved may reduce the biological activity of some polypeptide molecules. Also, the particles produced by lyophilization tend to be large and clumping and are often not suitable for pharmaceutical delivery methods which require smaller particles. It is possible to grind the lyophilized particles to produce smaller particles, but such grinding may damage some pharmaceutical substances, especially proteins. Also, even when a substance may be ground without significant damage to the activity of the substance, it is difficult to obtain a pharmaceutical powder having particles of a narrow size distribution. Therefore, such pharmaceutical powders are prone to substantial waste of the pharmaceutical substance, such as described above for pulmonary delivery applications.

One method which has been proposed for making small particles of a pharmaceutical substance is called gas antisolvent precipitation. In this method, a pharmaceutical substance is dissolved in an organic solvent which is then sprayed into an antisolvent fluid, such as carbon dioxide, under supercritical conditions. The antisolvent fluid rapidly invades spray droplets, causing precipitation of very small pharmaceutical particles.

The gas antisolvent precipitation technique, however, requires that the pharmaceutical substance be soluble in the organic solvent. For hydrophobic pharmaceutical substances, this generally presents no problem because those substances can readily be dissolved in relatively mild, nonpolar organic solvents. Hydrophilic pharmaceutical substances, however, are substantially insoluble in such relatively mild organic solvents.

It has been proposed that insulin, a hydrophilic protein, may be processed in a gas antisolvent precipitation process by dissolving the insulin in dimethylsulfoxide (DMSO) or N,N-dimethylformamide (DMF), both of which are strong, highly polar solvents. One problem with such a process, however, is that highly polar solvents such as DMSO and DMF tend to unfold protein molecules from their native tertiary structure, or conformation. These protein molecules would, therefore, also be precipitated in an unfolded state for incorporation into the solid particles. Such unfolding could seriously reduce the biological activity of a protein or other polypeptide, especially if stored as a solid particle in the unfolded state for any appreciable time.

There is a need for improved methods for making solid particles of pharmaceutical substances, and especially for making particles of hydrophilic substances, to permit preparation of particles having an appropriate size and size distribution without the molecular unfolding associated with the gas antisolvent precipitation method and without the low temperatures and grinding associated with lyophilization.

Despite intense efforts in the field of gene therapy, there is still a lack of well-defined delivery vehicles that will allow efficient and effective delivery of an oligonucleatide-based therapeutic agent. Much of the work in this area has centered on the use of cationic lipids. The ability of cationic lipids to interact with membranes, to increase the lipophilicity of polynucleotides, and to mask the significant negative charge on polynucleotides, appears to be essential to achieving a high degree of transfection of the targeted cell. However, there remains a need in the art for more effective ways of achieving transfections It has been reported that cationic surfactants can be used to conjugate nucleic acids to enzymes and to purify nucleic acids. See U.S. Pat. Nos. 4,873,187 and 5,010,183. In particular, the latter patent teaches that the cationic surfactants and nucleic acids form hydrophobic complexes that can be dissolved or dispersed in polar solvents for purification of the nucleic acids.

However, currently existing cationic surfactants tend to be toxic and not suitable for pharmaceutical use or other uses where cell survival is important. Therefore, a need exists for new cationic surfactants that are less toxic than the existing cationic surfactants and which can be used in situations where cell survival is important.

Furthermore, the morphology of the particles may detrimentally effect performance. For example, M. Mayajim et al, Effect of Polymer Crystallinity on Paperverine Release from Poly(l-lactic acid) Matrix, describe a problem encountered with amorphous poly(l-lactic acid) in sustained-release compositions. The amorphous polymer had an undesirable tendency to crystallize during drug release, thereby altering the drug release characteristics of the composition.

There is a need for improved methods for making compositions for sustained-release applications and for improved sustained release-compositions with desirable drug release characteristics.

SUMMARY OF THE INVENTION

According to the present invention, a method is provided for placing a pharmaceutical substance into solution in an organic solvent in the form of a hydrophobic ion pair complex with an amphiphilic material. The resulting solution may then be subjected to gas antisolvent precipitation using a near critical or supercritical fluid to produce a precipitate of particles comprising the pharmaceutical substance. Particles may be produced with a relatively narrow size distribution in a variety of sizes, thereby permitting flexibility in preparing particles for effective utilization in a variety of pharmaceutical applications.

The present invention, therefore, permits pharmaceutical substances which are ordinarily substantially not soluble in an organic solvent to be solubilized, which facilitates further processing to prepare pharmaceutical powders. The method is particularly preferred for use with proteins and other polypeptide molecules. Those molecules may be dissolved in a relatively mild, relatively non-polar organic solvent thereby decreasing the potential for the reduction in biological activity which could result from use of a strong, lightly polar organic solvent in which the hydrophilic molecules are directly soluble.

In one embodiment of the present invention, a biodegradable polymer may be co-dissolved in the organic solvent along with the pharmaceutical substance and the amphiphilic material. When processed by gas antisolvent precipitation, the particles produced comprise an intimate mixture of the biodegradable polymer with the pharmaceutical substance and the amphiphilic material. Problems of compositional variation or concentration of the pharmaceutical substance near the surface of the particle are, therefore, reduced relative to processes which require processing of a pharmaceutical substance in a suspension.

In one embodiment, through careful control of the antisolvent precipitation process operating conditions, a highly amorphous sustained-release composition may be made including a biocompatible polymer, typically also biodegradable, and a pharmaceutical substance in the form of a hydrophobic ion pair complex with an amphiphilic material. The polymer is highly amorphous, preferably with no greater than about 25% crystallinity and more preferably with an even lower crystallinity. Furthermore, the composition typically includes a very high loading of the pharmaceutical substance and the amphiphilic material, which together in the hydrophobic ion pair complex typically comprise greater than about 15 weight percent of the composition, and preferably even more. The composition exhibits desirable release characteristics for sustained release of the pharmaceutical substance and does not appear to have a problem with crystallization of the polymer during drug release, as has been reported by others. Also, the amorphous character of the polymer should be less likely to provoke an immune response that could cause inflammation. Moreover, the composition typically includes low or insignificant levels of residual solvent from the manufacture process. The composition may be incorporated into a variety of product forms for administration to a mammalian patient. Preferred methods for use of the composition include inhalation for pulmonary delivery, subcutaneous placement, intraperitoneal placement and intraocular placement To make the highly amorphous sustained-release composition, the antisolvent precipitation process is controlled to provide the desired characteristics in the composition. A high ratio of volumetric flow of antisolvent fluid to volumetric flow of liquid feed (in which the pharmaceutical substance amphiphilic material and polymer are codissolved) is is preferred, with a ratio of from about 20 to about 30 being particularly preferred. Lower flow ratios tend to increase crystallinity of the polymer in the composition. Also, it has been found that it is preferred to process the antisolvent and the liquid feed in concurrent flow to enhance the quality of the composition. Furthermore, the preferred method of operation of the process is to contact the liquid feed and antisolvent fluid at subcritical conditions, but preferably at a reduced temperature of greater than about 0.5.

In another embodiment of the present invention, a pharmaceutical substance is provided having particles comprising a pharmaceutical substance and an amphiphilic material in a hydrophobic ion pair complex. In one embodiment the articles have a narrow size distribution, with greater than about 90 weight percent of the particles having a size smaller than about 10 microns. In another embodiment, the solid particles are hollow and have a substantially elongated, fiber-like shape. These elongated particles are advantageous in that they should have a longer retention time, compared to substantially spheroidal particles in the stomach of a human or animal host following ingestion. Therefore, the particles may be advantageously used for sustained release applications for delivery of a pharmaceutical substance in the stomach region.

In yet a further embodiment of the present invention, a method is provided for delivering a pharmaceutical substance for treatment of a human or animal host in which a pharmaceutical formulation is administered having solid particles including a pharmaceutical substance and an amphiphilic material. The admin on may be by inhalation of the solid particles, by injection of a suspension of the solid particles in a liquid medium or by ingestion of the solid particles.

The invention also provides cationic surfactants having the formula:

P-L-C wherein:
P is a biocompatible hydrophobic moiety;
C is a biocompatible cationic moiety; and
L is a biodegradable linkage linking P and C.

These cationic surfactants are substantially less toxic than currently existing cationic surfactants and can be used for administration of pharmaceutical substances to animals and in other situations where cell survival is important. In particular, they can be used as the amphiphilic material in the methods and compositions described above. In addition, these cationic surfactants can be used to deliver nucleic acids into cells, making them useful in genetic engineering techniques, including gene therapy.

BRIEF DESCRIPTION OF THE DRAWINGS

FIGS. 20A–G illustrate schemes for the synthesis of arginine esters. CBZ is phenylmethoxycarbonyl and tBOC is t-butyloxycarbonyl.

DETAILED DESCRIPTION OF THE PRESENTLY PREFERRED EMBODIMENTS

Figure 1:
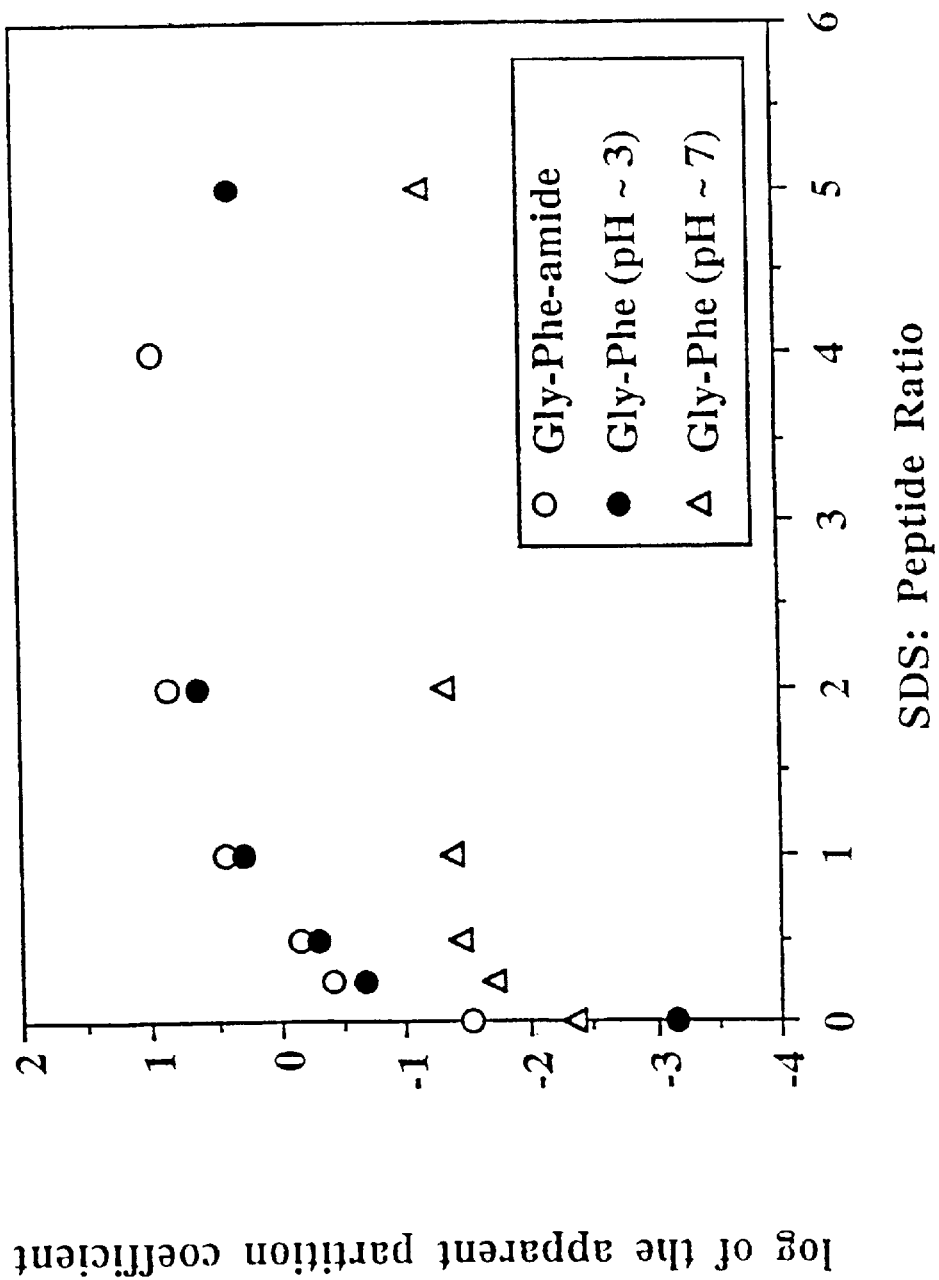
FIG. 1 shows the log of the apparent partition coefficient for the dipeptide Gly-Phe-NH$_2$.

In one aspect the present invention permits a pharmaceutical substance to be solubilized in an organic solvent by associating the pharmaceutical substance with an amphiphilic material. The pharmaceutical substance is substantially not directly soluble in the organic solvent, but becomes soluble in association with the amphiphilic material. It should be appreciated that by substantially not soluble it is not meant that the pharmaceutical substance is utterly insoluble in an organic solvent. Rather, it is meant that the direct solubility of the pharmaceutical substance in the organic solvent is limited and that it would be desirable to dissolve an amount of the pharmaceutical substance over and above that amount which is directly soluble. That desired additional amount is not soluble in the organic solvent. This is often the case for a pharmaceutical substance which is only slightly soluble in an organic solvent, when it mad be desirable to dissolve more of the pharmaceutical substance into the organic solvent than is possible by direct dissolution. According to the present invention, when the pharmaceutical substance is combined with the amphiphilic material, the solubility of the pharmaceutical substance in the organic solvent may be increased by an order of magnitude or more, and is often increased by more than two orders of magnitude relative to direct dissolution of the pharmaceutical substance into the organic solvent, in the absence of the amphiphilic material.

With the present invention, the pharmaceutical substance and the amphiphilic material are in a true, homogeneous solution in the organic solvent. By a true, homogeneous solution, it is meant that the pharmaceutical substance, the amphiphilic material and the organic solvent form a single liquid phase. The present invention is, therefore, distinguishable from the preparation of emulsions, micellar systems and other colloidal suspensions which comprise at least two distinct phases, with one phase being dispersed within the other phase.

To assist in the understanding of the present invention, but not to be bound by theory, it is believed that the pharmaceutical substance and the amphiphilic material are associated in the form of a complex between the amphiphilic material and the pharmaceutical substance, with the complex being substantially not soluble in aqueous liquids at a physiological pH. Preferably, the amphiphilic material and the pharmaceutical substance have oppositely charged ionic portions which associate to form an ion pair complex. Such an ion pair complex is referred to as a hydrophobic ion pair (HIP) complex. Thus, the pharmaceutical substance may comprise a cationic portion which associates with an anionic portion of the amphiphilic material or an anionic portion which associates with a cationic portion of the amphiphilic material.

The pharmaceutical substance mad be any substance which may be administered to a human or animal host for medical purpose, which is normally a curative, therapeutic, preventive, or diagnostic purpose. The pharmaceutical substance is preferably directly soluble to some meaningful degree in an aqueous liquid at a physiological pH. As used herein, a physiological pH is a pH of from about 1 to about 8. Preferably, the pharmaceutical substance exhibits a charged character when dissolved in an aqueous liquid at a physiological pH. As used herein, a pharmaceutical substance includes various salt forms of a substance as well as ionic forms and dissociation products, such as may be found in an aqueous solution.

The pharmaceutical substance mad comprise a protein or other polypeptide, a nucleic acid, an analgesic or another material. The following is a non-limiting list of representative types of pharmaceutical substances which may be used with the present invention with a few specific examples listed for each type of pharmaceutical substance: cholinergic agonists (pilocarpine, metoclapramide); anticholinesterase agents (neostigmine, physostigmaine); antimnuscarinic drugs (atropine, scopalamine); antiadrenergics (tolazoline, phentolamine, propranolol, atenolol); ganglionic stimulating agents (nicotine, trimethaphan); neuromuscular blocking agents (gallamine, succinylcholine): local anesthetics (procaine, lidocaine, cocaine); benzodiazepines (triazolam); antipsychotics (chlorpromazine, triflupromazine); antidepressants (fluoxetine, imipramine, amitriptyline, pheneizine); antiparkinson's drugs (L-dopa, dopamine); opioids and anti-opoids (morphine, naloxone, naltrexone, methadone); CNS stimulants (theophylline, strychnine); autocoids and anti-autocoids (histamine, betazole, chlorpheniramine, cimetidine); anti-inflammatories (tolmetin, piroxicam); anti-hypertensives (clonidine, hydralazine, minoxidil); diuretics (metalozone, bumetamide); polypeptides (lysopressin, vasopressin, oxytocin, insulin, calcitonin, gene-related peptide. LHRH agonists, ACTH, growth hormone); antifungals (clotrimazole, miconazole); antimalarials (chloroquine, primaquine); antiprotozoals (pentamidine, melarsoprol); antiheiminthics (piperazine, oxamniquine); antimicrobials (streptomycin, erythromycin, cefaclor, ceftriaxone, oxytetracycline, rifampicin, isoniazid, dapsone); aminoglycosides (gentamycin, neomycin streptomycin); antineoplastics (mechlorethamine, melphalan, doxorubicin, cisplatin); anticoagulants (heparin); nucleic acids (genes, antisense RNAs, ribozymes, plasmids). Additionally, the pharmaceutical substance mad be a sympathomimetic drug such as catecholamines (epinephrine, norepinephrine); noncatecholamine (amphetamine, phenylephrine); and $\beta_2$-adrenergics (terbutaline, albuterol).

Particularly useful with the present invention are macromolecules such as polymers, nucleic acids, proteins or polypeptides. One advantage of the present invention is that the pharmaceutical substance, when in solution with the amphiphilic material in the organic solvent, retains a substantially native conformation. This is particularly important for materials, such as proteins and ribozymes, which are highly susceptible to loss of activity due to loss of native conformational structure.

The amphiphilic material may be any material with a hydrophobic portion and a hydrophilic portion. These materials are typically surfactants. The hydrophilic portion is ionic under the conditions of use. The hydrophobic portion may be any hydrophobic group, such as an alkyl, aryl or alkylaryl group. The amphiphilic material associates with the pharmaceutical substance to form a hydrophobic ion pair which is soluble in the organic solvent when the pharmaceutical substance itself is substantially not soluble in the organic solvent. As used herein, amphiphilic material includes different salt forms of a material as well as ionic forms and dissociation products of a material, such as may be present in a solution. Preferred amphiphilic materials are those posing little or substantially no toxicological problem for a human or animal host.

Examples of anionic amphiphilic materials include sulfates, sulfonates, phosphates (including phospholipids), carboxylates, and sulfosuccinates. Some specific anionic amphiphilic materials useful with the present invention include: sodium dodecyl sulfate (SDS), bis-(2-ethylhexyl) sodium sulfosuccinate (AOT), cholesterol sulfate and sodium laurate. Particularly preferred anionic amphiphilic materials are SDS and AOT.

Preferred cationic amphiphilic materials are the cationic surfactants of the invention (see below). Specific cationic amphiphilic materials include the arginine and cholesterol esters, carbamates, carbonates and ketals (see below).

The solution of the pharmaceutical substance and the amphiphilic material in the organic solvent may be prepared in any suitable manner. In one embodiment of the present invention, small amounts of the amphiphilic material may be added to an aqueous solution, in which the pharmaceutical substance is initially dissolved, until a precipitate forms of an HIP complex of the pharmaceutical substance and the amphiphilic material. The precipitate may then be recovered and dissolved in an organic solvent to provide the desired solution. For some situations, it may be possible to dissolve the pharmaceutical substance in an aqueous liquid and to dissolve the amphiphilic material in an organic solvent. The aqueous liquid and the organic solvent may then be contacted to effect a partitioning of the pharmaceutical substance into the organic solvent to form an HIP complex with the amphiphilic material. In other situations, it may be possible to dissolve both the pharmaceutical substance and the amphiphilic material in an aqueous liquid. The aqueous liquid may then be contacted with an organic solvent to partition into the organic solvent at least some of the pharmaceutical substance and the amphiphilic material in the form of an HIP complex.

The organic solvent may be any organic liquid in which the pharmaceutical substance and the amphiphilic material, together, are soluble, such as in the form of an HIP complex. The following is a non-limiting, representative list of some organic solvents, with specific exemplary solvents listed in parentheses, which mad be used with the present invention: monohydric alcohols (methanol, ethanol, 1-propanol, 2-propanol, 1-butanol, 1-hexanol, 1-octanol trifluoroethanol); polyhydric alcohols (propylene glycol, PEG 400, 1,3-propanediol); ethers (tetrahydrofuran (THF), diethyl ether, diglyme); alkanes (decalin, isooctane, mineral oil); aromatics (benzene, toluene, chlorobenzene, pyridine); amides (n-methyl pyrrolidone (NMP), N,N-dimethylformamide (DMF)); esters (ethyl acetate, methyl acetate); chlorocarbons ($CH_2Cl_2$, $CHCl_4$, 1,2-dichloroethane); and others such as nitromethane, acetone, ethylene diamine, acetonitrile, and trimethyl phosphate.

In one embodiment, the present invention involves the use of amphiphilic materials as ion pairing agents to modulate the solubility and partitioning behavior of pharmaceutical substances such as polypeptides, proteins, nucleic acids, and drugs. Complexes are formed by stoichiometric interaction of an amphiphilic material, such as a detergent or other surfactant (e.g., alkyl sulfate, such as sodium dodecyl sulfate (SDS), or arginine ester), with the ionic functional groups of a polypeptide, protein, nucleic acid, or organic molecule that are accessible for ion pairing. The basic group may be an amine (as found in the lysine amino acid residue or the N-terminal amino group of a polypeptide) or a guanidinium group (as in arginine). The acidic group may be a carboxyl group or phosphate group. An ion pair is subsequently formed, referred to as a hydrophobic ion pair (HIP) complex. The HIP complex formed will have reduced aqueous solubility, but enhanced solubility in organic solvents.

It has been discovered that an HIP complex may be dissolved in an organic solvent to form a true homogeneous solution. Included in the invention is the discovery that the native tertiary structure of proteins is retained even when dissolved in organic solvents such as 1-octanol. The method of the invention for forming a true homogeneous solution is fundamentally different from any other method for placing proteins into organic solvents, such as those which use suspensions, micelles, microemulsions, or chemical modifications of the protein. This discovery holds important implications in the area of drug delivery and release, including delivery to the body by inhalation and dispersion in a hydrophobic biodegradable matrix. While the decreased aqueous solubility of the HIP complex has been observed previously, the use of an HIP complex precipitate for improved drug delivery is novel. Measurement of the apparent partition coefficient, defined as the ratio of the equilibrium concentration in an organic phase to that in an aqueous phase, demonstrates that the solubility of a peptide or protein in an HIP complex in the organic phase is greater by 2–4 orders of magnitude relative to the chloride salt of the peptide or protein.

Included in the invention is the discovery that the precipitation of the HIP complex out of aqueous solution may be controlled for the production of uniform HIP complex particles of a desired size. These particles may then be formed into a suspension. This invention also includes a method of obtaining HIP complex particles of specific sizes by controlling the conditions of HIP complex precipitation.

The discovery that HIP complex precipitation can be controlled so as to yield particles of specific size can be exploited to effect the rate of drug released from suspensions. In one embodiment of a method of the invention, the size of HIP complexes is controlled by controlling the rates of the mixing of a protein solution and the addition of an anionic or cationic detergent to the protein solution. The HIP complex can produce very fine suspensions which have limited solubility in water, and the technology can be used to produce particles of varying specific size. The particle size of the HIP complex which is formed in water will depend on the degree of agitation of the protein solution and the rate of counterion addition. The smallest particles are produced with high shear being applied to the aqueous protein solution and slow addition of detergent. This approach is also important in pulmonary drug delivery, where the particle size is critical to delivery to certain sites within the lung. To obtain particles which will be capable of depositing in the pulmonary region upon inhalation, a high speed homogenizer can be used to stir the protein solution and a surfactant is added dropwise to the agitated solution. Particles in the 2–10 micron range can be obtained using this procedure. Particles of this size are required to get a sufficient amount of protein delivered to the lung to have a beneficial effect. The particles once formed can be separated by centrifugation or filtration. Larger particles will be formed with slow agitation speeds and more rapid addition of surfactant. One example of a drug which could benefit from formation into a fine suspension of HIP complexes is DNase, an enzyme currently being used by cystic fibrosis patients to dissolve viscous fluid build-up in the lung. Other examples include protein and peptide enzyme inhibitors currently being tested for the treatment of emphysema. Further examples include antituberculosis drugs (e.g. streptomycin, isoniazid, pyrazinamide, ethambutol). Another example is transgenes used to transfect lung cells for gene therapy.

The invention includes a method of controlling the release of a protein from a suspension by controlling the size of the HIP complex particle. The release rate of protein into an aqueous solution from an HIP complex will be much slower than that of the protein itself. This rate will be a function of the particle size of the complex and the solubility of the complex in water or biological fluid. The solubility is a function of the amphiphilic material used and the strength of its association with the protein. Therefore, extended (controlled) release of the protein from the suspension can be achieved. This property permits proteins to be formulated as a suspension for depot injection.

This invention also includes the discovery that uncomplexed protein released from the HIP complex can be extracted back into aqueous medium with retention of its native structure. The native uncomplexed protein can be reclaimed by dissolution in an aqueous solution which contains an excess of chloride or other counterion, indicating that the complexation is an entirely reversible process. It has been discovered that the protein of the HIP complex subsequently extracted back into an aqueous medium retains its native structure. This makes HIP methodology useful in the delivery of proteins for use as therapeutic agents.

An important and unique aspect of the present invention is the discovery that HIP complexes display greatly enhanced thermal stability relative to the native protein, both with respect to chemical degradation and denaturation. This suggests that the HIP complex is useful for long term storage of the protein. Further, this aspect of the invention permits high temperature (steam) sterilization of proteins without the loss of biological activity, which until now, could not be accomplished. Currently, polymer delivery systems for proteins are usually sterilized by radiation as proteins are destroyed by heat. The present invention discloses a method by which proteins may be processed by heating at sterilizing temperatures. Further, the enhanced thermal stability of the present invention may be important for the formulation of proteins in maintaining an active enzyme in an organic solvent and for long term storage of sensitive proteins.

Included in this invention is a method of uniformly distributing a drug throughout a hydrophobic polymer comprising adding a sufficient amount of a detergent to an organic molecule to form a precipitate, isolating the precipitate, and co-dissolving the precipitate and a hydrophobic polymer in an organic solvent to form a homogeneous distribution of the organic molecule within the polymer.

Many of the current systems for the controlled release of proteins make use of biodegradable polymers. There are at least two major problems with such systems. Under the prior art, a protein can only be suspended during the incorporation process, and because of its polar surface does not suspend well. The term "suspension" refers to the dispersion of a substance or substances in another where the boundaries between them are well defined. A material is dispersed in a solvent where the material has limited solubility in that solvent. This leads to an uneven distribution of the drug and irreproducible drug release profiles. Secondly, the water-soluble drug is leached out of the polymer by biological fluids (rather than its controlled release as the polymer is slowly degraded).

The invention provides a new method for distributing a drug uniformly through a hydrophobic polymer. HIP complex formation permits both proteins and hydrophobic polymers to possess similar solubility parameters, thus facilitating incorporation of the protein into the polymer matrix. The inventors have discovered that HIP complexes may be uniformly distributed in biodegradable polymers as they possess a solubility in solvents that will also dissolve the polymer. Where the HIP complex does not dissolve in the solvent used it will suspend easily as a result of its hydrophobic surface.

The invention wherein the drugs being delivered are included in the polymer matrix in an HIP complex represents three advantages over the biodegradable polymer systems: (1) the hydrophobic polymers can be better mixed with the drug in its lipophilic ion-pair state; (2) the drug forms hydrophobic particles within the polymer, and avoids the problem of the formation of a concentration of polar particles at the interface of the polymer leading to the "burst" effect: (3) the hydrophobic particles dispersed within the biodegradable polymer are not leached out by biological fluids which result in a predictable release rate. The inventors have discovered the use of the HIP complex to control (retard or extend) the release of a drug at a predictable rate, resulting in part from a more uniform formulation.

One embodiment of this invention includes a method for achieving a true homogeneous solution of biologically active proteins and polypeptides in a organic solvent. None of the methods by which enzymatic activity is achieved in a nonaqueous environment employs a true protein solution. The inventors have discovered that the HIP complex can be redissolved in an organic solvent such that a true homogeneous solution is formed. This discovery has important ramifications for controlling the enzymatic activity of proteins in the body. Through the formation of HIP complexes, enzymes and other proteins can be solubilized in a variety of organic solvents, including ethanol, propylene glycol and glycols in general. N-methyl pyrrolidone (NMP) and others. These materials should have altered enzymatic activity and specificity. It is important to note that use of HIP complexes to form true solutions of biologically active proteins and polypeptides is a fundamentally different approach from any previously described for achieving enzymatic activity in non-aqueous media.

Also included in this invention is the discovery that the HIP complex dissolved in organic solvent can be extracted back into aqueous medium with retention of the native protein structure. This discovery has potential use in the purification of proteins. A protein having a pH different from others in a mixture may be extracted or preferentially precipitated from the mixture by HIP complex formation.

The invention further includes a method of obtaining a stabilized protein comprising precipitating a protein in the HIP complex. Much research effort has been directed into developing stabilized lyophilized formulations of proteins, including by the addition of cryoprotectants. The HIP complex may, in many cases, provide a simple alternative to obtaining a stabilized protein. A protein in the solid HIP complex has enhanced stability and resistance to degradation through storage, shipping, and handling. Chemical stability is conferred because the amount of water present is relatively low, as in lyophilized powders. To reconstitute the protein, the HIP complex is suspended in a diluent containing a significant chloride concentration (e.g. phosphate buffered saline (PBS) or normal saline). Most HIP complexes redissolve rapidly and completely, leaving a solution whose only additive is a small amount of surfactant. The protein can also be stored as a stable entity by dissolving or suspending the HIP complex in an organic solvent or solvent mixture. To form an aqueous solution of the protein, the solution or suspension can be shaken with water containing chloride. In cases where the organic solvent is immiscible with water, the protein will partition into the water.

An additional embodiments of this invention is a method of incorporating proteins and other drugs into lipid vesicles, liposomes, or detergent. Shaking of an oil-water mixture with an HIP complex of a protein leads to emulsification, indicating that a HIP complex can more easily be introduced into emulsion delivery systems than the drug alone. Systems for such use can be designed using either the insoluble material in suspension formulations or in oil formulation, such as oil in water emulsions. Other examples include nasal and pulmonary aerosols, ophthalmic suspensions, transdermal patches, lozenges, chewing gum, buccal and sublingual systems, and suppositories.

Another aspect of this invention is the reduction of the bitter taste of drugs incorporated into HIP complexes, since only compounds in solution are tasted. Therefore, this invention includes a method for improving the taste of orally administered drugs by formation of insoluble HIP complexes with such drugs. The taste of a substance is detected by receptors in the tongue. A major approach to modifying the taste of a drug is to alter its solubility in saliva. If the solubility is sufficiently low the taste will not be noted. The low solubility of the HIP complex in biological fluids, including saliva, can be used to mask the flavor of a drug, optionally, the HIP complexes may be incorporated into a polymer to further mask the taste of the drug. Another way to mask taste is to partition the drug into an oil, such as olive oil. This can then be given as an oil in water emulsion with flavoring agents added to the outer water phase. HIP complex formation would provide the drug with the necessary high oil to water partition coefficient.

The term "hydrophobic ion-pairing (HIP)" as used in this disclosure refers to the interaction between an amphiphilic material and a pharmaceutical substance. Preferred amphiphilic materials include detergents which interact with proteins, other polypeptides and nucleic acids. "HIP complex derivatives" are substances modified by formation of a hydrophobic ion-pair. The detergent interacts with an oppositely charged compound, such as a polypeptide or nucleic acid. This interaction has been termed HIP because it appears to be primarily electrostatic in nature.

As used in the present invention, the term "anionic detergents" encompasses any hydrophobic material that is a salt of an acid which can be employed to modify solubility properties in the described way, including sulfates, sulfonates, phosphates, and carboxylates. Sulfates are the salts of the stronger acids in this series and, therefore, the most efficient at forming ion pairs. Provided that the alkyl chains or aryl rings are of 8–18 carbons in length, they are potential candidates for HIP methodology.

As used in the present invention, the term "cationic surfactants" encompasses any material having a hydrophobic moiety and a cationic moiety which can be employed to modify solubility properties in the described way. Preferred are the biocompatible cationic surfactants of the invention (see below).

Although the solution having the HIP complex dissolved in the organic solvent is itself a valuable product, the solution may also be used in the preparation of additional pharmaceutical products. In particular the solution may be used to prepare a powder of solid particles comprising the pharmaceutical substance and the amphiphilic material. In a preferred embodiment, the solution is subjected to antisolvent precipitation processing to prepare a powder of solid particles. Powders may be prepared having particles of an ultrafine size and a relatively narrow size distribution. Also, hollow elongated, fiber-like particles of a small size may be prepared. These particles have unique properties which may be desirable for various pharmaceutical applications.

Figure 12:
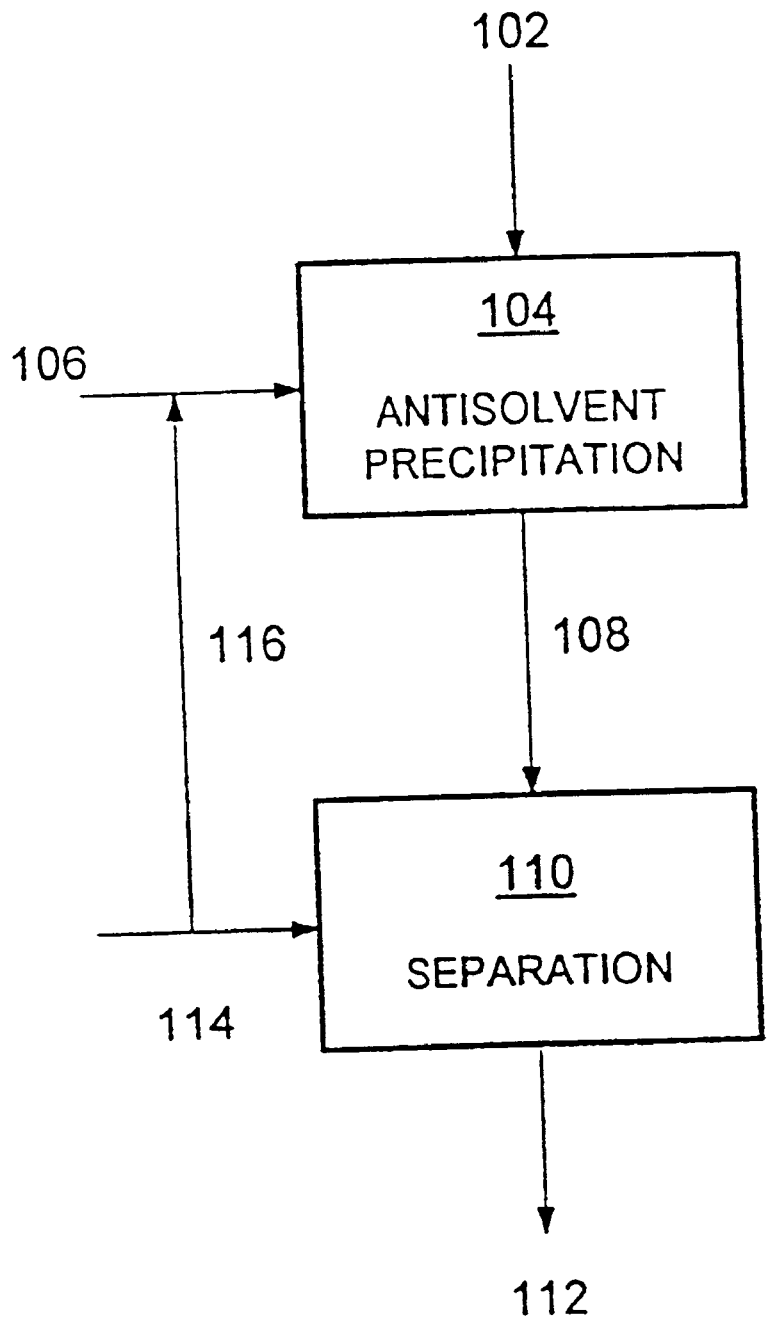
FIG. 12 shows a process flow diagram for one embodiment of an antisolvent precipitation method for producing pharmaceutical powders.

With reference to FIG. 12, one embodiment of an antisolvent precipitation method of the present invention is shown. A liquid feed solution 102 is provided having a pharmaceutical substance and an amphiphilic material dissolved together in an organic solvent, which is used as a carrier liquid for processing of the pharmaceutical substance. The liquid feed solution 102 is subjected to antisolvent precipitation 104 in which the liquid feed solution 102 is contacted with an antisolvent fluid 106. During the antisolvent precipitation 104, the antisolvent fluid 106 invades the organic solvent of the liquid feed solution 102, resulting in precipitation of solid particles comprising the pharmaceutical substance and the amphiphilic material. The resulting mixture 108, having the precipitated particles, is subjected to separation 110 in which solid particles 112 are separated from the exiting fluid 114. A portion 116 of the exiting fluid 114 is recycled to form a part of the antisolvent fluid 106 and a portion 118 of the exiting fluid 114 is bled from the system to prevent an undesirable build-up of the organic solvent in the system. Continuous or batch processes other than the process shown in FIG. 12 may also be used according to the present invention.

The antisolvent fluid is a fluid in which the pharmaceutical substance and the amphiphilic material, in association, are substantially not soluble. It should be understood that it is possible that the antisolvent fluid may be capable of dissolving some amount of the pharmaceutical substance and the amphiphilic material without departing from the scope of the present invention. The antisolvent fluid, however, is substantially incapable of dissolving a significant portion of the pharmaceutical substance and the amphiphilic material from the liquid feed solution such that at least a significant portion of pharmaceutical substance and the amphiphilic material are, in effect, not soluble in the antisolvent fluid. Also, the antisolvent fluid is at least partially miscible with the organic solvent such that the antisolvent fluid is capable of penetrating into the organic solvent sufficiently to cause the desired precipitation of the pharmaceutical substance and the amphiphilic material.

Preferably, the antisolvent precipitation 104 is conducted under thermodynamic conditions which are near critical or supercritical relative to the antisolvent fluid. Preferably, the antisolvent precipitation is such that the antisolvent fluid is at a reduced pressure of greater than about 0.5, with the reduced pressure being the ratio of the total pressure during the antisolvent precipitation 104 to the critical pressure of the antisolvent fluid 106. More preferably the contacting occurs at a reduced pressure of from about 0.8 to about 2.0 relative to the antisolvent fluid and even more preferably at a reduced pressure of from about 0.8 to about 1.2. Preferably, the antisolvent precipitation 104 is at a reduced temperature of greater than about 0.75, with the reduced temperature being the ratio of the temperature (in K) during the antisolvent precipitation 104 to the critical temperature (in K) of the antisolvent fluid 106. More preferably, the contacting occurs at a reduced temperature of greater than about 0.85, even more preferably greater than about 0.9 and most preferably greater than about 0.95. Typically, the reduced temperature is smaller than about 1.2.

The antisolvent fluid may comprise any suitable fluid for near critical or supercritical processing. These fluids include carbon dioxide, ammonia, nitrous oxide, methane, ethane, ethylene, propane, butane, pentane, benzene, methanol, ethanol, isopropanol, isobutanol, fluorocarbons (including chlorotrifluoromethane, monofluoromethane, hexafluoroethane and 1,1-difluoroethylene), toluene, pyridine, cyclohexane, m-cresol, decalin, cyclohexanol, o-xylene, tetralin, anilin acetylene, chlorotrifluorosilane, xenon, sulfur hexafluoride, propane, and others. Carbon dioxide, ethane, propane, butane and ammonia are preferred antisolvent fluids.

For many pharmaceutical substances, it is desirable to use an antisolvent fluid which permits processing at relatively mild temperatures. This is particularly important for processing proteins and other polypeptides which are susceptible to a loss of biological activity when subjected either to very low temperatures or to very high temperatures. For applications involving proteins and other large polypeptides, the antisolvent fluid should preferably have a critical temperature of from about 0° C. to about 50° C. Included in this category of antisolvent fluids are carbon dioxide, nitrous oxide, ethane, ethylene, chlorotrifluoromethane, monofluoromethane, acetylene, 1.1-difluoroethylene, hexafluoroethane, chlorotrifluorosilane, and xenon. A particularly preferred antisolvent fluid is carbon dioxide because it is readily available, non-toxic, and has a critical temperature of 31° C. and a critical pressure of 72.9 atm, which permits processing under relatively mild conditions.

The contacting of the liquid feed solution 102 with the antisolvent fluid 106 during the antisolvent precipitation 104 may be accomplished using any suitable contacting technique and contacting apparatus. Preferably, the liquid feed solution 102 is sprayed as small droplets into the antisolvent fluid 106. A sonicated spray nozzle, which is vibrated ultrasonically, has been found to work well because it is capable of producing very small droplets of a relatively uniform size and is, therefore, conducive to preparation of ultrafine powders having particles of a narrow size distribution. The contacting may be performed in a batch operation or continuously. Also, continuous operation could involve contacting by concurrent flow or countercurrent flow.

The separation 110 may be accomplished using any suitable separation technique and apparatus. For example, the separation may involve simple density separation, filtration or use of a centrifuge.

The antisolvent precipitation process of the present invention may be used to produce ultrafine particles of a narrow size distribution and which are often of spheroidal shape. The ultrafine particles may be as large as about 10 microns or may be 1 micron or smaller. The size of the particles produced will depend upon the particular pharmaceutical substance and the processing conditions used.

In general, particle size becomes larger as the viscosity and surface tension of the organic solvent increases. For example, the use of ethanol as an organic solvent would generally produce smaller particles than the use of isopropanol as an organic solvent. Also, particles generally tend to become larger in the vicinity of the critical temperature as the process temperature approaches the critical temperature from above. If the process temperature is too high, however, then particle sizes generally tend to become larger again. For example, using carbon dioxide, the smallest particles seem to be produced around a temperature of about 35° C, with larger particles generally being produced at substantially higher and lower temperatures. When using carbon dioxide, the pressure is preferably within the range of from about 70 bars to about 90 bars.

It has been found that the method of the present invention may be used to produce particles of a narrow size distribution. Preferably, particles produced in the gas antisolvent precipitation method of the present invention are such that greater than about 90 weight percent of the particles are within about 50 percent larger or smaller than a weight average particle size.

In addition to varying the size of the particles, it is also possible to vary the shape of the particles produced. For example, it is possible to produce spheroidal shaped particles which have good flowability properties. Also, it has been found that hollow fiber-like particles may be made according to the present invention, the length of which may vary depending upon processing conditions. These fiber-like particles have a tubular quality in that they comprise an elongated body, of a substantially rounded cross-section, which has a hollow interior, which typically is open at least one end of the elongated body, and is preferably open at both ends of the elongated body.

It has been found that these fiber-like particles tend to form when the pharmaceutical substance is subjected to gas antisolvent precipitation at a very high concentration in the organic solvent, such that the molecules of the pharmaceutical substance tend to be entangled when dissolved in the organic solvent. Macromolecules are particularly susceptible to such entanglement in solution and are, therefore, preferred for making these fiber-like particles. Such macromolecules include polymers and polypeptides, including proteins. The concentrations required for any particular pharmaceutical substance will depend upon the specific pharmaceutical substance being processed, but concentrations of 5 to 10 weight percent or higher, relative to the organic solvent, may be required for many polypeptide macromolecules.

The fiber-like particles typically have a diameter of smaller than about 100 microns, preferably smaller than about 50 microns. In some cases, the diameter mad be as small as 10 microns or less. Length may vary from about 0.3 mm or less to as long as 1 cm or more, and is preferably longer than about 0.5 mm and more preferably longer than about 1 mm. Generally, a lower flow rate of the liquid feed solution during gas antisolvent precipitation tends to produce longer fiber-like particles and a higher flow rate tends to produce shorter fiber-like particles.

These hollow, fiber-like particles offer a number of advantages for use in the pharmaceutical industry, one advantage is that these fiber-like particles have a shape that will not, upon ingestion, pass as easily as a spheroidal particle through the stomach. The fiber-like particles should, therefore, tend to have a longer retention time in the stomach region and would, accordingly, be available in a stomach region for a longer period of time for the desired pharmaceutical treatment. Another advantage of the fiber-like particles is that, because they are hollow, it is possible to place smaller particles of another pharmaceutical substance inside the hollow interiors. For example, small particles of morphine or pentamidine could be loaded into the hollow interiors of a protein-based fiber-like particle.

In addition to the pharmaceutical substance and the amphiphilic material, a biodegradable polymer mad also be incorporated into the solid particles of the present invention, as noted previously, for controlled release of the pharmaceutical substance. A biodegradable polymer may be incorporated in the antisolvent precipitation method of the present invention by co-dissolving the biodegradable polymer in the organic solvent along with the pharmaceutical substance and the amphiphilic material. The particles produced during antisolvent precipitation will then contain the biodegradable polymer as well as the amphiphilic material" and the pharmaceutical substance. The biodegradable polymer may be used in any convenient amount relative to the pharmaceutical substance. The weight ratio of the biodegradable polymer to the pharmaceutical substance could vary from about 0.1 to 1 to about 100,000 to 1 depending upon the application. Most controlled release applications, however, will involve a ratio of from about 10 to 1 to about 100 to 1.

Incorporation of the biodegradable polymer into the solid particles may be used to delay release of the pharmaceutical substance and to permit sustained release of the pharmaceutical substance over some extended period of time. It has been found that the release profile from a particle of the present invention in an aqueous buffer solution for the pharmaceutical substance is relatively constant and that a sudden initial release, or "burst effect." is avoided. This indicates that the pharmaceutical substance is not concentrating near the surface of the particle and that the particle comprises an intimate and homogeneous mixture of the pharmaceutical substance, the amphiphilic material and the biodegradable polymer.

Any biodegradable polymer mad be used which may be co-dissolved in the organic solvent along with the pharmaceutical substance and the amphiphilic material. Examples of such biodegradable polymers include those having at least some repeating units representative of polymerizing at least one of the following: an alphahydroxycarboxylic acid, a cyclic diester of an alphahydroxycarboxylic acid, a dioxanone, a lactone, a cyclic carbonate, a cyclic oxalate, an epoxide, a glycol, and anhydrides. Preferred is a biodegradable polymer comprising at least some repeating units representative of polymerizing at least one of lactic acid, glycolic acid, lactide, glycolide, ethylene oxide and ethylene glycol. The biodegradable polymers may be a homopolymer or a copolymer of two or more different monomers.

Preferred homopolymers include poly(lactic acid), polylactide, poly(glycolic acid), polyglycolide and poly (ethylene glycol).

A further aspect of the present invention involves use of solid particles of the present invention in pharmaceutical delivery applications. To deliver a pharmaceutical substance, solid particles having the pharmaceutical substance and the amphiphilic material according to the present invention are introduced into a human or animal host.

In one embodiment, the solid particles are inhaled for pulmonary delivery. For pulmonary delivery, it is preferred that greater than about 90 weight percent of all of the solid particles in an administered pharmaceutical formulation are of a size smaller than about 10 microns and more preferably at least about 90 weight percent of said particles are smaller than about 6 microns, and even more preferably at least about 90 weight percent of all of said solid particles are from about 1 micron to about 6 microns. Particularly preferred for pulmonary delivery applications are particles of from about 2 microns to about 5 microns in size. These particles may also comprise a biodegradable polymer for delayed and/or sustained release of the pharmaceutical substance. The ultrafine size and narrow size distribution of the solid particles of the present invention permit a much higher utilization of the pharmaceutical substance for pulmonary delivery than the low utilization experienced with present methods for pulmonary delivery of pharmaceutical substances. Whereas current aerosol and nebulization techniques may use only 10 percent of a pharmaceutical substance which is administered, with the particles of the present invention, 80 percent or more of a pharmaceutical substance which is administered may be utilized.

The solid particles of the present invention may also be placed in a suspension and the suspension injected into the hosts. For intramuscular or subcutaneous injection, the particles will often comprise a biodegradable polymer for sustained release of the pharmaceutical substance. For intramuscular or subcutaneous injection, the particles should be less than about 100 microns in size, most preferably less than about 50 microns in size, although smaller or larger particles may be used in some applications.

For intravenous injection, substantially all particles should be of a size smaller than about 1 micron so that the particles will not be susceptible to creating a blockage within the circulatory system. The particles may comprise a biodegradable polymer, if desired.

For any treatment requiring injection of a suspension over a prolonged period, such as for a micropump which continuously injects a suspension at a slow rate, greater than about 90 weight percent of the particles are preferably smaller than about 1 micron to reduce problems associated with settling of the solid particles. More preferably, substantially all particles are smaller than about 1 micron.

The fiber-like particles should be useful in a number of pharmaceutical applications to deliver a pharmaceutical substance to a location where it is needed. For example, due to their hollow, fibrous shape, these particles should tend to absorb water due to capillary action. The fiber-like particles, may, therefore accelerate biodegradation of a biodegradable polymer relative to a particle which is not hollow. Also, the fiber-like particles could be woven or spun, alone or with other fibrous materials, to incorporate a pharmaceutical substance into a medical product using the woven or spun materials. For example, the fiber-like particles could be made to include a growth factor. Some of the fiber-like particles then may be used in making wound coverings, from which the growth factor could be delivered to the wound. In addition, the fiber-like particles could be used as a support for the growth of cells. Also, the fiber-like particles could be incorporate into graft such as arterial grafts by spinning with other fibers such as Dacron™ or another material. The fiber-like particles could include a pharmaceutical substance to enhance healing in the vicinity of the graft or the acceptance of the graft. Moreover, the fiber-like particles could be used in the manufacture of patches for delivery of a pharmaceutical substance, including patches for sublingual or buccal delivery of a pharmaceutical substance.

Particles of the present invention, having the ion-paired pharmaceutical substance, may also be used to enhance properties of immune system boosters to elicit an immune system response. Rather than injecting a solution of an antigenic protein or other peptide with an adjuvant, such as aluminum hydroxide, to cause precipitation after injection, a suspension of the ion-paired particles of the present invention could be used. In another embodiment, the particles of the present invention could be used in cements, to deliver a growth factor to help heal broken bones or teeth.

The invention further provides novel cationic surfactants having the formula:

P-L-C wherein:

P is a biocompatible hydrophobic moiety;

C is a biocompatible cationic moiety: and

L is a biodegradable linkage linking P and C.

"Biocompatible" is used herein to mean that the hydrophobic or cationic moiety is naturally-occurring in, or is well-tolerated by, cells (including prokaryotic and eukaryotic cells) or an organism (including animals (e.g., humans) and plants). A "biodegradable linkage" is one which is degraded by normal conditions or processes found in a cell or organism. Thus, the biodegradable linkage of a cationic surfactant of the invention is degraded into two biocompatible components in a cell or organism to which the cationic surfactant is delivered. As a result, the cationic surfactants of the invention are much less toxic than currently existing cationic surfactants.

P is preferably a saturated or unsaturated, linear, branched or cyclic hydrocarbon (e.g., alkyl, cyclic alkyl, aryl or combinations thereof) containing at least 8 carbon atoms, more preferably 8–40 carbon atoms, most preferably 10–30 carbon atoms. Presently preferred is P which is an alkyl containing 10–20 carbon atoms. Also presently preferred is P which comprises the steroid backbone, the steroid backbone preferably being substituted with C-L- at C3 and/or containing at least one double bond, P most preferably being the cholesterol nucleus. By steroid backbone is meant the fused tetracyclic structure common to all steroids (shown FIG. 26). By cholesterol nucleus is meant cholesterol without the hydroxyl group at C3 and being substituted at C3 with C-L-.

P may be substituted or unsubstituted. The substituent may be any moiety that has at least some degree of hydrophobicity and is of low toxicity to cells or in vivo. Suitable substituents include alkyl, cyclic alkyl, aryl, alkyl esters, alkyl amines, alkyl ethers, etc.

L is preferably an ester, carbonate, carbamate or ketal linkage.

C must be positively charged at pH 7.4 or less. C preferably comprises a guanidinium group or one or more primary, secondary, tertiary or quaternary amines. Thus, C may be an arginine, lysine, choline, ethanolamine, or ethylene diamine residue. C is most preferably an arginine residue.

Particularly preferred cationic surfactants are arginine esters having the following formula:

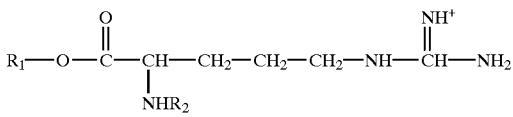

$R_1$, which may be substituted or unsubstituted, is a saturated or unsaturated, linear, branched or cyclic hydrocarbon (e.g. alkyl, cyclic alkyl, aryl, or combinations thereof) containing at least 8 carbon atoms. More preferably $R_1$ contains 8–40 carbon atoms, most preferably 10–30 carbon atoms. Presently preferred is a P which is an alkyl containing 10–20 carbon atoms or is the cholesterol nucleus. Suitable substituents are those listed above for P. $R_1$, may comprise one or more neutral amino acids.

$R_2$ is H, one or more neutral or basic amino acids, including additional arginines, or a linear, branched or cyclic hydrocarbon (e.g. alkyl, cyclic alkyl, aryl, or combinations thereof) containing at least 1, preferably 1–15. most preferably 2–10, carbon atoms and also, optionally, containing at least one amine group within the hydrocarbon, attached to the hydrocarbon (including at either end), or both. Preferred amine groups are quaternary amines and guanidinium groups.

When intended for repeated use in vivo, $R_1$, and R2 are preferably chosen so that they are not immunogenic. Thus, when $R_1$ or $R_2$ is a peptide, it will preferably comprise fewer than 6 amino acids. Methods of making peptides are, of course, well known (also see below). Suitable peptides can also be purchased commercially.

$R_1$ may also be linked to the arginine residue through other biodegradable linkages. Other preferred linkages include ketal, carbonate and carbamate linkages.

Figure 20A:
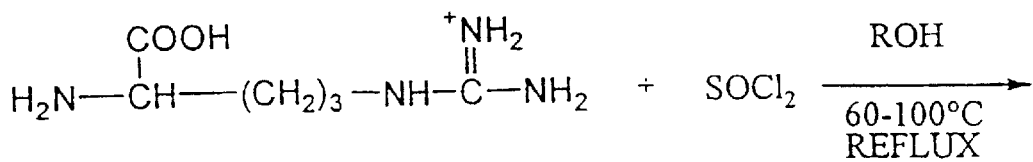
Figure 20A:
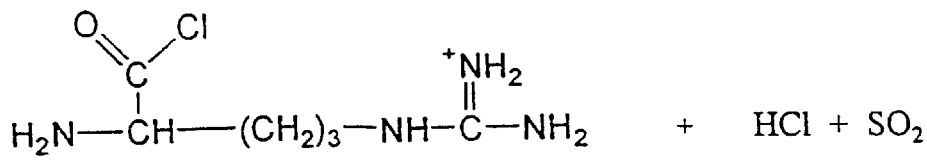
Figure 20A:
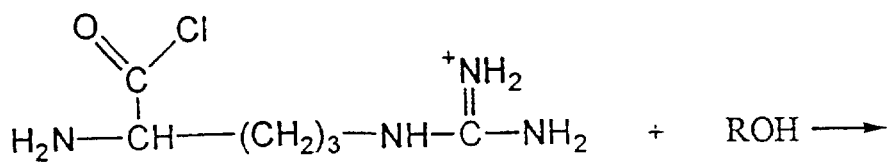
Figure 20A:
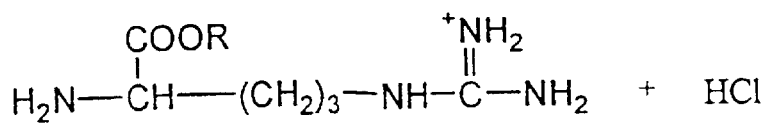
Figure 20B:
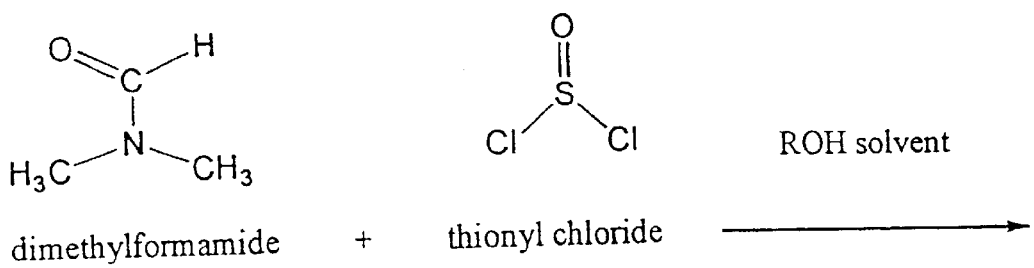
Figure 20B:
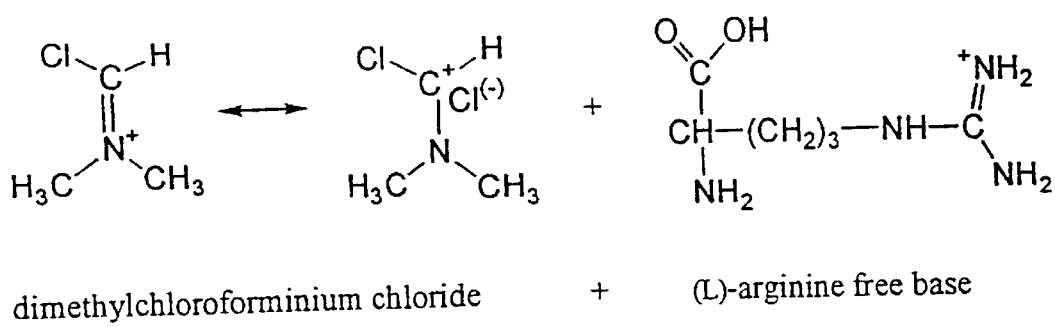
Figure 20B:
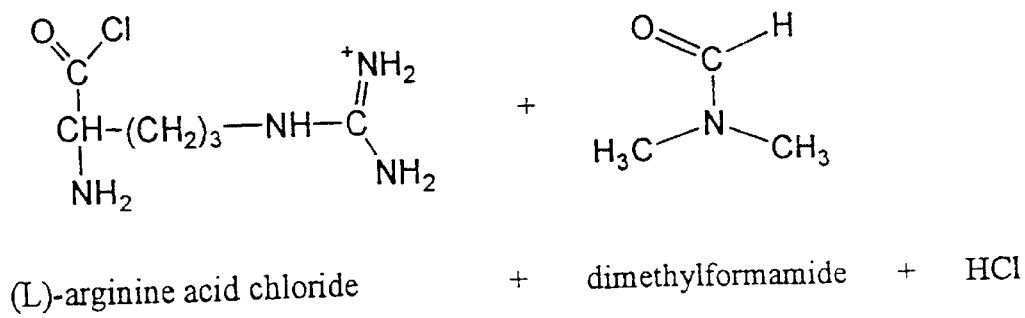
Figure 20C:
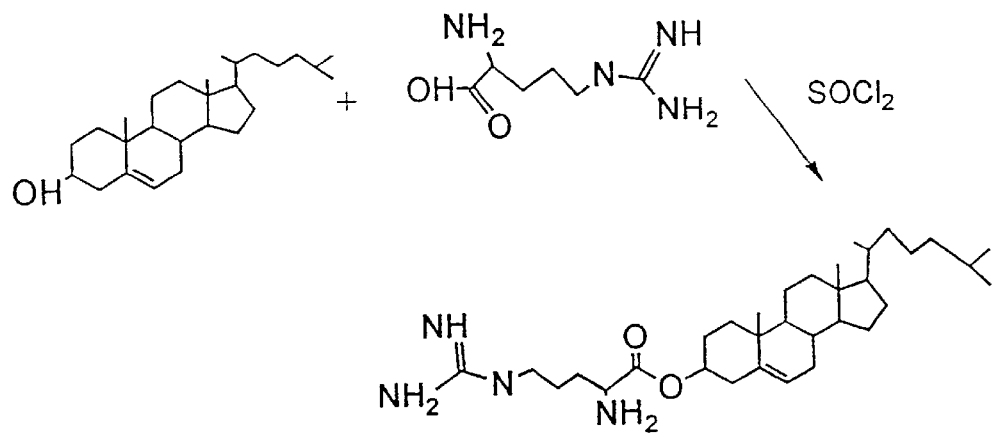
Figure 20D:
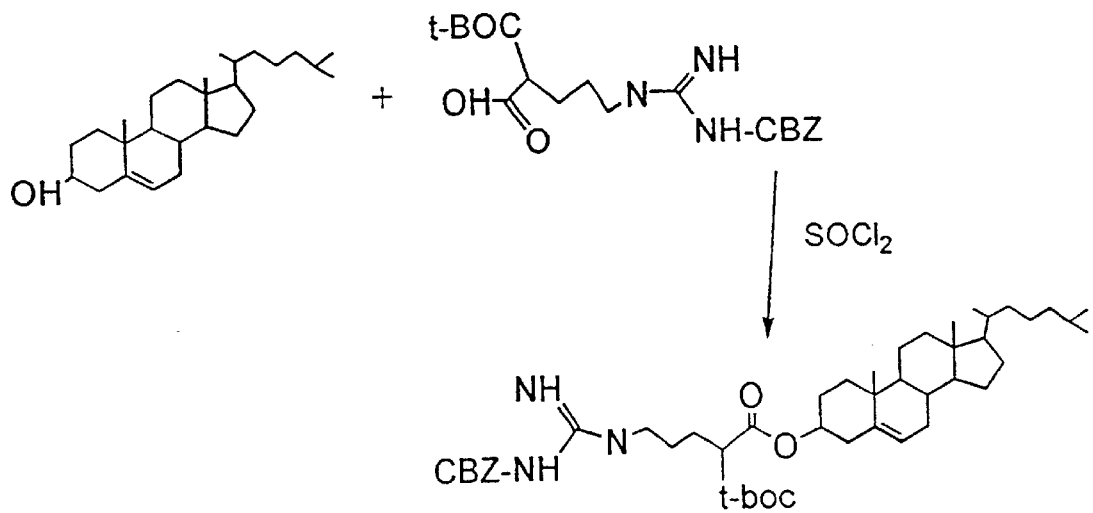
Figure 21A:
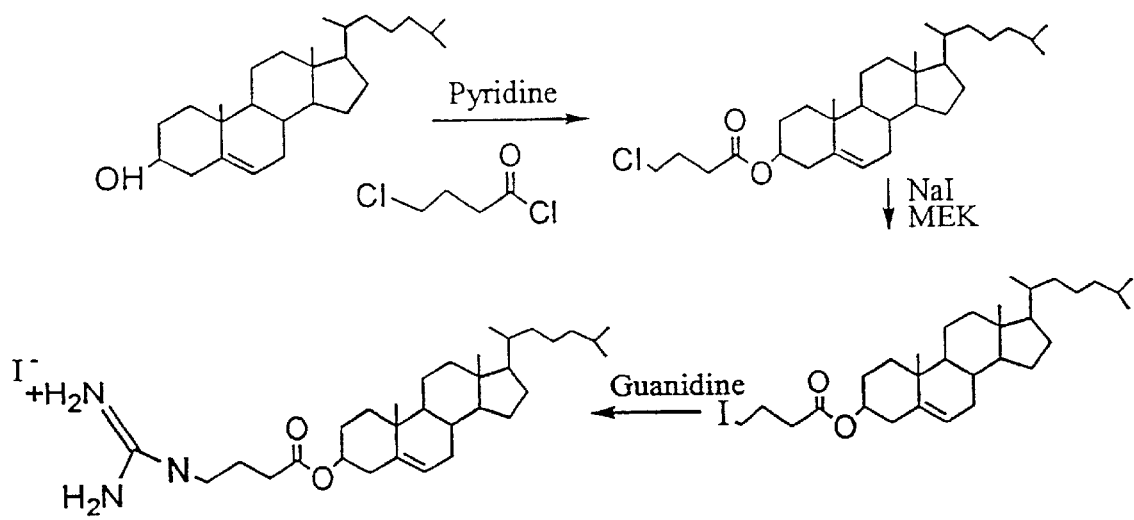
FIGS. 21A–F illustrate schemes for the synthesis of cholesterol esters and carbamates, THF is tertahydrofuran, Me is methyl, MeI is methyliodide, MEK is methyl ethyl ketone.
Figure 21B:
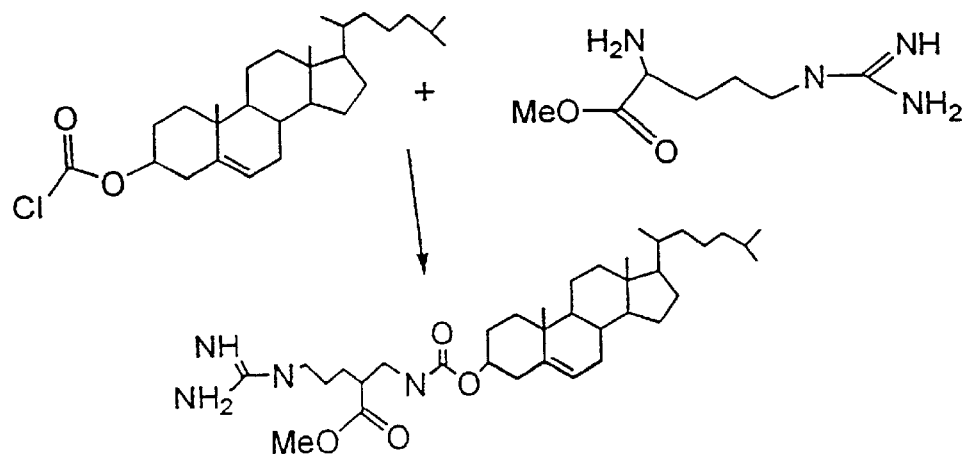
Figure 21C:
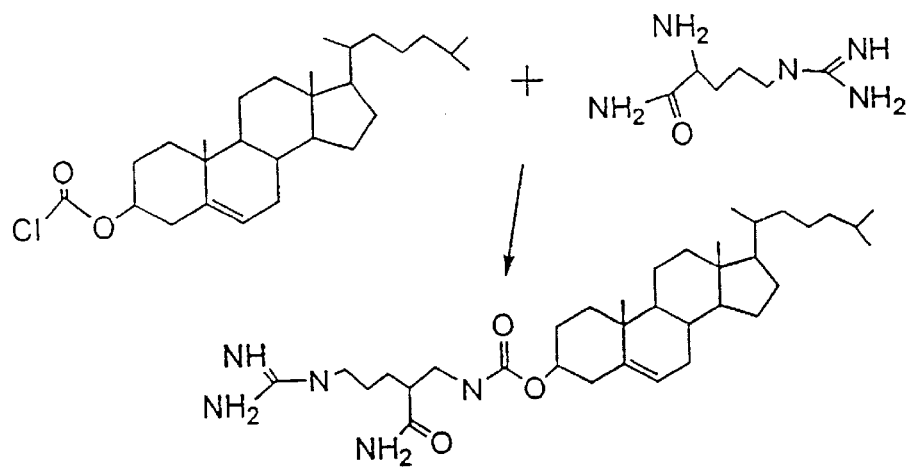
Figure 21D:
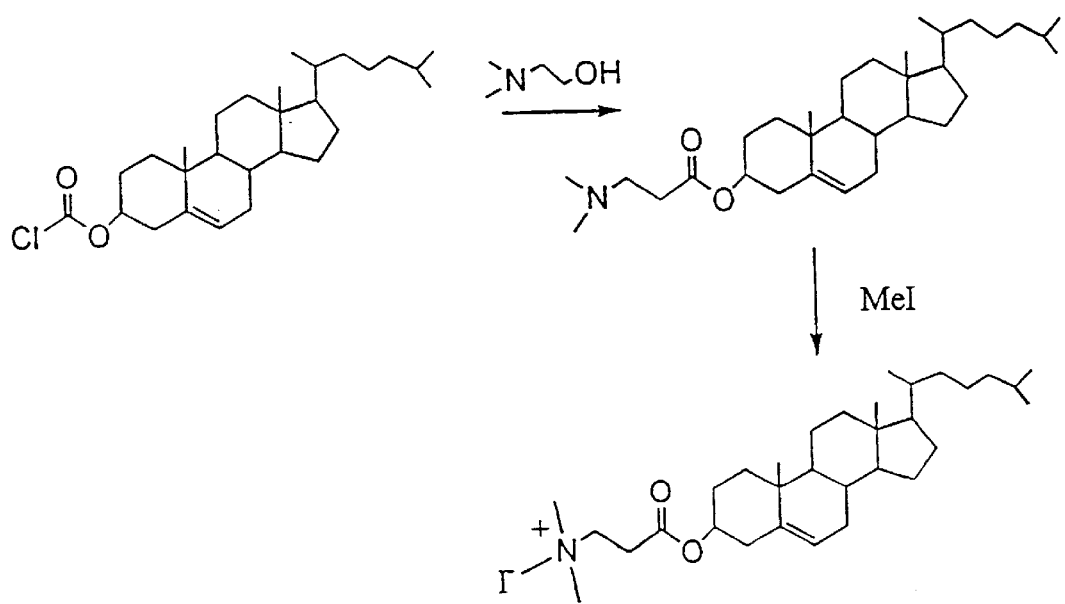
Figure 21E:
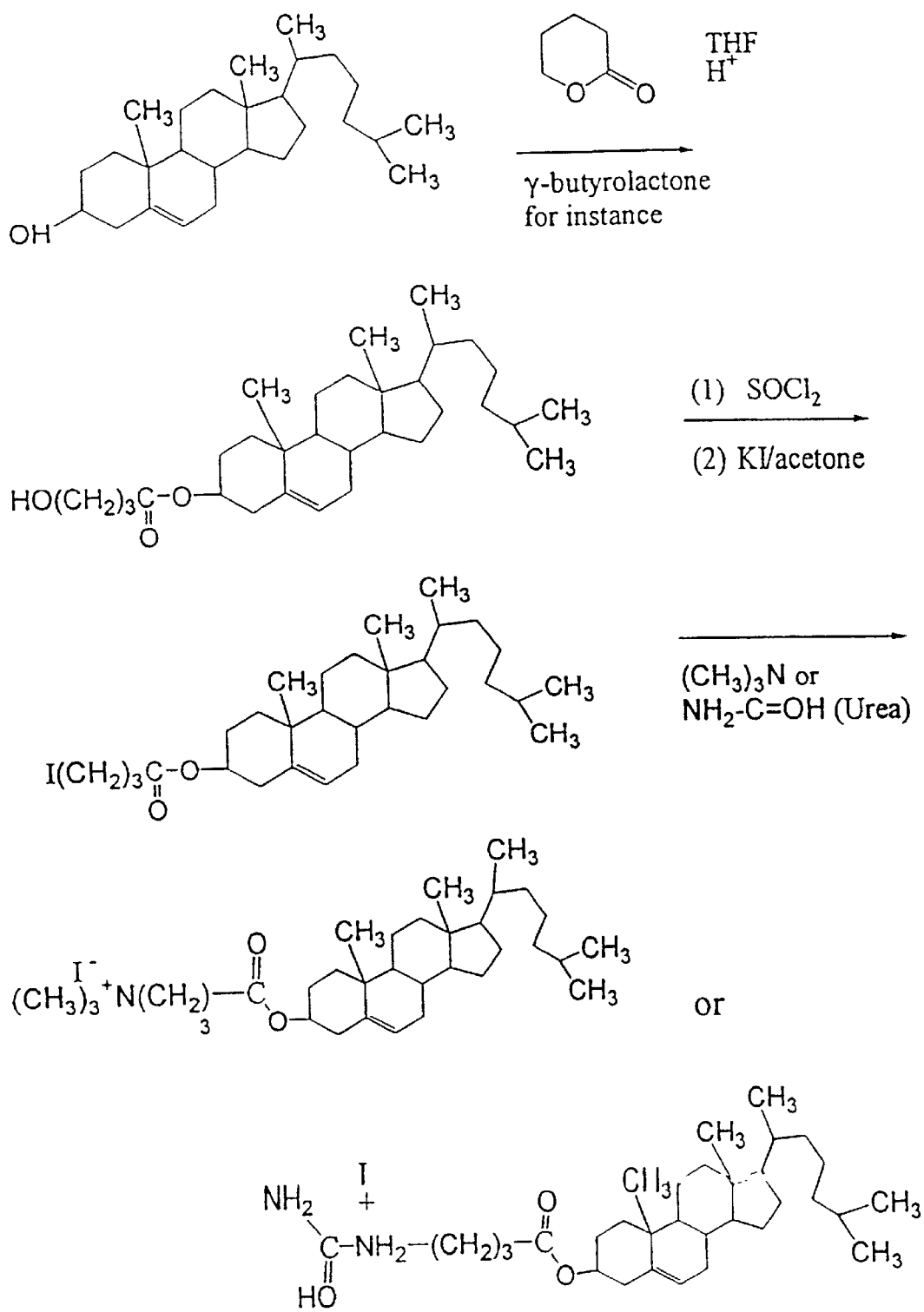
Figure 21F:
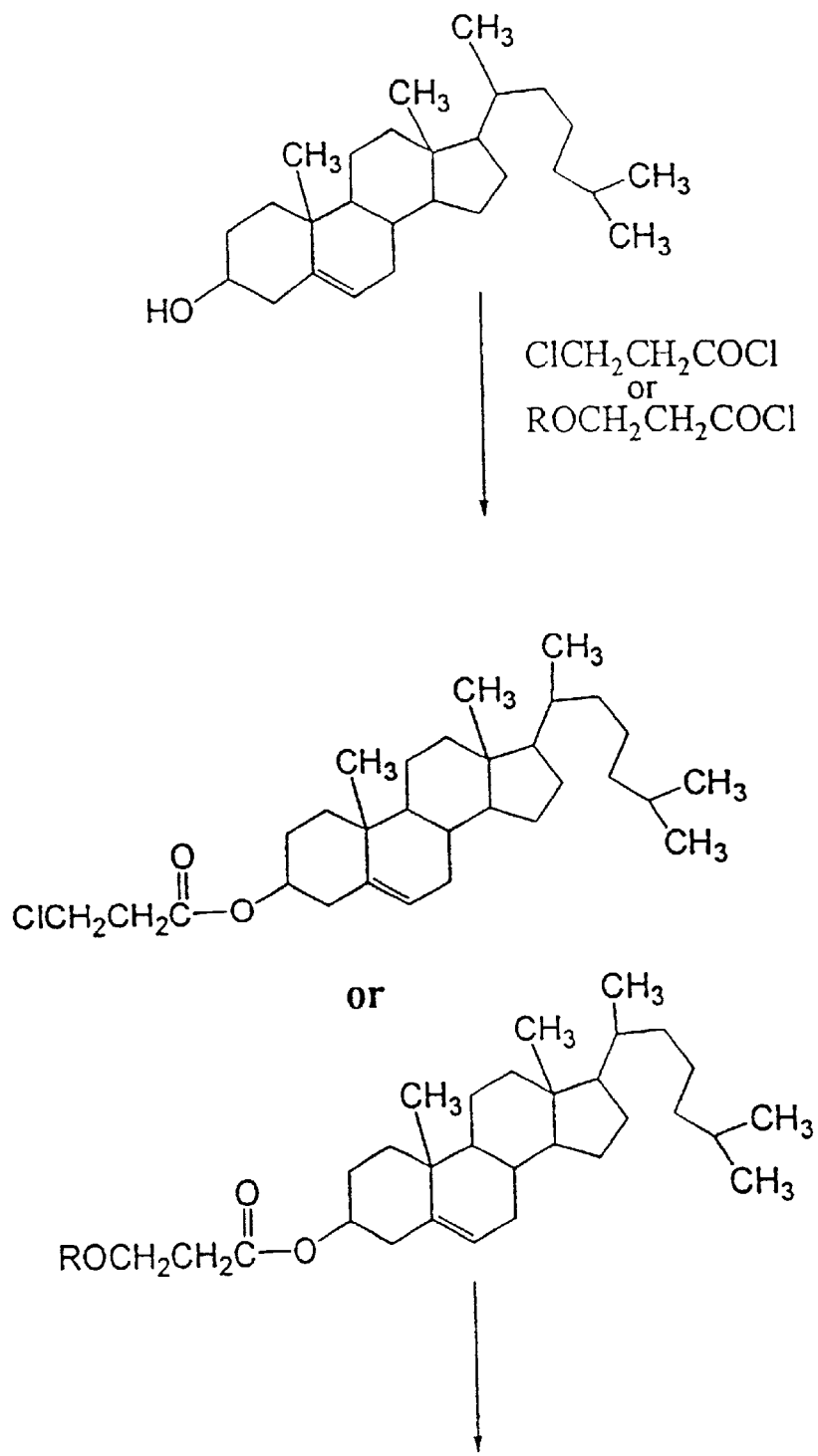

The arginine esters of the invention may be synthesized by known methods of synthesizing arginine esters. See, e.g., Guglielmi et al, Z. Physiol. Chem, 352, 1617–1630 (1971) and U.S. Pat. Nos. 5,364,884 and 4,308,280, the complete disclosures of which are incorporated herein by reference. These prior syntheses have been limited to short-chain alkyl and benzyl esters (six carbons or less), but the methods can be employed for synthesis of the arginine esters of the invention. For instance, the arginine esters may be prepared by the reaction of $R_2$-arginine with an alcohol, R1OH, in the presence of dry gaseous hydrogen chloride or using thionyl chloride (see FIGS. 20A–E). It has been found necessary to modify these syntheses by using sulfuric acid to catalyze the ester formation when more hydrophobic $R_1$ groups are used. In FIGS. 20D–E, arginine is first protected as in peptide synthetic methods and then deblocked after the formation of the ester. For a description of peptide synthetic methods, see Merrifield, J. Am. Chem. Soc, 85, 2149 (1963); Merrifield, in Chem. Polypeptides, pp. 335–361 (Katsoyannis and Panayotis eds. 1973); Davis et al, Biochem. Int'l, 10, 394–414 (1985); Stewart and Young, Solid Phase Peptide Synthesis (1969); U.S. Pat. No. 3,941,763; Finn et al, in The Proteins, 3rd ed, vol. 2, pp. 105–253 (1976); and Erickson et al, in The Proteins, 3rd ed, vol. 2, pp. 257–527 (1976). Arginine esters of the invention can also be synthesized using the conditions described in Mitsunobu, Synthesis 1981, 1–28, with $R_2$-arginine first being protected as in peptide synthetic methods and then deblocked after the formation of the ester (see FIGS. 20F–G). Other possible methods include the use of protected arginine derivatives and dicyclohexylcarbodiimide as the coupling agent and the use of Lewis acids, such as $BF_3$ etherate.

Also preferred are cationic cholesterol surfactants having the following formula:

$R_3$-L-CHOL

CHOL is the cholesterol nucleus, L is an ester, carbamate, carbonate or ketal linkage, $R_3$ is a linear, branched or cyclic hydrocarbon (e.g., alkyl, cyclic alkyl, aryl, or combinations thereof containing at least 1, preferably 1–15, most preferably 2–10, carbon atoms and also containing at least one amine group within the hydrocarbon, attached to the hydrocarbon (including at either end), or both. Preferred amine groups are quaternary amines and guanidinium groups. Most preferred is an arginine residue (—CH($NH_2$)—$CH_2$—$CH_2$—$CH_2$—NH—C ($NH_2$)=$NH_2^-$). $R_3$ may be substituted with neutral or other basic groups, including alkyls, aryls, amides, ester groups, and ether groups containing no more than 10 carbon atoms.

Figure 27:
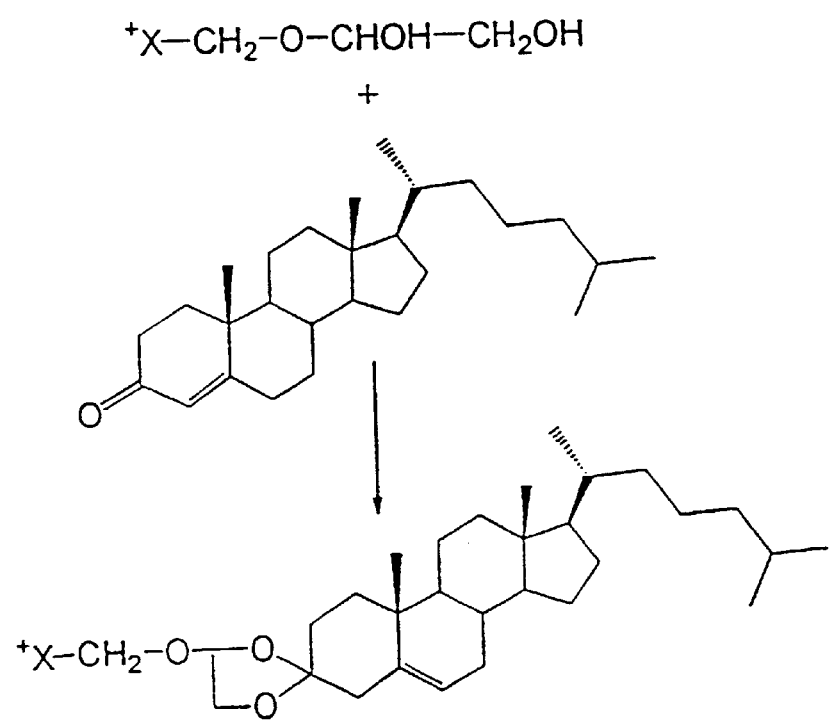
FIG. 27 illustrates a scheme for the synthesis of a ketal starting with 4-cholesten-3-one, X represents a cationic moiety.

The synthesis of arginine esters of cholesterol was described above (see FIGS. 20C–F and the description of these figures). These methods may be used to synthesize other esters of cholesterol. Additional methods of synthesizing esters of cholesterol and methods of synthesizing carbamates of cholesterol are schematically shown in FIGS. 21A–E. A method of synthesizing a ketal is illustrated in FIG. 27. Cholesterol carbonates can be synthesized by reacting cholesterol chloroformate with an amino alcohol (see Example 37).

The cationic surfactants of the invention can be used for the same purposes as prior art cationic surfactants. However, due to their much lower toxicity compared to the prior art cationic surfactants, the cationic surfactants of the invention are especially useful in pharmaceutical preparations and in other situations where cell survival is important. In particular, they can be used as the amphiphilic material in the methods and compositions described above.

In addition, the cationic surfactants of the invention can be used to deliver negatively charged compounds, such as acidic proteins and nucleic acids, into cells. This is accomplished by simply contacting the cells with a cationic surfactant of the invention and a compound desired to be delivered into the cell. The cells may be any type of eukaryotic or prokaryotic cell, but is preferably a mammalian cell, including human cells. The contacting may take place in vitro or in vivo.

The cationic surfactants are particularly suitable for transforming cells. The cells mad be transformed with any type of nucleic acid, including recombinant DNA molecules coding for a desired protein or polypeptide, recombinant DNA molecules coding for a desired antisense RNA or ribozyme, cloning vectors, expression vectors, viral vectors, plasmids, a transgene for producing transgenic animals or for gene therapy, antisense RNA, and ribozymes. The cells may be any type of cell, but are preferably microorganisms (e.g., bacteria and Yeast and other fungi) and animal (including human) cells (e.g., cell lines, pluripotent stem cells and fertilized embryos). The contacting may take place in vitro or in vivo.

To transform a cell, the cell is contacted with a nucleic acid and a surfactant according to the invention. Preferably, the nucleic acid and surfactant are combined and incubated together before contacting them with the cell. The time of incubation is that time sufficient to allow the nucleic acid and surfactant to complex. This time can be determined empirically. A time of about 45 minutes has been found to be sufficient for incubation of arginine dodecyl ester and a plasmid (see Example 39). The cell is contacted with the nucleic acid and surfactant for a time sufficient to allow the nucleic acid to be delivered into at least some of the cells. This time can also be determined empirically. A time of about 30 hours has been found to be sufficient when using the combination of arginine dodecyl ester and plasmid (see Example 39). Other conditions for contacting the cell with the nucleic acid and surfactant are known in the art or may be determined empirically.

The cationic surfactants of the invention mad be used alone to transform cells. Preferably, however, they are used in combination with helper lipids for transforming cells. The lipids may be any of those lipids known in the art to be useful in transforming cells, including dioleoyl phosphatidyl ethanolamine (DOPE) and cholesterol. The lipid should preferably promote fusion of the nucleic acid/surfactant/lipid complex with the membrane of the cell so that the nucleic acid may be transported into the interior of the cell.

To transform a cell, the cell is contacted with a nucleic acid, a surfactant according to the invention and a lipid. Preferably, the nucleic acid, surfactant and lipid are combined and incubated together before contacting them with the cell. The three may be combined simultaneously or sequentially (in any possible order of the three). The time of incubation is that time sufficient to allow the nucleic acid, surfactant and lipid to complex. This time can be determined empirically. The cell is contacted with the nucleic acid/surfactant/lipid for a time sufficient to allow the nucleic acid to be delivered into at least some of the cells. This time can also be determined empirically. Other conditions for contacting the cell with the nucleic acid, surfactant and lipid are known in the art or may be determined empirically.

The cationic surfactants of the invention may also be used, with or without helper lipids, in combination with other methods of transformation, such as electroporation. This may be particularly advantageous in transformation of plant cells.

After transformation in vitro, the cells may be cultured to produce a desired protein, polypeptide or RNA. Alternatively, the cells may be injected into an animal for gene therapy. In yet another alternative, the cells may be allowed to grow and differentiate into a transgenic animal or plant.

When the cells are to be transformed in vivo, the cationic surfactant or the lipid are preferably selected or modified so that they are targeted to selected cells to be transformed. For instance, the nucleic acid/surfactant combination could be incorporated into liposomes composed of the lipids. The liposomes could be targeted to particular cells by having an antibody specific for a molecule on the surface of the cells attached to the exterior of the liposomes.

The invention also provides a kit for delivering nucleic acids or other negatively charged compounds into cells. This kit comprises a container of a cationic surfactant of the invention. The kit may further comprise a container containing a nucleic acid, such as a cloning vector, expression vector or gene. The kit may further comprise other reagents and materials normally used for transforming cells, such as restriction enzymes, lipids, polymerase chain reaction reagents, and buffers.

In yet another important aspect of the present invention, it has, surprisingly, been found that the antisolvent precipitation method of the present invention may be operated to produce compositions having particularly desirable characteristics for sustained release of a pharmaceutical substance. The composition is characterized as including a pharmaceutical material, in the form of an HIP complex with an amphiphilic material, and a biocompatible polymer, with the biocompatible polymer being highly amorphous. The highly amorphous character of the polymer is particularly desirable for reducing immune system responses and, therefore, reducing the likelihood of causing significant inflammation during use by a human or other mammalian patient. Furthermore, the highly amorphous sustained-release composition also provides a desirably stable sustained release profile for release of the pharmaceutical substance, and typically with little or negligible burst effect. The highly amorphous sustained-release composition is particularly well suited for delivery of a pharmaceutical substance for sustained release by pulmonary delivery, subcutaneous placement, intraperitoneal placement and intraocular placement. The antisolvent process for making particles of highly amorphous sustained-release composition, the particles and composition so made, product forms incorporating the composition, and uses of the composition for administration to a mammalian patient for sustained-release purposes are all within the scope of the present invention.

The sustained-release composition includes the biocompatible polymer in a highly amorphous form. By highly amorphous, it is meant that the polymer is typically no more than about 25% crystalline. Most often, however, it will be desirable to keep the crystalline content of the biocompatible polymer as low as possible. Through careful control of operating parameters of the antisolvent precipitation process, the sustained-release composition may be prepared typically with the biocompatible polymer being no more than about 20% crystalline, preferably no more than about 15% crystalline, more preferably no more than about 10% crystalline, and even more preferably no more than about 5% crystalline. Particularly preferred is for the biocompatible polymer to be substantially entirely amorphous. As used herein, the crystalline content of the biocompatible polymer is as calculated based on x-ray defraction results, a technique well known in the art.

Careful control of the antisolvent precipitation process is important for making the highly amorphous sustained-release composition of the present invention with the desirable features noted above. In that regard, it is particularly important that the relative flows of the antisolvent fluid and the liquid feed, which includes a solvent having codissolved therein the biocompatible polymer and the HIP complex, be carefully controlled within certain ranges. In that regard, the volumetric ratio of the antisolvent fluid flow rate to the liquid feed flow rate should typically be larger than about 5, and more typically be in a range of from about 5 to about 100. Preferred amorphous characteristics, however, are more advantageously obtained with a volumetric ratio of antisolvent fluid flow rate to liquid feed flow rate of larger than about 15, more preferably larger than about 20, and even more preferably larger than about 25. A particularly preferred range for the volumetric ratio of antisolvent fluid flow rate to liquid feed flow rate for preparing the highly amorphous sustained-release composition is from about 10 to about 50, more particularly from about 15 to about 40, even more particularly from about 15 to about 30. and most particularly from about 20 to about 30.

In addition to controlling the relative flows of antisolvent fluid and liquid feed, the manner in which the antisolvent fluid and the liquid feed are contacted is also important. Although contacting mad be in counterflow, it has been found that concurrent flow, or co-flow, of the liquid feed and the antisolvent fluid generally produces a superior product.

Furthermore, control of the relative concentrations of the biocompatible polymer, the pharmaceutical substance and the amphiphilic material is an important consideration when making the highly amorphous sustained release composition. The relative amounts in the liquid feed of the HIP complex, comprised of the pharmaceutical substance and the amphiphilic material, and the biocompatible polymer will depend upon the specific application. The HIP complex may comprise about 0.5 weight percent or more of the total weight of the HIP complex and the biocompatible polymer, although amounts of greater than 1 weight percent are more common and greater than 5 weight percent are even more common. For the highly amorphous sustained-release composition of the present invention, however, it is generally desirable to include large relative amount of the HIP complex. Of the total weight of the HIP complex and the biocompatible polymer in the liquid feed, the HIP complex should typically comprise at least about 15 weight percent, preferably at least about 20 weight percent, more preferably at least about 25 weight percent, and even more preferably at least about 30 weight percent. Typically, however, the HIP complex content will be no larger than about 70 weight percent, preferably no larger than about 60 weight percent and more preferably no larger than about 50 weight percent.

Because the antisolvent precipitation process is extremely efficient at incorporating biocompatible polymer and HIP complex material into the manufactured product, the highly amorphous sustained-release composition will typically include a very high loading of the HIP complex material. Typically, the highly amorphous sustained-release composition will comprise the pharmaceutical substance and the amphiphilic material, in the form of a HIP complex, in an amount of at least about 15 weight percent, preferably at least about 20 weight percent, more preferably at least about 25 weight percent and even more preferably at least about 30 weight percent. At extremely high levels of loading with the HIP complex, the structural integrity of the composition may be compromised. Therefore, the HIP content will typically comprise no greater than about 70 weight percent of the composition, preferably no greater than about 60 weight percent of the composition and even more preferably no greater than about 50 weight percent of the composition. The biocompatible polymer typically makes up the balance of the composition.

The antisolvent precipitation process of manufacture, with carefully controlled operation, permits manufacture of the composition with the biocompatible polymer in a highly amorphous state and with a heavy loading of the HIP complex material. Furthermore, even though the composition is heavily loaded with the HIP complex material, the HIP complex material is, nevertheless, typically substantially homogeneously dispersed throughout a matrix of the polymer, such that the HIP complex and the biocompatible polymer are in an intimate mixture on a microscopic level. This intimate and homogeneous mixture is very important to achieving a stable release profile for release of the pharmaceutical substance from the sustained-release composition, as is the high level of loading of HIP complex material in the composition, as is discussed further below.

Also important is that the mass content of the amphiphilic material in the HIP complex material is typically as large as or larger than the mass content of the pharmaceutical substance. In that regard, the mass ratio of the amphiphilic material to the pharmaceutical substance in the composition will typically be larger than about 1, and is often in a range of about 1 to about 5 with a range of from about 2 to about 6 being preferred.

Even though the HIP complex includes a large proportion of amphiphilic material, the highly amorphous sustained-release composition is still heavily loaded with the pharmaceutical substance. The pharmaceutical substance typically comprises greater than about 5 weight percent of the composition, preferably greater than about 10 weight percent of the composition, more preferably greater than about 15 weight percent of the composition, and even more preferably greater than about 20 weight percent of the composition.

The antisolvent fluid for making the highly amorphous sustained-release composition will typically be carbon dioxide. It is preferred, however, that contacting of the antisolvent fluid and the liquid feed occur at subcritical conditions. Preferably, the temperature is subcritical with the reduced temperature, relative to the antisolvent fluid, preferably being in a range having a lower limit of about 0.75, more preferably about 0.85, even more preferably about 0.90, and most preferably about 0.95; and having an upper limit of about 0.95 and more preferably about 0.99 and even more preferably about 0.995. The reduced pressure, relative to the antisolvent fluid, is typically from about 0.5 to about 2. When carbon dioxide is the antisolvent fluid, the temperature during the antisolvent precipitation step is preferably in a range of from about 20° C. to about 30° C, and more preferably from about 20° C. to about 30° C.

For the highly amorphous sustained-release composition, the pharmaceutical substance may be any ionic pharmaceutical material and the amphiphilic material may be any compatible surfactant. Any of the pharmaceutical substances or amphiphilic materials described previously may be used. Preferred pharmaceutical substances include antibiotics, chemotherapeutic agents, and biologic agents. Preferred surfactants are AOT and SDS, as well as the cationic materials discussed previously. The solvent may be any suitable solvent, but often includes at least one of methylene chloride or trichloromethane.

The biocompatible polymer may be any polymer that may be processed in the antisolvent precipitation process to form the composition such that the polymer is in a highly amorphous state, as discussed previously. Most often, the biocompatible polymer is a biodegradable polymer, as discussed previously. When biodegradable, the polymer is most often hydrolytically degradable.

The biocompatible polymer, as it is commercially available, is frequently available only in a highly crystalline state. The polymer is, however, converted to a highly amorphous state during the antisolvent precipitation process. Preferred polymers for the biocompatible polymer are poly (lactic acid) homopolymers, including poly(l-lactic acid) and poly(d-lactic acid), poly(glycolic acid) homopolymer, polyanhydrides, such as poly(sebacic acid), poly (carboxyphenoxyhexane), polybutyrates and cellulosic polymers such as polyhydroxypropyl ethylcellulose. Any suitable molecular weight polymer may be used that is soluble in the solvent used for the liquid feed. Typical molecular weights are from about 2 kDa to about 500 kDa. In some instances, the biocompatible polymer could be a mixture of two or more different polymers or a copolymer of two or more different monomers. Also, it should be noted that, at least in the case of poly(lactic acid) and poly(glycolic acid) polymers, the polymers are typically not prepared from the acids, but from the cyclic diesters, lactide or glycoside, as the case may be. It should be recognized that, as used herein, poly(lactic acid) and poly(glycolic acid) polymers are inclusive of polymers prepared directly by condensation polymerization of the acids or by ring-opening polymerization of the cyclic diesters. The polymers made from ring-opening polymerization of lactide and glycolide are often referred to as polylactide and polyglycolide.

As produced in the antisolvent precipitation process, the highly amorphous sustained-release composition will be in particulate form. The particulate product may include particles of a variety of sizes and shapes. In that regard, any of the particulate products having particle characteristics as previously described may be made in the form of the highly amorphous sustained-release composition. For example, for pulmonary delivery applications, the particulate product preferably includes ultrafine particles of a spheroidal shape and with greater than about 90 weight percent of the particles being smaller than about 10 microns, more preferably smaller than about 6 microns, and even more preferably of a size of from about 1 micron to about 6 microns. Furthermore, the highly amorphous sustained-release composition may be made in the form of the fiber-like particles, or in the form of extremely fine particles of a size smaller than about 1 micron.

The highly amorphous, sustained-release composition may be incorporated into a variety of product forms for use. One product form is a macrostructure formed by agglomeration of particles of the particulate product prepared by the antisolvent precipitation method. The agglomeration is typically accomplished by compression. For example, cylinders, pellets, beads (e.g. spheroidal, ellipsoidal or other shape), discs and other macrostructures could be prepared from smaller particles. Preferred uses for such macrostructures are for subcutaneous and intraperitoneal surgical implantation. Depending upon the specific application, the macrostructure will typically have a mass in a range with a lower limit of about 0.01 gram, about 0.05 gram, about 0.1 gram, about 0.5 gram or about 1 gram and an upper limit of about 100 grams, about 50 grams, about 10 grams or about 1 gram. Any mass range having any one of the stated lower limits and any one of the stated upper limits is within the scope of the present invention, so long as the upper limit is larger than the lower limit. For example, for many applications, the macrostructure mass will be in a range of from about 0.05 to about 0.5 gram. To the extent that more of the pharmaceutical substance is desired than contained in a single macrostructure, then multiple macrostructures may be implanted together. For some applications, however, it will be desirable to have a very long sustained-release period, such as over a month or more. In these cases, the macrostructure will typically have a mass in a range of from about I to about 10 grams, although a larger mass may be desirable at times. Also, depending upon the specific application, the macrostructure will typically occupy a volume within a range having a lower limit of about 0.01 cubic centimeter. 0.05 cubic centimeter, 0.1 cubic centimeter, 0.5 cubic centimeter or 1 cubic centimeter; and an upper limit of about 100 cubic centimeters, about 50 cubic centimeters, about 10 cubic centimeters or about 1 cubic centimeter. Any volume range having any one of the stated lower limits and any one of the stated upper limits is within the scope of the present invention, so long as the upper limit is larger than the lower limit.

Another product form is a suspension of particles of the highly amorphous sustained-release composition in a liquid vehicle. Preferred uses for such suspensions are for placement by injection subcutaneously, intraperitoneally and intraocularly. Another preferred use for the liquid vehicle is for oral administration, for example, when uptake by gastrointestinal tissue is desired. For injection applications, the particles of the highly amorphous sustained-release composition should typically be smaller than about 50 microns, more preferably smaller than about 20 microns and most preferably smaller than about 10 microns. Particles of a size of from about 0.5 micron to about 10 microns are preferred for most injection applications. The liquid vehicle for the suspension may be an aqueous liquid or an organic liquid. When an aqueous liquid is used as the liquid vehicle, however, the particles of the highly amorphous sustained-release composition and the liquid vehicle are preferably mixed immediately before administration to a patient. Otherwise, significant release of the pharmaceutical substance into the aqueous liquid vehicle could occur prior to administration. The particles and the liquid vehicle could be provided in a kit including the particles in one container and the aqueous liquid in a second container for easy mixing prior to use. For most applications, however, it will be desirable to use an organic liquid vehicle that is premixed with the particles and stored for later use, without significant release of the pharmaceutical substance during storage. Examples of preferred organic liquid vehicles are ethanol and propylene glycol.

In another product form, a powder of the highly amorphous sustained-release composition could be packaged in a nebulizer or other aerosol-producing device for pulmonary delivery applications. Particle sizes for pulmonary delivery are preferably as discussed previously.

It should be noted that, in addition to being preferred for the highly amorphous sustained-release composition, the product forms of macrostructures, liquid suspensions and for aerosol generation are preferred even for compositions in which the biocompatible polymer may not have the desired highly amorphous character.

A major advantage of the highly amorphous sustained-release composition of the present invention is that, because of the highly amorphous character of the biocompatible polymer, the composition is less likely to cause an immune response when administered to a patient. More highly crystalline materials are more likely to cause an immune response and, therefore, accompanying inflammation.

Another significant advantage of the highly amorphous sustained-release composition of the present invention is that the composition exhibits very favorable release characteristics for sustained release of the pharmaceutical substance. This desirable result is believed to be related to the highly amorphous character of the composition and to the heavy loading of the composition with the HIP complex material. In that regard, when immersed in a phosphate buffer solution at a temperature of about 37° C. the highly amorphous sustained-release composition of the present invention typically exhibits a release profile for release of the pharmaceutical substance that plots as a single substantially straight line when plotted as cumulative pharmaceutical substance released versus the square root of time. The highly amorphous sustained-release composition therefore, exhibits only a single diffusion-controlled stage of release, and does not exhibit the occurrence of multiple diffusion-controlled stages of release, as has been reported for other amorphous compositions due to crystallization of polymer during use. Even though the release profile of the composition of the present invention exhibits substantially only a single stage of diffusion-controlled release, it should be recognized that anomalies in the release profile may be expected to occur at the very beginning of release. Also, during later stages of release, degradation of the polymer, in the case of a biodegradable polymer, will affect the release profile. For the highly amorphous sustained-release composition of the present invention, however, typically greater than about 70 percent, preferably greater than about 80 percent and more preferably greater than about 90 percent, of the pharmaceutical substance is released during the aforementioned single diffusion-controlled stage of release when immersed in the phosphate buffer solution at the noted temperature. The phosphate buffer solution, for comparison purposes, should typically be an aqueous solution including about 0.9 gram per liter of sodium chloride, about 0.144 gram per liter of monobasic potassium phosphate and about 0.795 gram per liter of dibasic sodium phosphate heptahydrate.

Yet another significant advantage of the highly amorphous sustained-release composition to the present invention is that it typically exhibits little, if any, significant burst effect during the initial stages of release of the pharmaceutical substance. In that regard, when immersed in the phosphate buffer solution, described previously, at a temperature of about 37° C, typically no more than about 15% of the pharmaceutical substance is released during the first 24 hours following immersion, preferably no more than about 10% and even more preferably no more than about 5%. Furthermore, the highly amorphous sustained-release composition will typically exhibit this low burst effect as manufactured by the antisolvent precipitation process. In some instances, however, it may be desirable to subject the composition to a post-manufacture wash with a buffer solution to remove pharmaceutical substance that may be adhering to the outside surface of particles. Such a wash may be accomplished, for example, by sonication for a short duration in a bath of buffer solution. Other methods for washing the particles are also possible.

The noted advantages of the highly amorphous sustained-release composition concerning pharmaceutical release characteristics are believed to be attributable, at least in part, to the highly amorphous character of the composition and to the heavy loading of the composition with the HIP complex. The amorphous character of the composition is desirable because sustained-release composition made with highly crystalline polymers often have pharmaceutical release rates that are too slow. Furthermore, the amorphous character of the sustained-release composition of the present invention appears to be retained for at least a significant time during release. The initial formation of the highly amorphous biocompatible polymer in the composition and the apparent maintenance of a highly amorphous character during use are believed to be due, at least in pr to heavy loading with the HIP complex material. Because both the HIP complex material and the biocompatible polymer both typically have a high hydrophobicity, they typically form a homogeneous and intimate mixture which may retard crystallization of the polymer during use.

Still a further significant advantage of the highly amorphous sustained-release composition of the present invention is that it typically includes only very small quantities of residual organic solvent. In that regard, residual organic solvent levels, as manufactured, are typically less than about 50 parts per million by weight, preferably less than about 25 parts per million by weight, and even more preferably less than about 10 parts per million by weight. Frequently, residual organic solvent levels are less than about 3 parts per million by weight. To maintain residual organic solvent levels at an extremely low level, the antisolvent precipitation process is preferably conducted such that after the particles have been precipitated in a reactor vessel, they are retained in the reactor vessel and flushed with a volume of substantially pure antisolvent fluid for a sufficient time to reduce the residual solvent content to the desired level. A post-precipitation flush with a volume of substantially pure antisolvent fluid should preferably include at lease about one reactor volume of antisolvent fluid, with a flush of at least about two times the reactor volume being more preferred.

One particularly preferred embodiment for the highly amorphous sustained-release composition of the present invention includes poly(l-lactic acid) as the biocompatible polymer. When making a composition with poly(-lactic acid), the preferred solvent is either methylene chloride or trichloromethane, although ethyl acetate may also be used if the poly (1-lactic acid) has been suitably end-capped or otherwise modified for enhanced solubility.

The pharmaceutical substance may be any of the pharmaceutical substances previously listed. In one preferred embodiment of the present invention, however, the pharmaceutical substance in the highly amorphous sustained-release composition is isoniazid, which is preferably in the form of an ion pair with AOT. This composition is particularly preferred for treating tuberculosis. The preferred biocompatible polymer is poly(1-lactic acid). The preferred method for administering the highly amorphous sustained-release composition with isoniazid is via subcutaneous placement, typically by implantation of a macrostructure, as previously described, comprised of agglomerated particles made by the antisolvent precipitation process.

In another aspect of the present invention, the antisolvent precipitation process may be used to make particles including a highly amorphous biocompatible polymer, even in the absence of a HIP complex material. For example, a pharmaceutical substance that is not in an HIP complex form could be suspended in or, for a few pharmaceuticals, co-dissolved in a solvent containing the polymer. Alternatively particles made by the antisolvent precipitation process could be of substantially pure biocompatible polymer. The preferred processing conditions with respect to flow rates, conditions for contacting the solvent and antisolvent, pressure, temperature, antisolvent fluids, solvents and biocompatible polymers are as previously described for the highly amorphous sustained-release composition including an HIP material. Compositions without the HIP complex material, however, are not preferred because the presence of the HIP complex material, as previously discussed, significantly enhances the properties of the composition for use in sustained-release applications. In these embodiments, the biocompatible polymer in the particles typically preferably is not more than about 25% crystalline, preferably not more than about 20 weight percent, more preferably not more than about 15% crystalline, even more preferably not more than about 10% crystalline, and most preferably not more than about 5% crystalline.

The invention will now be further described with reference to the following non-limiting examples.

EXAMPLES

The methods used for measuring apparent partitioning coefficients are described in Example 1. The measurement of the behavior of the Gly-Phe-NH$_2$:SDS complex is described in Example 2. The behavior of the 8-Argvasopressin:SDS complex, leuprolide:SDS complex, neurotensin:SDS complex, and bradykinin:SDS complex are described in Example 3. The behavior of the insulin:SDS complex is described in Example 4. The dissolution of the insulin:SDS complex as a function of the organic solvent is described in Example 5. Further behavior of the leuprolide:SDS complex is described in Example 6 Example 7 describes the CD spectrum of the insulin:SDS complex. Example 8 describes the thermal stability of the insulin:SDS complex. Example 9 describes the behavior of other large proteins with SDS, specifically, human growth hormone. The behavior of bovine pancreatic trypsin inhibitor with SDS is described in Example 10, and Example 11 describes the behavior of human serum albumin with SDS. The melting point of the SDS:insulin HIP complex was studied (Example 12).

Example 13 describes a method for forming a fine HIP complex suspension suitable for pulmonary delivery. Example 14 describes a method for achieving uniform distribution of a protein throughout a hydrophobic polymer suitable for use as an injectable implant. Example 15 describes the use of the HIP complex for improved storage of proteins. The use of protein precipitation in the HIP complex for protein purification is described in Example 16. A method of administering a protein dissolved as an HIP complex in organic solvent is described in Example 17. Example 18 describes the preparation of a drug with reduced bitter taste.

Examples 19–29 demonstrate batch preparation of particles using gas antisolvent precipitate. Examples 30–32 demonstrate continuous preparation of particles using gas antisolvent precipitation.

Examples 33–40 describe the preparation, characterization and use of cationic surfactants of the invention.

Example 1

Measurement of Apparent Partition Coefficients

The relative solubilities in two phases is given in terms of an apparent partition coefficient. The apparent partition coefficient is defined as the ratio of the equilibrium concentration in an organic phase to that in an aqueous phase. The actual value of the apparent partition coefficient, P, is dependent on the two solvent systems employed. In all cases herein described, the organic phase is 1-octanol and the aqueous phase is water alone or with a minimal amount of HCl added.

Apparent partition coefficients were measured by dissolving a peptide in 1.25 ml of an aqueous solution. Before SDS addition, the pH was measured on a Beckman pH meter. Upon addition of an SDS solution, the solutions turned cloudy and a precipitate formed immediately. An equal volume of 1-octanol was added and the mixtures agitated, and then left undisturbed for several hours. Prior to analysis, the tubes were spun for 10 minutes at 4000 g. Each layer was removed and the absorbance measured on a Beckman DU-64 UV-visible spectrophotometer using I cm quartz cells. All apparent partition coefficients were corrected for changes in pH with differing SDS concentrations.

Results are described as logarithms of the apparent partition coefficient. A log P value of 0 means that the compound is equally soluble in water and the organic phase. A positive log P value means the peptide is more soluble in the organic phase than in water and a negative log P values indicate a greater aqueous solubility than in the organic solvent. All of the log P values reported herein have been corrected for slight changes in solubility with pH.

Example 2

Apparent Partitioning Coefficient for GlyPhe-NH$_2$

The logarithm of the apparent water/1-octanol partition coefficients for Gly-Phe-NH$_2$ Gly-Phe amid. 0.6 mg/ml, pH about 5) and Gly-Phe (0.6 mg/ml at pH 7 and pH 3) as a function of SDS to peptide ratio are shown in FIG. 1. Apparent partition coefficients were measured as described in Example 1.

In order for HIP to occur, the polypeptide must contain at least one basic group (either a lysine or arginine side chain or a free N-terminal amino group). Gly-Phe-NH, contains a single basic group, and at pH 7 forms a 1:1 complex with SDS. The complex precipitates from aqueous solution, but readily partitions into 1-octanol, as shown in FIG. 1. For Gly-Phe itself, which exists in a zwitterionic form at neutral pH, a complex with SDS is formed with difficulty, and little enhancement of the partition coefficient is observed. However, by lowering the pH to less than 4, the carboxylate group of Gly-Phe becomes protonated, leaving the molecule with an overall positive charge and again a hydrophobic ion pair can be formed. Partitioning of GlyPhe at pH 3 mirrors the marked increase seen for Gly-PheNH$_2$. Therefore, even for acidic peptides, lowering the pH may permit hydrophobic ion pair complexes to be formed.

Example 3

Behavior of Protein:SDS Complexes

Figure 2:
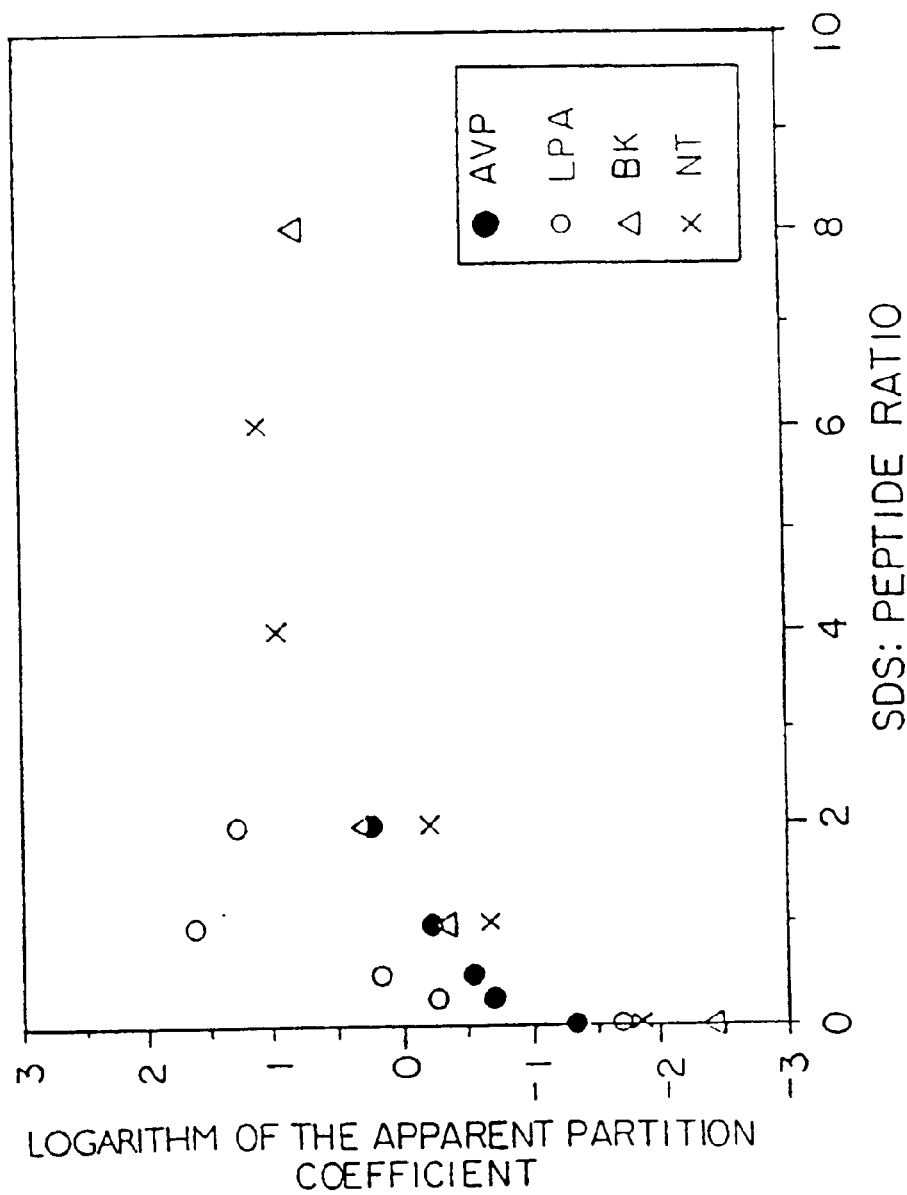
FIG. 2 shows the log of the apparent partition coefficient for 8-Arg-vasopressin (AVP).

The logarithms of the apparent water/1-octanol partition coefficient for AVP (0.49 mg/ml, pH 5), leuprolide (LPA) (0.5 mg/ml, pH 6), neurotensin (NT) (0.y mg/ml, pH x), and bradykinin (BK) (0.y mg/ml, pH x) are shown in FIG. 2. Apparent partition coefficients were measured as described in Example 1.

Peptides larger than Gly-Phe-NH$_2$ can interact with SDS to form HIP-complexes with enhanced solubility in organic solvents. AVP is a nonapeptide hormone which controls water and salt elimination in the body. It contains two basic groups, the N-terminal amino group and the guanidinium side chain of Arg$^8$, and no acidic groups. Stoichiometric addition of SDS produces a precipitate from an aqueous solution (pH 7) which readily partitions into a 1-octanol (FIG. 2). At a mole ratio of 2:1 (SDS:peptide), the solubility in 1-octanol actually exceeds the solubility in water by more than tenfold (i.e., log P>1). Overall, the apparent partition coefficient for AVP was increased by nearly four orders of magnitude.

Example 4

Behavior of Insulin:SDS Complex

Figure 3:
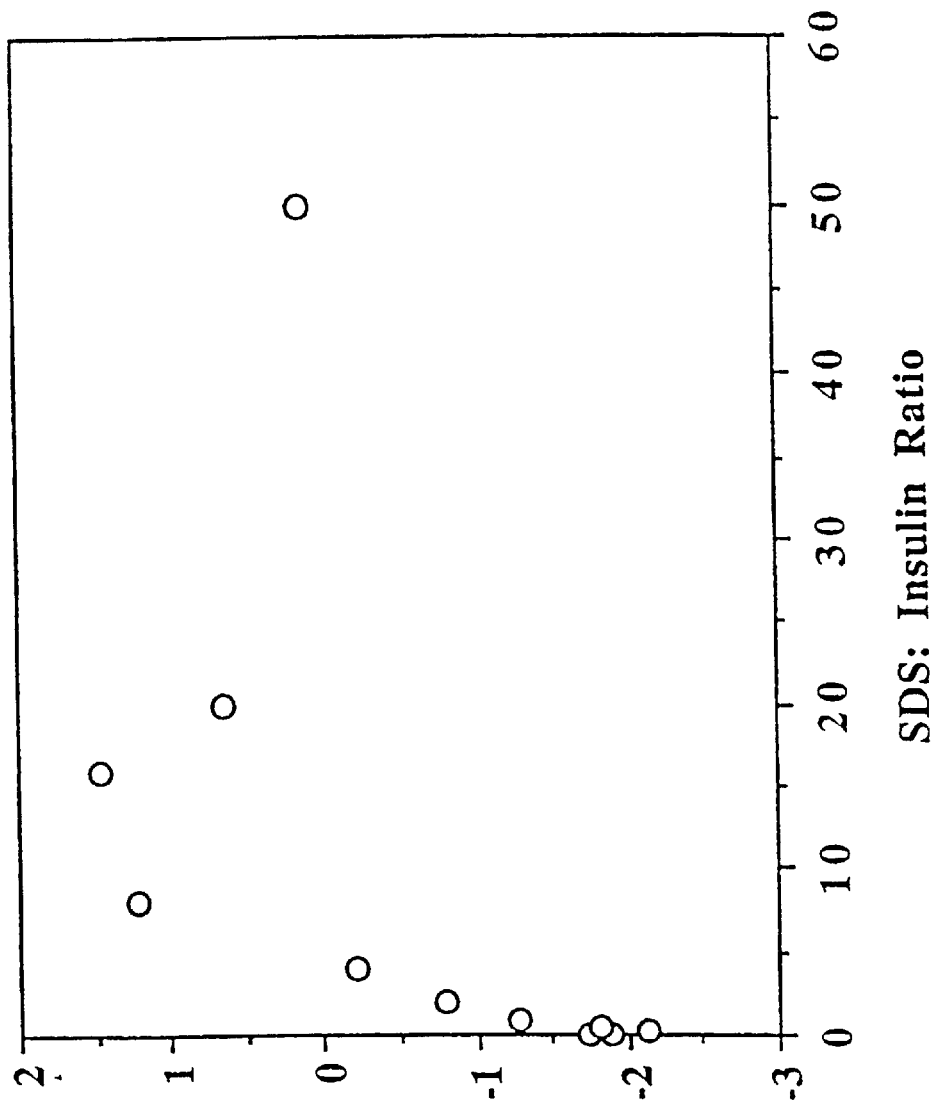
FIG. 3 shows the log of the apparent partition coefficient for insulin.

The logarithm of the apparent partition coefficient of insulin as a function of SDS ratio is shown in FIG. 3.

Polypeptides which contain both acidic and basic groups can also form hydrophobic ion pairs. Insulin contains six basic groups (one Arg, one Lys, two His, and two F-terminal amino groups) and four acidic groups. By lowering the pH to 2.5. all of the acidic groups (which are carboxylic acids) become protonated and the only remaining charges are due to the basic functional groups, producing an overall charge of +6.

The solubility of insulin is altered dramatically upon addition of stoichiometric amounts of SDS (FIG. 3). The solubility of an insulin-SDS complex approaches 1 mg/ml (0.17 mM) in 1-octanol, and its apparent partition coefficient increases by nearly four orders of magnitude. At higher SDS concentrations, the apparent partition coefficient decreases, because the solubility of insulin in water increases again, presumably due to micelle formation.

Example 5

Dissolution of Insulin-SDS Complexes as a Function of the Organic Solvent

Dissolution of insulin-SDS complexes in other solvents was investigated as well (Table 1). Precipitates of SDS-insulin complexes were isolated and added to various organic solvents. Some degree of polarity appears to be necessary to obtain measurable solubility in the organic phase, as partitioning into chlorocarbons ($CH_2Cl_2$ 1-chlorooctane, and $CCl_4$) and alkanes (mineral oil, hexane) could not be detected using UV-visible absorption spectroscopy. Besides alcohols. SDS-insulin complexes are soluble in N-methylpyrrolidone (NMP), trimethylphosphate (TRIP), polyethylene glycol, ethanol, and t-butanol.

TABLE 1

PARTITIONING OF INSULIN INTO NON-AQUEOUS SOLVENTS

| Organic Solvent | Log P | Apparent Sol. (mg/ml) |
|---|---|---|
| 1-octanol | $\geq 1.2$ | $\geq 1.0$ |
| $CCl_4$ | not detectable | insoluble |
| Mineral Oil | not detectable | insoluble |
| $CH_2Cl_2$ | not detectable | insoluble |
| Dimethoxyethane | not detectable | not determined |
| Hexane | not detectable | insoluble |
| 1-Chlorooctane | not detectable | insoluble |
| THF | miscible | not determined |
| Acetone | miscible | not determined |
| Ether | not detectable | insoluble |
| DMF | not determined | $\geq 1.0$ |
| NMP | miscible | $\geq 1.0$ |
| Ethyl acetate | miscible | insoluble |
| PEG 400 | miscible | $\geq 0.2$ |
| Trimethyl phosphate | miscible | $\geq 0.15$ |
| Ethanol | miscible | $\geq 1.0$ |
| i-Propanol | miscible | $\geq 1.0$ |
| Methanol | miscible | $\geq 1.0$ |
| Propylene Glycol | miscible | $\geq 0.5$ |
| TMP | miscible | $\geq 0.2$ |
| Trifluoroethanol | miscible | $\geq 0.5$ |

Example 6

Behavior of Leuprolide:SDS Complex

Leuprolide acetate is a luteinizing hormone releasing hormone (LHRH) agonist used in the treatment of endometriosis. It contains 9 amino acid residues and two basic functionalities (a histidine and an arginine group). Both termini are blocked. Stoichiometric amounts of SDS were added to an aqueous solution of leuprolide (0 and 0.5 mg/ml, pH 6.0), resulting in formation of a precipitate. The apparent partition coefficient of the SDS-leuprolid complex (FIG. 2) exhibited a log P into 1-octanol greater than 1.0.

Example 7

CD Spectrometry of the SDS-Insulin Complex

Two important considerations for proteins dissolved in non-aqueous solvents are whether native structures are retained and whether the material can be extracted back into an aqueous phase. The secondary composition of a 6:1 SDS-insulin complex dissolved in neat 1-octanol at 5° C. is shown in FIG. 3. The insulin concentration was 61 ug/ml.

CD spectra were recorded on an Aviv 62DS spectrophotometer equipped with a thermoelectric temperature unit. All temperatures were measured ±0.2° C. Samples were placed in strain-free quartz cells (pathlength of 1 mm) and spectra obtained taking data every 0.25 nm using a three second averaging time, and having a spectral bandwidth of 1 nm.

Analysis of the CD spectrum, using an algorithm based on the methods of Johnson (1990) Genetics 7:205–214 and van Stoklom g al. (1990) Anal. Biochem. 191:110–118, indicates that the alpha-helix content of insulin in octanol is 57%, similar to that found for insulin in aqueous solution (57%) (Melberg and Johnson (1990) Genetics 8:280–286) and in the solid state by x-ray crystallography (53%/) (Baker et al. (1988) Phil. Trans. R Soc. London B319, 369–456). The spectra are slightly more intense than those reported for insulin in water (Pocker and Biswas (1980) Biochemistry 19:5043–5049; Melberg and Johnson (1990) supra; Brems et al. (1990) Biochemistry 22:9289–9293). The relative intensity of the 222 nm band to the 208 nm band is similar to that observed for insulin at high concentrations (Pocker and Biswas (1980) supra). This represent the first example of native-like structure in a protein dissolved in a neat organic solvent.

Figure 4:
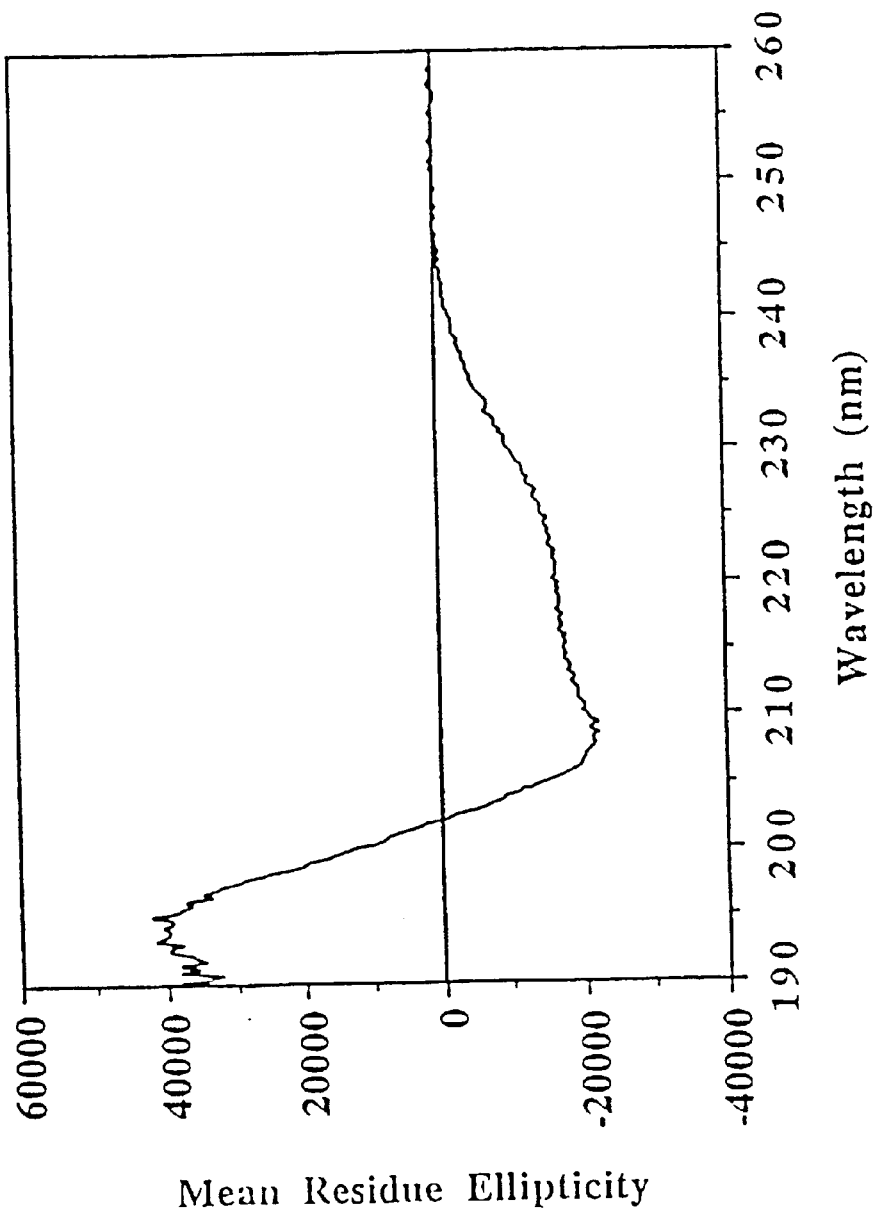
FIG. 4 shows the CD spectra of a 6:1 SDS-insulin complex in 1-octanol.
Figure 5:
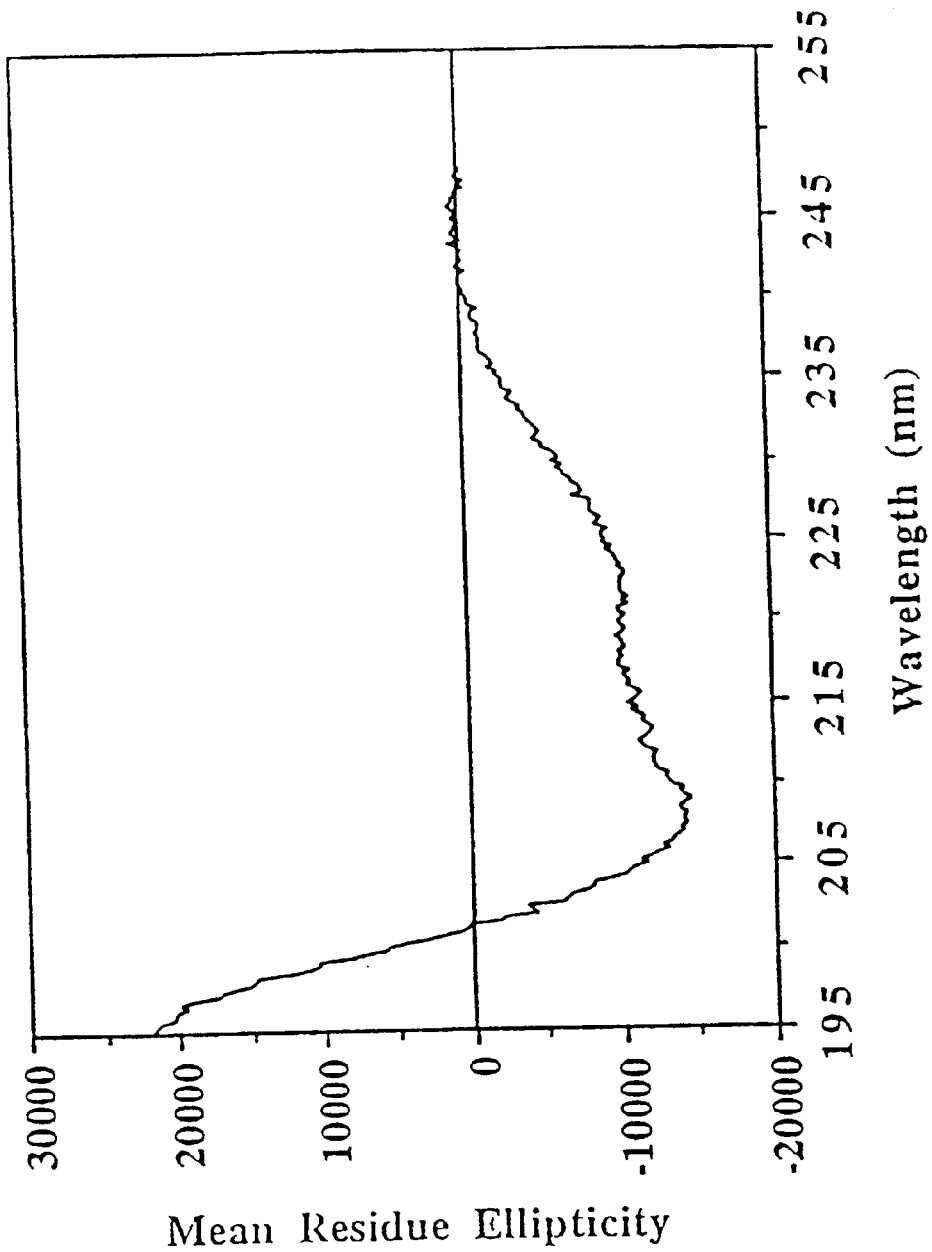
FIG. 5 shows the CD spectra of insulin extracted from 1-octanol using an aqueous solution of 0.10 M HCl.

FIG. 4 shows the far ultraviolet CD spectrum of insulin extracted from 1-octanol into an aqueous solution of 0.10 M HCl. The pathlength was 1 mm, the sample concentration 53 ug/ml, and the sample temperature 5° C. Upon shaking an octanol solution of insulin with an aqueous solution containing 0.10 M HCl, insulin can be extracted back into the aqueous phase, presumably due to replacement of the SDS counterion with chloride. Lower HCl concentrations did not affect extraction of insulin from 1-octanol. Examination of the CD spectrum of the redissolved material (FIG. 4) indicates an overall structure similar to that of native insulin.

Example 8

Increased Thermal Stability of the SDS:Insulin Complex

Figure 6:
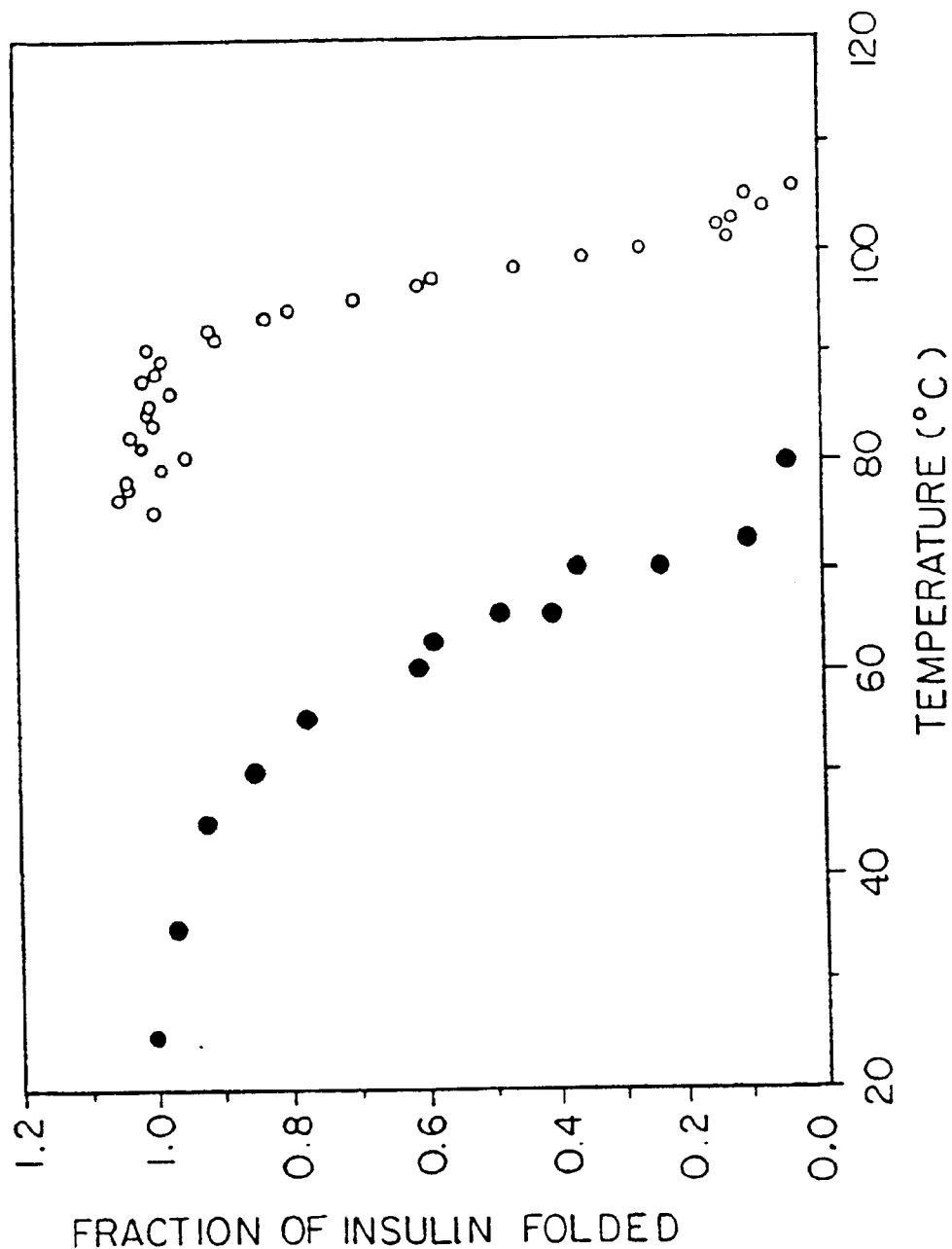
FIG. 6 shows the effect of temperature on the denaturation of insulin dissolved in 1-octanol.
Figure 9:
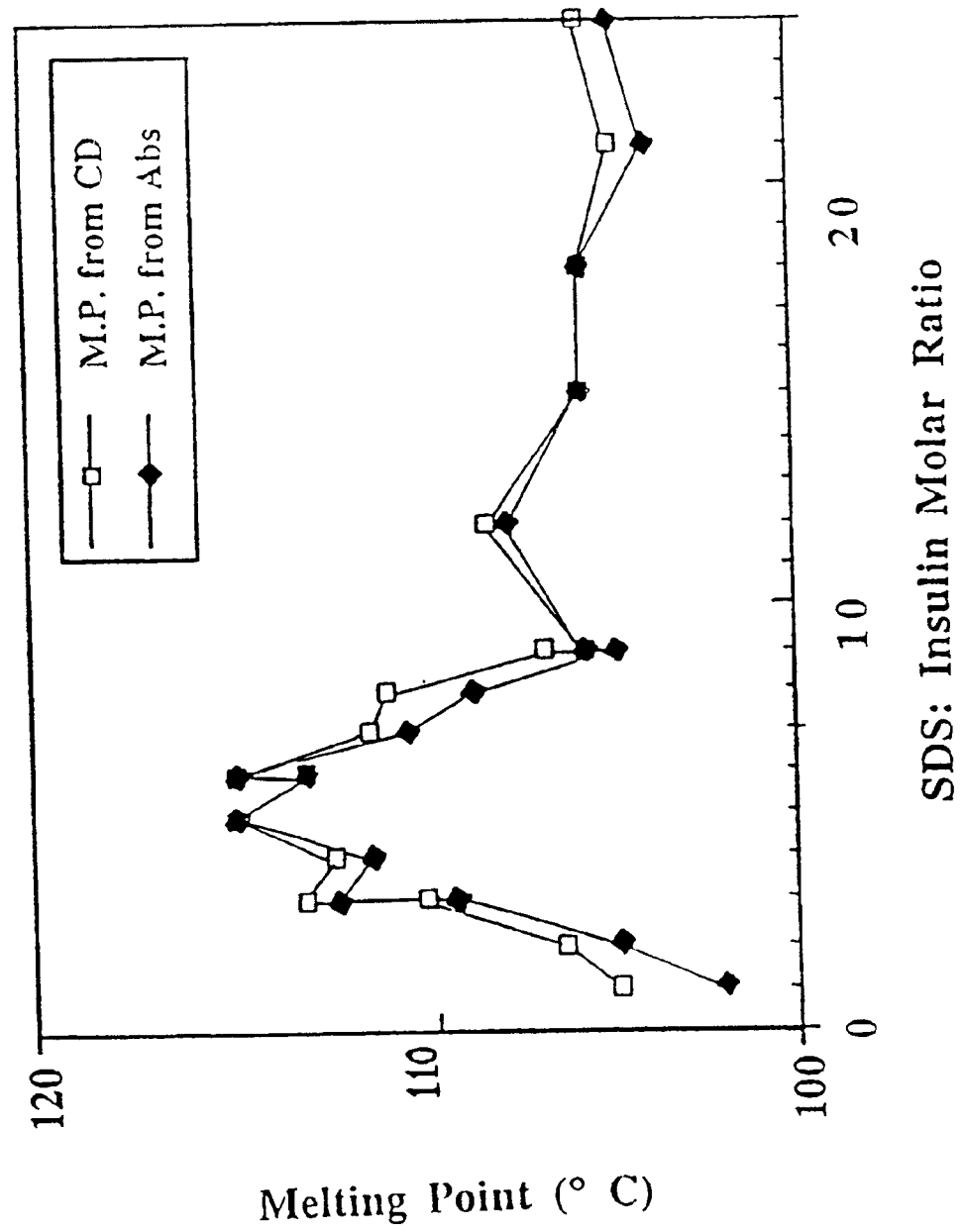
FIG. 9 shows the melting point of the SDS:insulin HIP complex as a function of the molar ratio of SDS to insulin.

The stability of insulin to thermal denaturation is difficult to assess as chemical degradation rates are rapid at elevated temperatures (Ettinger and Timasheff (1971) Biochemistry 1:824–831). In aqueous solution, the thermal denaturation of insulin occurs at a $T_m$ of about 65° C. [define $T_m$. The $T_m$ of insulin in 1-octanol has been measured, following molar ellipticity at 222 nm, to occur at 98° C. (FIG. 6), which is more than 30 degrees above that observed in water. This observation supports the conclusion that proteins dissolved in organic solvents demonstrate exceptional thermal stability. Although prior reports have observed that proteins suspended in organic solvents exhibit increased chemical stability due to lack of water (Ahem and Klibanov (1987) references), the present disclosure is the first report to find increased protein stability of the SDS:protein complex in organic solvent with respect to denaturation. Furthermore, as shown in FIG. 9, the SDS-insulin complex appears to maintain its native structure in 1-octanol, even after prolonged heating at 70° C. for more than 1 hour.

Example 9

Behavior of Larger Proteins Complexed with SDS

Larger proteins can also form complexes with SDS. At pH 7.8, the aqueous solubility of human growth hormone (hGH) was not affected by addition of SDS, even at ratios of 100:1. However, at pH2.hGH precipitates from aqueous solution at the ratios ranging from 10:1 to 40:1. At higher SDS concentrations, hGH redissolves, presumably via micellar solubilization. The hGH precipitate was not found to be soluble in 1-octanol, as determined by spectrophotometric assay, however, it was easily suspended in water and various oils, such as olive oil.

Example 10

Behavior of Bovine Pancreatic Trypsin Inhibitor Complexed with SDS

Figure 7:
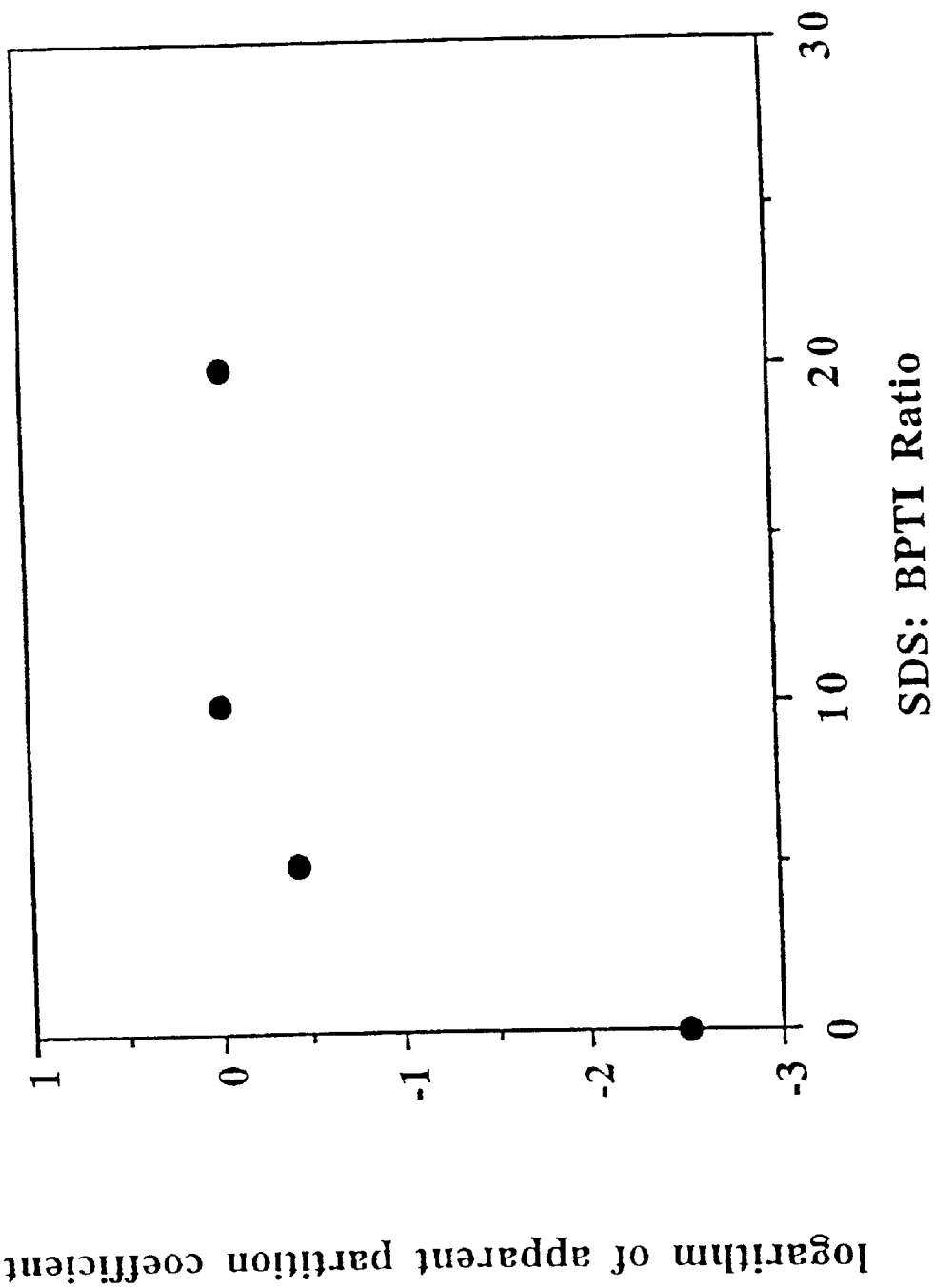
FIG. 7 shows the logarithm of the apparent partition coefficient of bovine pancreatic trypsin inhibitor (BPTI) from pH 4 water into 1-octanol.

Other proteins can also form complexes with SDS. Bovine pancreatic trypsin inhibitor (BPTI) is a small basic protein (MW 5900) with a well defined and stable structure (Wlodawer et. al. (1984) J. Mol. Biol. 180:301–329, and (1987) J. Mol. Biol. 193:145–156). At pH4, it partitions into 1-octanol upon addition of SDS (FIG. 7). As with insulin, the structure is maintained (data and shown) and the SDS-BPTI complex is soluble in other solvents as well, such as NMP and trimethyl phosphate (TMP). In TMP, the globular structure is compromised, as determined by CD spectroscopy. Apparently, TMP is a strong enough solvent to displace water from the hydration sphere and destabilize the structure of BPTI. This mechanism of protein denaturation has been described in detail by Arakawa and Timasheff (1982) Biochemistry 21:6536–6544. and (1982) Biochemistry 21:6545–6552.

Example 11

Behavior of HIP Complex Formation with Human Serum Albumin

Figure 8:
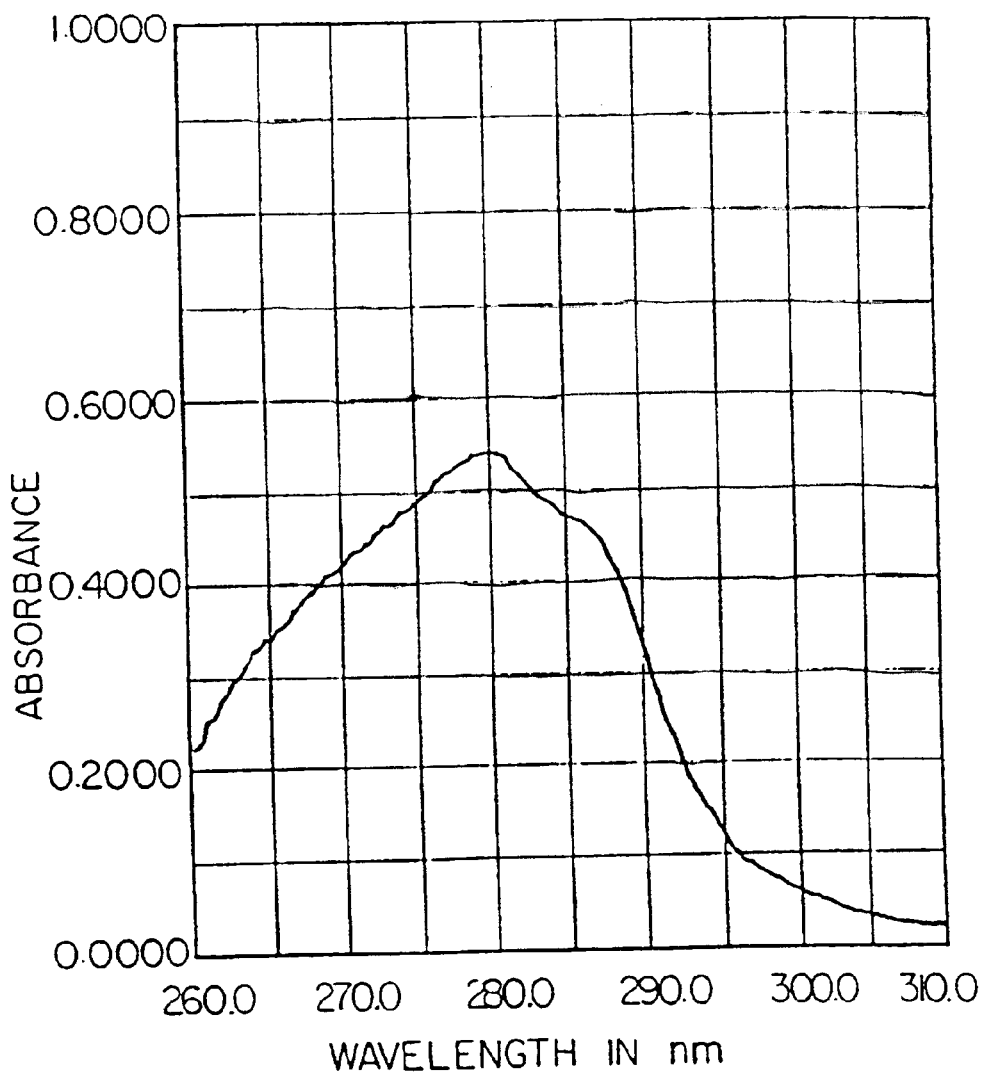
FIG. 8 shows the UV-visible absorption spectrum of human serum albumin (HSA) in NMP (50:1 SDS to HSA ratio).

Stoichiometric addition of SDS to human serum albumin (HSA) (MW 68 kD) produces precipitates as a hydrophobic ion pair complex is formed. While partitioning into 1-octanol could not be detected by UV-visible absorption spectroscopy, the SDS-HSA complex was found to be soluble in NMP (FIG. 8), yielding solutions of concentrations greater than 1 mg/ml (pathlength=1 cm, sample temperature=27° C.). Without SDS, the solubility of HSA in NMP is less than 0.03 mg/ml.

Example 12

Melting Point of SDS:Insulin Complex

The melting point (NIP) of SDS:insulin ion pairs in 1-octanol was studied at SDS:insulin ratio ranging from 1:1 to 1:24.

Insulin at 1 mg/ml in 0.005 N HCl was prepared containing SDS at 1, 2, 3, 4, 5, 6, 7, 8, 9, 12, 15, 18, 21 and 24 moles of SDS per mole of insulin. Equal volumes of octanol were added to each SDS:insulin solution to partition the insulin into the octanol phase. The concentration of the SDS:insulin complex extracted into the octanol was estimated by its absorbance at 278 nm and the solution diluted to 200 ug/ml. The melting point of the various insulin in octanol solutions was then determined with an AVIV 62DS circular dichroism spectrometer. Both circular dichroism (CD) signal and light scattering (as measured by changes in absorbance) were measured at 222 nm and the melting point determined by an inflection point in the measured scan.

FIG. 9 shows the graph of melting point as a function of SDS:insulin molar ratios, with an apparent maximum at 6:1 molar ratio and a melting point of about 116° C. The molar ratio of 6:1 is also the stoichiometric ratio and show the highest thermal stability for insulin in octanol.

Figure 10:
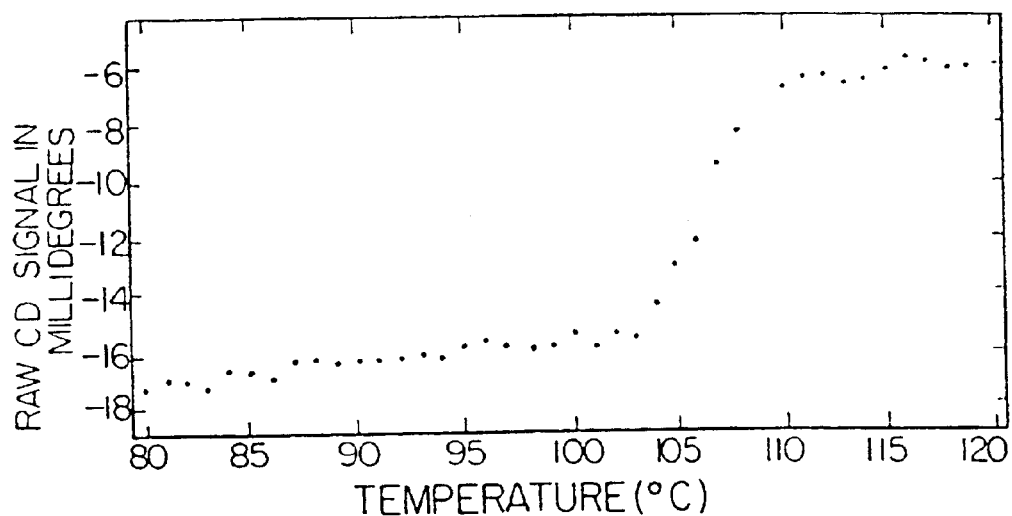
FIG. 10 shows a CD scan for a 9:1 SDS:insulin molar ratio at 222 nm as a function of temperature.
Figure 11:
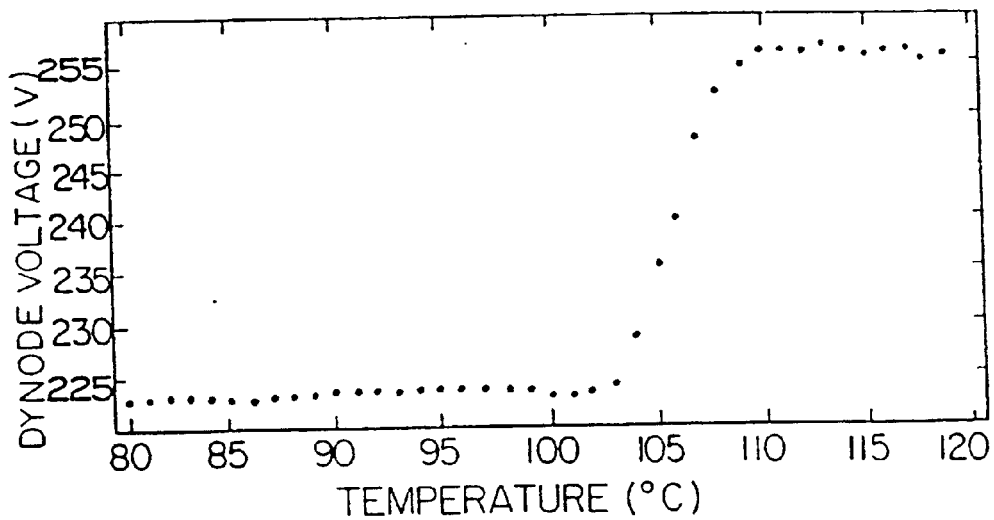
FIG. 11 shows an absorbance scan for a 9:1 SDS:insulin molar ratio at 222 nm as a function of temperature.

FIG. 10 shows a typical CD scan at 222 nm as a function of temperature. A melting point of 106° C. was determined by the maxima of the first derivative of the pictured data. FIG. 11 shows a typical absorbance scan at 222 nm as a function of temperature and effectively mimics the CD scan, showing a melting point of 106° C.

Example 13

Formation of a Fine Suspension HIP Complex for Pulmonary Delivery

For the formation of particles for pulmonary delivery, a protein solution is stirred vigorously using a homogenizer. SDS is added dropwise to the agitated solution. Particles in the 2–10 micron range are obtained. These particles arc separated from the mixture by centrifugation or filtration. The particles are then suspended in a mixture of Freone® 11 and 12, such than when placed in a meter dose inhaler, a therapeutic amount of protein is delivered on each actuation.

Example 14

Uniform Distribution of Protein Throughout a Hydrophobic Polymer for Use in an Injectable Implant The biodegradable polymer consisting of a 50:50 mixture of poly-lactic acid and poly-glycolic acid is dissolved in a volatile organic solvent, such as N-methyl-pyrrolidone (NMP). An appropriate amount of an HIP-protein complex such as insulin-SDS (0.5%–5.0% by weight relative to the polymer) is dissolved in the same solvent. The two solutions are mixed and stirred for one hour. After the mixing is complete, the solvent is removed by evaporation. This is done in a mold to form an implant, or by a spray drying procedure to form small uniform particles for injection. The resulting solid material can also be ground to a powder and formulated as an injectable suspension. The protein is released from these systems as the polymer biodegrades and the HIP complex hydrolyses.

Example 15

Use of HIP Complex Formation for Protein Storage

The HIP complex is formed by dissolving the protein or polypeptide in water at minimal ionic strength. The pH is adjusted to as low a pH value as is practical to ensure stability and activity. A stock solution of SDS is added so that the number of equivalents of SDS matches the number of basic groups. For insulin, the pH is adjusted to 2.5. and 6 molar equivalents of SDS are used per mole of insulin. The resulting complex precipitates from solution, is collected, and dried at room temperature. The solid HIP complex may be stored at higher humidities and temperatures than the native proteins without noticeable loss of activity.

Dissolution in a non-reactive organic solvent, such as 1-octanol, produces a true solution of a protein. The HIP complex of insulin stored in 1-octanol is much more stable than insulin in water, as shown by its enhanced thermal stability.

Example 16

Use of HIP Complex Formation for Protein Purification

The hydrophobicities of HIP complexes of proteins will differ according to the fraction of the protein's surface covered by the alkyl sulfate molecules. In turn, the HIP protein complexes are separated using a variety of methods, including hydrophobic interaction columns.

Further, proteins may be purified by selective precipitation out of solution. For example, a protein is separated from additives such as human serum albumin (HSA), which may be present in amounts 20–50 times greater than the protein. Since HSA does not precipitate out of solution at pH 5.0 with SDS, a basic protein may be selectively precipitated and purified from HSA under those conditions.

Example 17

Use of HIP Complex Dissolved in an Organic Solution for Administration of a Protein to a Patient The administration of HIP complexes to a patient may be accomplished in a number of ways. A biodegradable polymer/HIP complex system may be dissolved in an organic solvent, for example N-methyl pyrrolidone, and injected subcutaneously to form an implant, processed to form microspheres which can be injected subcutaneously or intramuscularly, processed to form an implant which is placed surgically under he skin or given orally as part, of an oral delivery system for peptides and proteins. The solid HIP complex may also be prepared as a suspension or a non-aqueous solution, which may be injected or placed on the skin where the complex may partition into the skin. The HIP complex may also be nebulized and administered to a patient via inhalation, for pulmonary drug delivery. The HIP complex may also be formulated to be given orally, such that it is protected from degradation in the stomach via an enterically coated capsule, and released in either the upper or lower intestinal tract. The HIP complex may be loaded alone or in conjunction with oils, bile salts, or other enhancers to increase absorption. The HIP complex may also be suspended or dissolved in oil and introduced to the patient as a rectal or vaginal suppository.

Example 18

Preparation of a Drug With Reduced Bitter Taste

The low solubility of the HIP complex results in diminished taste of bitter tasting drugs taken orally. The HIP complex may also be dissolved in oil so as to further reduce bitter taste. The slow rate of hydrolysis, especially in an oil-type vehicle, prevents the bitter tasting drug from dissolving in the mouth and being tasted.

Examples 19–29

Batch Preparation of Particles Using Gas Antisolvent Precipitation

Examples 19–29 demonstrate batch manufacture of particles having a pharmaceutical substance and an amphiphilic material using supercritical carbon dioxide as a gas antisolvent.

Figure 13:
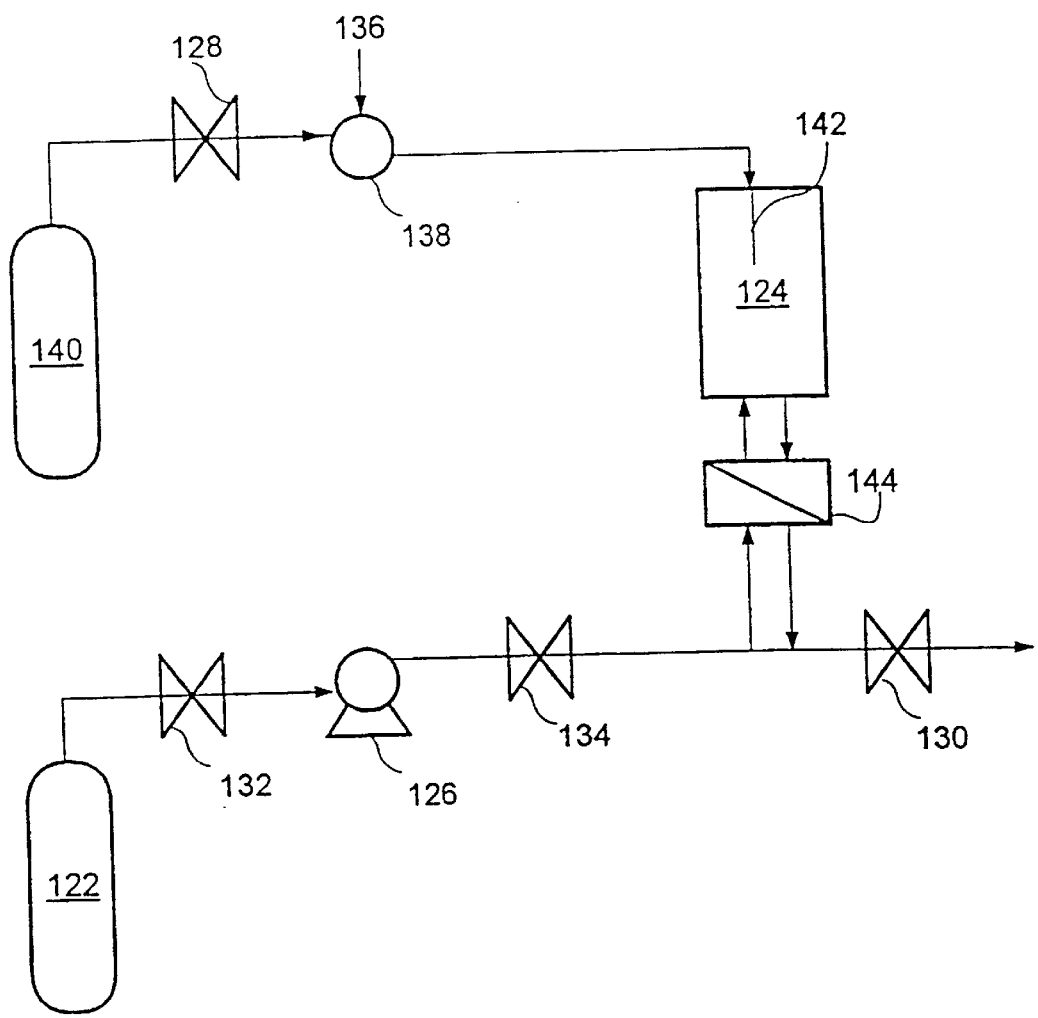
FIG. 13 shows a process flow diagram for batch processing for gas antisolvent precipitation relating to Examples 19–29.

FIG. 13 shows a process flow diagram for the batch processing of Examples 19–29. Referring to FIG. 13, supercritical carbon dioxide from the antisolvent tank 122 is fed into the antisolvent chamber 124 and is pressurized using a hand syringe pump 126, with valve 128 and valve 130 closed and valve 132 and valve 134 open. After the antisolvent chamber is pressurized, then valve 134 is closed and the test solution 136 is fed into an injection port 138. Nitrogen from a propellant tank 140 is pressurized behind the injection port 138 and is used to force the solution through a sonicated orifice 142 to spray the test solution 136 into the antisolvent chamber 124. The test solution 136 for each example has a pharmaceutical substance and an amphiphilic material dissolved together as a hydrophobic ion pair complex in an organic solvent. Some examples have a biodegradable polymer also dissolved in the organic solvent. Solid particles which precipitate are allowed to settle, with all valves closed, onto a scanning electron microscope (SEM) stub in the antisolvent chamber 124. The antisolvent chamber 124 is then slowly depressurized through the valve 130 and the SEM stub is removed for analysis. Any remaining solid particles from the antisolvent chamber 124 are collected on the filter 144.

Figure 14:
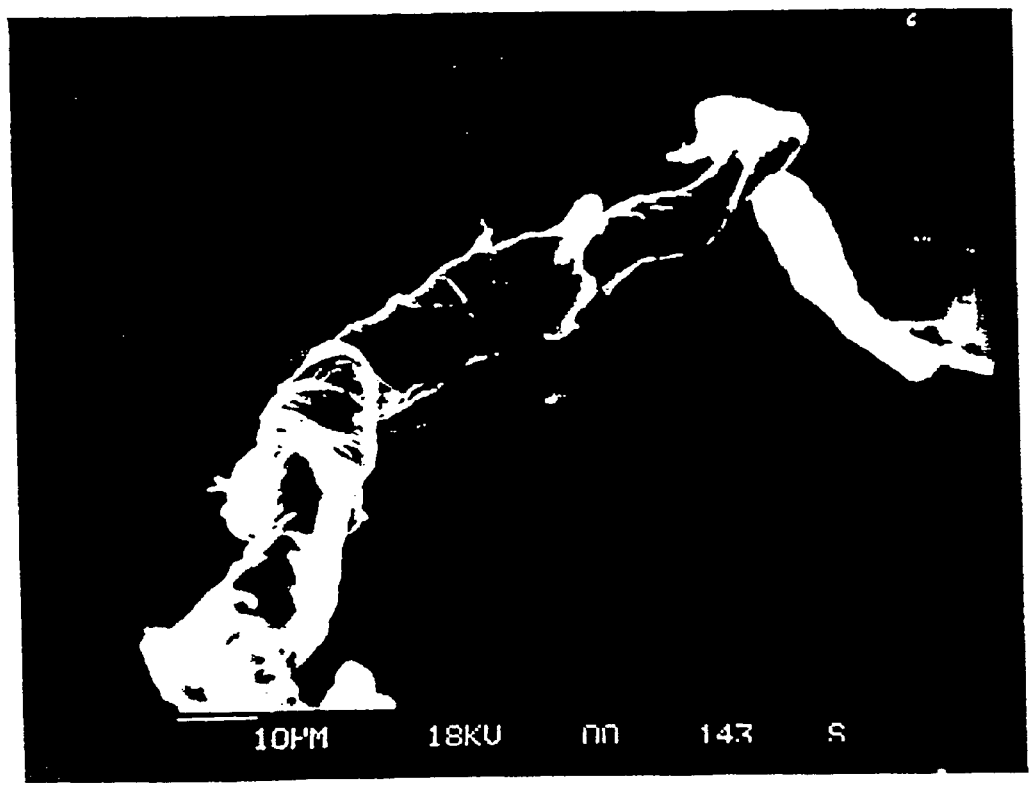
FIG. 14 is an SEM photomicrograph of a particle of the present invention comprising imipramine.
Figure 15:
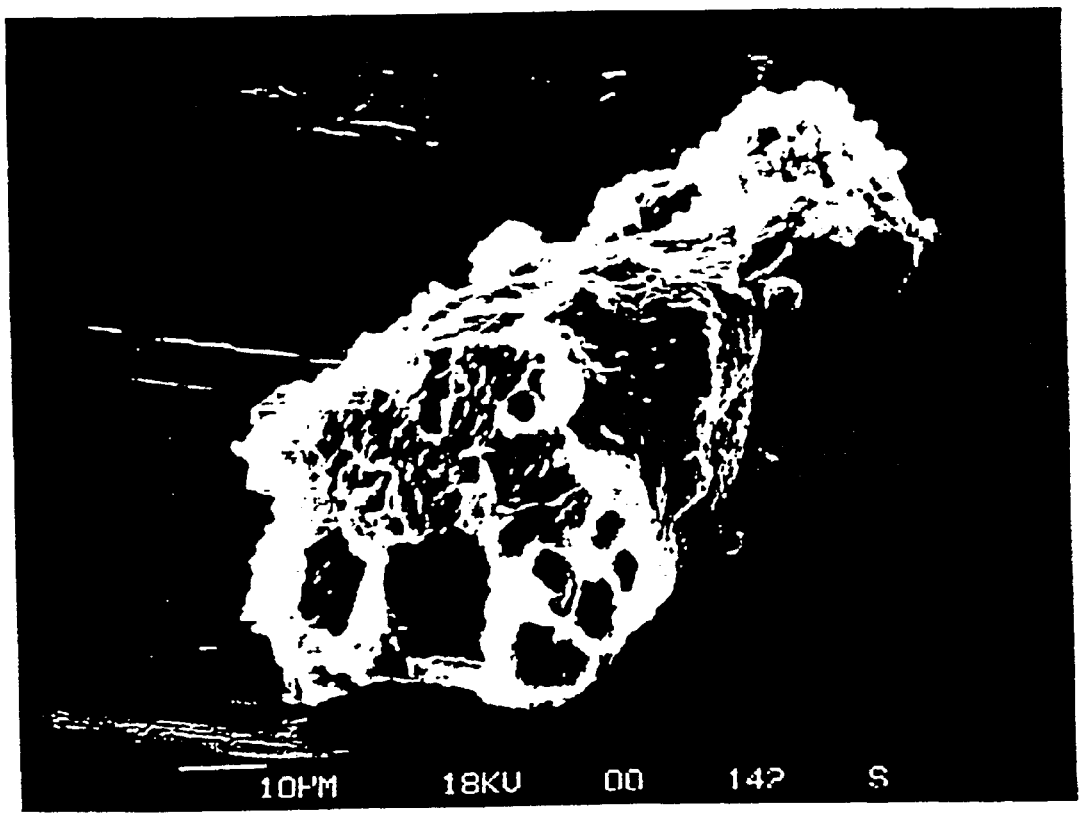
FIG. 15 is another SEM photomicrograph of a particle of the present invention comprising imipramine.
Figure 16:
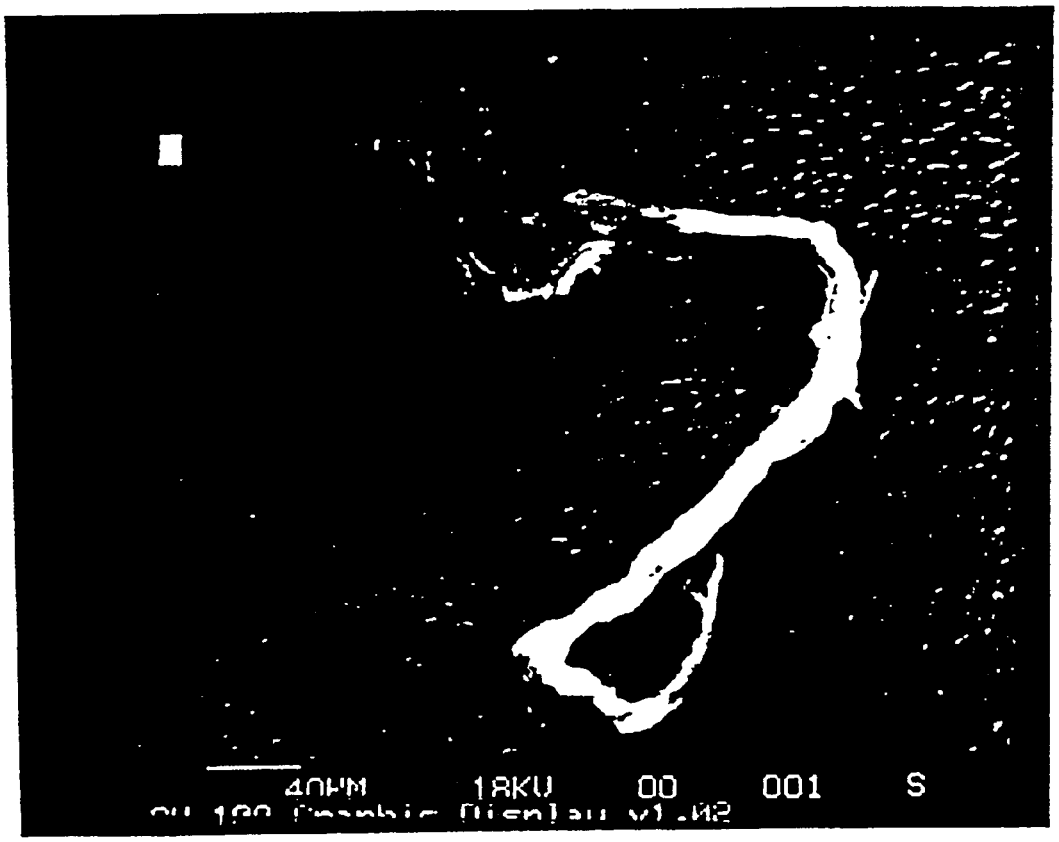
FIG. 16 is a SEM photomicrograph of a particle of the present invention comprising ribonuclease and poly (ethyleneglycol).
Figure 17:
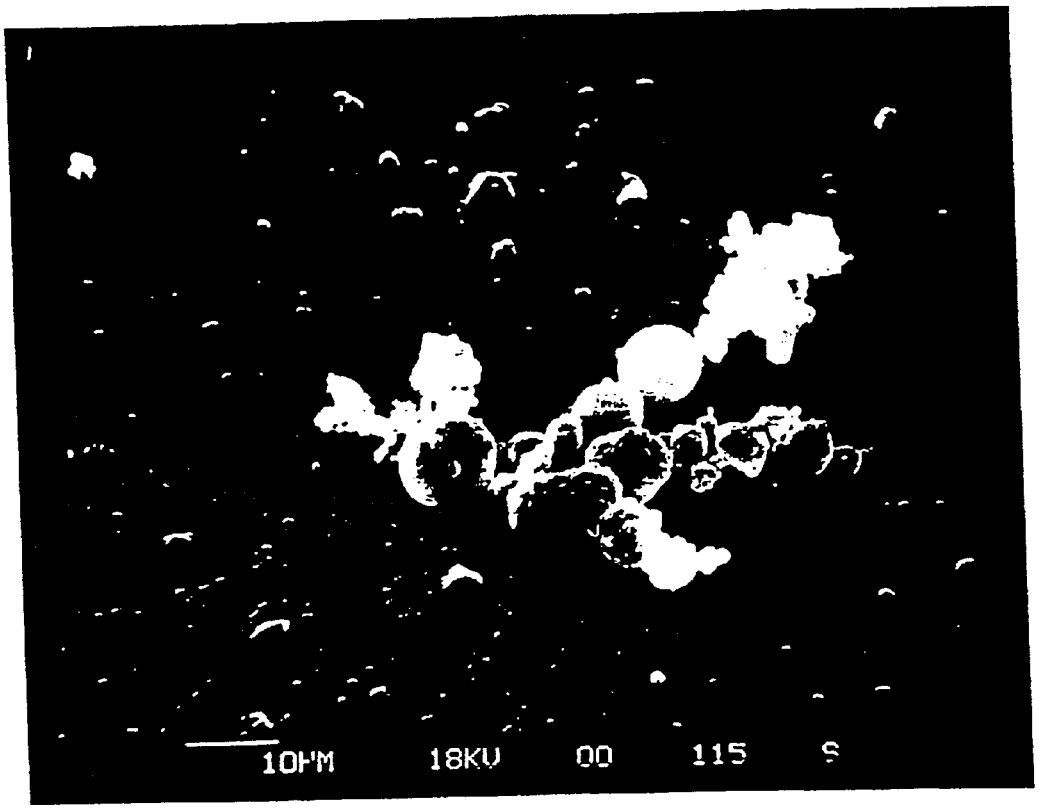
FIG. 17 is a SEM photomicrograph of particles of the present invention comprising a-chymotrypsin.
Figure 18:
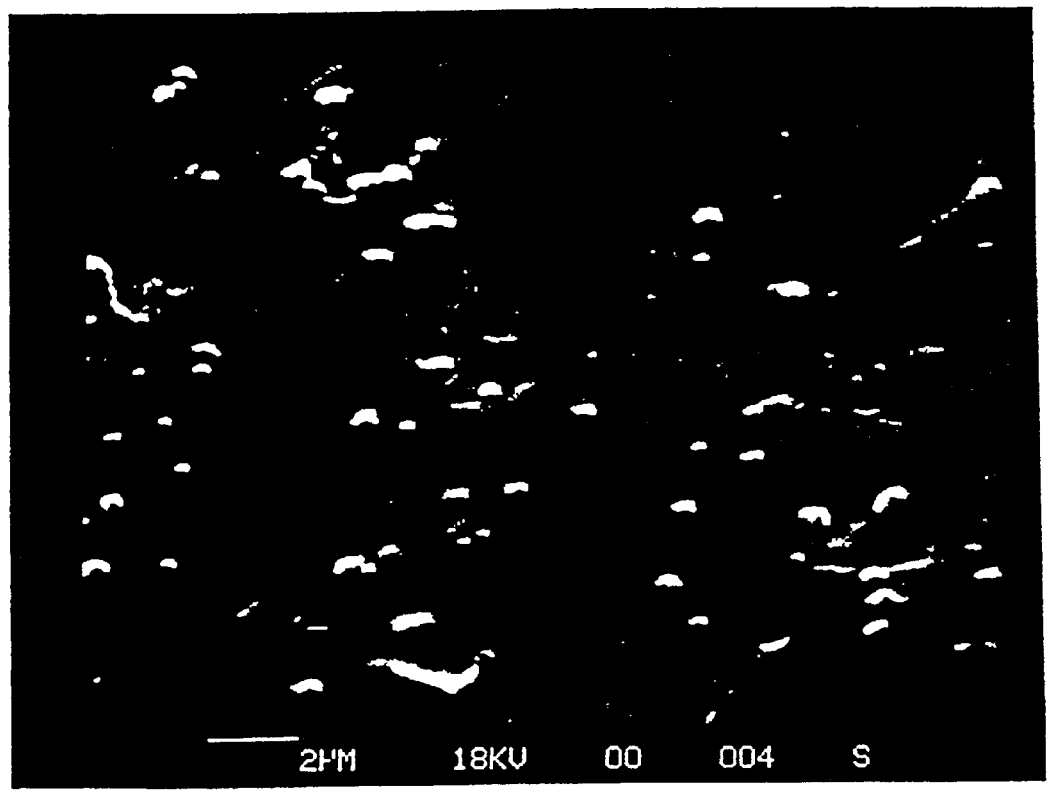
FIG. 18 is a SEM photomicrograph of particles of the present invention comprising pentamidine.

The makeup of each test solution for Examples 19–29 is shown in Table 2. Test conditions and results, including a description of particles which are precipitated, are shown in Table 3. FIGS. 14 and 15 are SEM photomicrographs of imipramine particles of Example 22, showing the elongated fiber-like shape of the particles. In FIG. 15 it may be seen that the fiber-like particle has a hollow interior in which small particles of another pharmaceutical substance could be loaded for some pharmaceutical applications. FIG. 16, is a SEM photomicrograph of a particle of ribonuclease and poly (ethylene glycol) of Example 27, showing an opening in the end of the particle into a hollow interior space. FIG. 17 is a SEM photomicrograph of particles of α-chymotrypsin of Example 19, showing ultrafine spheroidal particles of a size smaller than about 10 microns, with many of a size of around 1 micron. FIG. 18 is a SEM photomicrograph of pentamidine particles of Example 29 of a size smaller than about 1 micron.

TABLE 2

| | Pharm. Substance | | Amph. Material | | Polymer | | |
|---|---|---|---|---|---|---|---|
| Example | Type | Conc.[1] | Type | Ratio[2] | Type | Conc.[3] | Solvent |
| 19 | α-chymotrypsin | 1.4 | AOT[4] | 40 | — | — | iso-octane |
| 20 | α-chymotrypsin | 3.81 | AOT[4] | 40 | — | — | iso-octane |
| 21 | α-chymotrypsin | 0.1 | AOT[4] | 40 | PLA[5] | 1.31 | methylene chloride |
| 22 | Imipramine | 3.4 | AOT[4] | 1 | — | — | iso-octane |
| 23 | Insulin | 1.33 | SDS | 9 | — | — | pyridine |
| 24 | Insulin | 1.33 | SDS | 9 | — | — | THF[8] |
| 25 | Insulin | 1.33 | SDS[6] | 9 | — | — | methanol |
| 26 | Ribonuclease | 1.0 | SDS[6] | 20 | — | — | methanol |
| 27 | Ribonuclease | 1.0 | SDS[6] | 20 | PEG[7] | 7.91 | methanol |

TABLE 2-continued

| | Pharm. Substance | | Amph. Material | | Polymer | | |
|---|---|---|---|---|---|---|---|
| Example | Type | Conc.[1] | Type | Ratio[2] | Type | Conc.[3] | Solvent |
| 28 | cytochrome C | 0.23 | SDS[6] | 40 | — | — | ethanol |
| 29 | Pentamidine | 5.6 | SDS[6] | 2 | — | — | ethanol |

[1] mg of pharmaceutical substance per ml of solvent.
[2] molar ratio of amphiphilic material to pharmaceutical substance.
[3] mg of polymer per ml of solvent.
[4] bis-(2-ethylhexyl) sodium sulfosuccinate.
[5] poly (L-lactic acid) of approx. 100 kDa molecular weight.
[6] sodium dodecyl sulfate.
[7] poly (ethylene glycol) of approx. 3350 Da molecular weight.
[8] tetrahydrofuran

TABLE 3

| | Test Conditions | | |
|---|---|---|---|
| Example | Temp (° C.) | Press. (bar) | Particles |
| 19 | 34 | 76 | spheroidal. approx. 10μ and smaller |
| 20 | 28 | 76 | irregular shape, approx. 1μ dia. |
| 21 | | | spheroidal. approx. 2–3μ dia. |
| 22 | 36 | 85 | fiber-like, approx. 10μ dia. and 1 cm long |
| 23 | 34.5 | 85 | spheroidal |
| 24 | 34.6 | 85 | irregular. approx. 1–5μ |
| 25 | 35.2 | 85 | |
| 26 | 35.5 | 85.5 | spheroidal, approx 50μ |
| 27 | 35.3 | 85 | fiber-like, approx. 10μ dia. and 1 mm long, spheroidal, approx 0.5–1μ |
| 28 | 35.3 | 77 | collapsed spheres, approx 5μ dia. |
| 29 | 35 | 82 | spheroidal, approx. 0.1–1μ dia. |

Examples 30–32

Continuous Manufacture of Solid Particles by Gas Antisolvent Precipitation

Examples 30–32 show continuous manufacture of solid particles comprising a pharmaceutical substance and an amphiphilic material.

Figure 19:
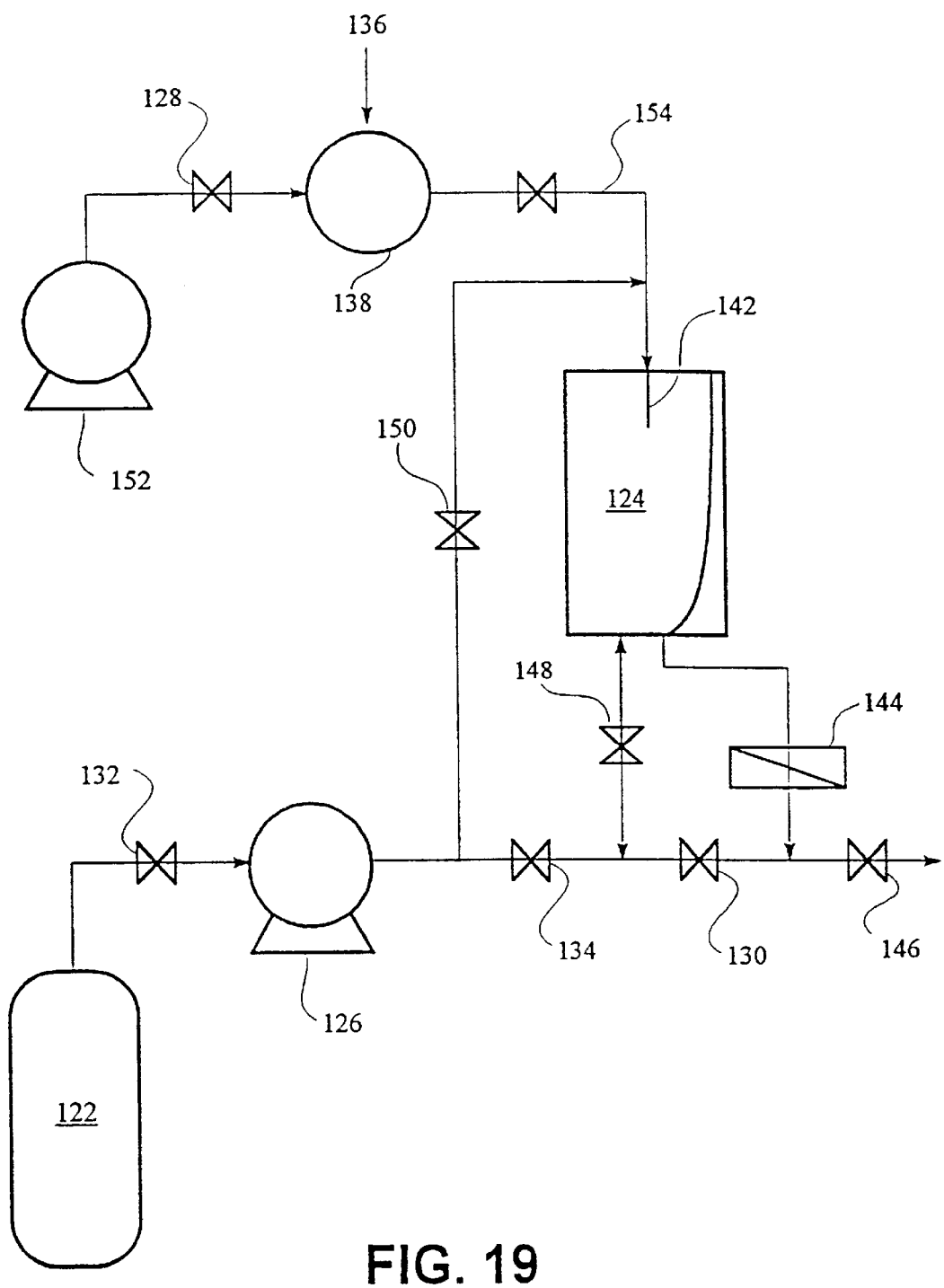
FIG. 19 shows a process flow diagram for continuous processing for gas antisolvent precipitation relating to Examples 30–32.

FIG. 19 shows a process flow diagram for the continuous manufacture test for Examples 30–32. The antisolvent chamber 124 is first pressurized with an automatic syringe, pump 126 with a back pressure regulator 146 adjusted maintain the desired antisolvent pressure in the antisolvent chamber 124 at a given antisolvent flow rate through the system. This initial pressurization is performed with the valve 148, the valve 134 and the valve 130 closed and with the valve 150 and the valve 132 open. One of two methods for metering the solution 136 into the antisolvent chamber 124 is used for each example. One method is to load the pump 152 with pure solvent and to spray the pure solvent into the antisolvent chamber 124 until a steady state is achieved. The solution 11.6 is then loaded into the injection port 138 and spiked into the solvent delivery line 154 to the antisolvent chamber 124. The second method is to load the pump 152 with the solution and, bypassing the injection port, to deliver the solution to the antisolvent chamber 124. Both delivery techniques are operated at a flow rate of 1 milliliter per minute with a carbon dioxide flow rate of 20 milliliters per minute. In both cases, the solution enters the antisolvent chamber 124 through the sonicated orifice 142. During operation, carbon dioxide is vented from the top of the antisolvent chamber to allow particles to settle and not be entrained in the exiting carbon dioxide. Any particles that are washed out of the antisolvent chamber 124 are collected on the filter 144.

After spraying the solution 136 into the antisolvent chamber, then valves 150 and 130 are closed and valves 134 and 148 are opened and carbon dioxide is metered into the antisolvent chamber 124 from bottom to top to flush any residual solvent from the antisolvent chamber 124. The system is then slowly depressurized and particles which have precipitated are collected from either the antisolvent chamber 124 or the filter 144.

The makeup of the solution for each of Examples 30–32 is shown in Table 4. Table 5 shows the test conditions for each of Examples 30–32 and results of the examples, including a description of particles which are produced.

TABLE 4

| | Pharm. Substance | | Amph. Material | | Polymer | | |
|---|---|---|---|---|---|---|---|
| Example | Type | Conc.[1] | Type | Ratio[2] | Type | Conc.[3] | Solvent |
| 30 | streptomycin | 5 | AOT[4] | 3 | — | — | methylene chloride |
| 31 | streptomycin | 0.14 | AOT[4] | 3 | PLA[5] | 2.62 | methylene chloride |

TABLE 4-continued

| | Pharm. Substance | | Amph. Material | | Polymer | | |
|---|---|---|---|---|---|---|---|
| Example | Type | Conc.[1] | Type | Ratio[2] | Type | Conc.[3] | Solvent |
| 32 | streptomycin | 0.66 | AOT[4] | 3 | PLA[5] | 2.62 | methylene chloride |

[1]mg of pharmaceutical substance per ml of solvent.
[2]molar ratio of amphiphilic material to pharmaceutical substance.
[3]mg of polymer per ml of solvent.
[4]bis-(2-ethylhexyl) sodium sulfosuccinate.
[5]poly(L-lactic acid) of 100 Kda molecular weight.

TABLE 5

| | Test Conditions | | |
|---|---|---|---|
| Example | Temp (° C.) | Press. (bar) | Particles |
| 30 | 35 | 88 | spheroidal. approx. 1$\mu$ |
| 31 | 36.8 | 89 | spheroidal. approx. 0.4$\mu$ |
| 32 | 36.2 | 88.2 | spheroidal. approx. 0.4$\mu$ |

Example 33

Synthesis of Arginine Octyl Ester

This example describes the synthesis of arginine octyl ester. This ester was synthesized by the in situ generation of the acid chloride of arginine, followed by direct esterification with the appropriate alcohol (see FIG. 20A).

One millimole of L-arginine free base (Sigma) was suspended in 50 mL of neat 1-octanol (Sigma). A rubber septum was used to keep excess water in the atmosphere from reacting with the thionyl chloride (SOCl$_2$; Aldrich). One equivalent of thionyl chloride was added, and the reactants were slowly heated to 90° C. The mixture was allowed to cool to 60° C, one more equivalent of thionyl chloride was added, and the mixture was heated again to 90° C; all solid (presumably arginine free base) disappeared. The reaction mixture was allowed to sit at 90° C. for 2 hours exposed to the atmosphere to remove excess thionyl chloride. A five-volume excess of diethyl ether was added to the mixture, and a gummy precipitate formed and coagulated. This precipitate was washed with saturated sodium bicarbonate solution, whereupon a powder precipitate formed from the gummy precipitate. This was removed by gravity filtration and washed 2× with saturated sodium bicarbonate and 2× with diethyl ether.

The powder was found to be insoluble in a variety of organics, including alcohols, hydrocarbons, aromatics, DMF and pyridine. The powder was also insoluble in water, and would only dissolve in 0.1 N or stronger HCl.

TLC Assay A$_{550}$ (Sigma) showed distinct differences in mobility for substrate and product (the product traveled with the solvent front). To perform this assay, product and substrate were dissolved in 0.1 N HCl at 1 mg/ml, and the product and substrate solutions were then spatted onto a Selecto silica gel TLC plate which was placed in a vapor-saturated vessel containing 60% isopropanol, 15% methyl ethyl ketone, and 25% 1 N HCl. The chromatograms were developed with ninhydrin.

The molecular structure of the product was verified by NMR and fast atom bombardment (FAB) mass spectrometry to be arginine octyl ester dihydrochloride. The melting point was 155° C. The yield was approximately 100%.

Example 34

Synthesis Of Arginine Octyl Ester

One millimole thionyl chloride was added to a stirred suspension of one millimole L-arginine free base in 50 mL of octanol under nitrogen. The mixture was heated to 90° C, and the temperature was maintained with stirring for 2 hours. The mixture was cooled to 60° C, one more equivalent of thionyl chloride was added, and the mixture was stirred at 60° C. for an additional 2 hours, at which time the reaction was seen to be complete by TLC (performed as described in Example 33). Excess thionyl chloride was allowed to evaporate. Then, the solution was cooled to room temperature, and 250 ml diethyl ether was added. Washing of the resultant soft white precipitate with saturated sodium bicarbonate solution gave a white solid. Filtration of this suspension and washing of the filtrate with saturated sodium bicarbonate solution (3× with 20 ml), water (3× with 20 ml), acetone (3× with 20 ml) and diethyl ether (3× with 20 ml) gave arginine octyl ester. The yield was 85%. FAB mass spectrometry gave the expected parameters for arginine octyl ester.

Example 35

Synthesis Of Arginine Dodecyl Ester

This ester was synthesized using approximately the same procedure as described in Example 33 for the octyl ester. 1-Dodecanol (Aldrich) was used in place of the 1-octanol.

After several rounds of thionyl chloride addition, the substrate did not disappear as in the octyl synthesis. As the mixture was heated to approximately 80° C, the substrate began to clump together. Additional rounds of thionyl chloride addition did not change the appearance of the clumped substrate. TLC of the supernatant showed some product. Five volumes of diethyl ether caused some opaque precipitate to form, but it did not coagulate as in the octyl synthesis. Attempts using Whatman filter paper to filter out the precipitate by both gravity and Buchner filtration were unsuccessful, so the precipitate was collected by centrifugation. The resulting pellet had a gummy appearance like the octyl product. This pellet was washed with saturated sodium bicarbonate, and a product with a more powdery appearance formed. Centrifugation could not separate the product from the aqueous bicarbonate solution, so the precipitate was collected in a Buchner funnel with Whatman filter paper. Washing with either saturated sodium bicarbonate or diethyl ether seemed to reduce the amount of product.

TLC. NMR and FAB mass spectrometry gave the expected results for arginine dodecyl ester dihydrochloride. The melting point was 125–130° C. The yield was 110 mg (about 1%).

Clearly, this synthetic approach did not work well. In view of the low yield, other synthetic approaches utilizing the Vilsmeier route (FIG. 20B) were tried, but none gave greater yields (the highest yield obtained was 0.5%).

Example 36

Synthesis of Arginine Dodecyl Ester

A suspension of L-arginine free base (0.6 g, 3.5 mmol), sulfuric acid (0.31 ml, 7 mmol), and dodecanol (25 ml) were stirred together at 140° C. under nitrogen. After 6 hours, a clear light yellow solution resulted, and TLC indicated the reaction to be complete. The reaction mixture was diluted with diethyl ether (50 ml), and washed with water (3×25 ml). The combined aqueous extracts were washed with diethyl ether (2×25 ml), and basified with 1N KOH solution, upon which a white solid precipitated. Filtration of the suspension and washing of the filtrate with water (3× with 25 ml), acetone (3× with 25 ml) and diethyl ether (3× with 25 ml) gave arginine dodecyl ester. The yield was 86%. Melting point was 125–130° C. NMR gave the expected results for arginine dodecyl ester.

Example 37

Synthesis of a Cholesterol Carbonate

N,N-dimethyl ethanolamine (Aldrich; 0.24 ml. 2.44 mmol) was added dropwise over the course of 30 minutes at room temperature to a stirred solution of cholesterol chloroformate (Aldrich; 1.0 g. 2.2 mmol) in dichloromethane (Fisher, 30 ml). The resulting white suspension was stirred at room temperature for 10 minutes, at which time TLC (20:1 hexanes:ethyl acetate) showed the reaction to be complete. Saturated sodium bicarbonate solution (10 ml) was added to the suspension at which point a clear solution resulted. The organic laver was extracted, washed with water and saturated brine, and dried over magnesium sulfate. Filtration and evaporation gave the product (CC-CHOL) as a syrup, which crystallized on standing at room temperature. The yield was 85%. CC-CHOL has the following formula:

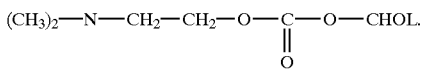

Example 38

Characterization of Arginine Esters

Stock solutions of the arginine esters were made by first dissolving the powder in 0.1 N HCl to give a 10 mM solution and then raising the pH to a value between 5 and 6. The pH should not be raised above 8.

A. Partitioning

Anionic compounds were dissolved in pH 5.5 buffer (10 mM bis-tris propane, 10 mM $CaCl_2$, 10 mM KCl). Appropriate amounts of the stock solution of arginine ester (see above), the anionic compound and buffer were mixed so that the final concentration of the anionic material was 1 mg/mL. An equal volume of organic solvent was added, and the samples were vortexed for 15 seconds on high speed. Layers were separated by centrifugation at 4000 rpm for 5 minutes. Concentrations of the anionic material in the aqueous and organic layers were determined by UV spectroscopy on a Beckman DU-64 series spectrophotometer. The results are given in Table 6 below.

TABLE 6

| Compound[s] | Ester | Solvent | log p* |
|---|---|---|---|
| p-toluenesulfonic acid, sodium salt | none | octanol | −1.62 |
| p-toluenesulfonic acid, sodium salt | C8[#] | octanol | −0.353 |
| p-toluenesulfonic acid, sodium salt | C12[#] | octanol | −0.336 |
| p-toluenesulfonic acid, sodium salt | none | isooctane | −2.7 |
| p-toluenesulfonic acid, sodium salt | C8 | isooctane | −2.2 |
| sodium benzoate | none | octanol | −1.2 |
| sodium benzoate | C8 | octanol | 0.05 |
| sodium benzoate | C12 | octanol | −0.072 |
| DNA ("degraded free acid") | none | octanol | −1.52 |
| DNA ("degraded free acid") | C8 | octanol | −1.24 |
| adenosine triphosphate | none | octanol | −3.23 |
| adenosine triphosphate | C12(1:1)[+] | octanol | −1.48 |
| adenosine triphosphate | C12(3:1)[+] | octanol | 0.022 |

[s]p-Toluenesulfonic acid, sodium salt was purchased from Kodak. Sodium benzoate and adenosine triphosphate were purchased from Sigma.
*Log p is log (concentration in organic phase/concentration in aqueous phase).
[#]C8 is arginine octyl ester, and C12 arginine dodecyl ester.
[+]Ratio of detergent to anionic compound.

For DNA and bovine serum albumin (data not shown), the solutions turned cloudy when argnine dodecyl ester was added, but none would partition into octanol layer, although some was trapped at the interface. Cloudiness could not be spun out in centrifuge.

B. Surface Tension

Surface tension was measured using a Fisher surface tensiometer. Briefly, a platinum iridium ring with a diameter of 6 cm was lowered into the appropriate dilution of detergent in 0.1 N HCl. Surface tension was read at the point where the force on the ring upwards caused the ring to break contact with the liquid surface. The results are shown in FIGS. 22A–B.

Figure 22A:
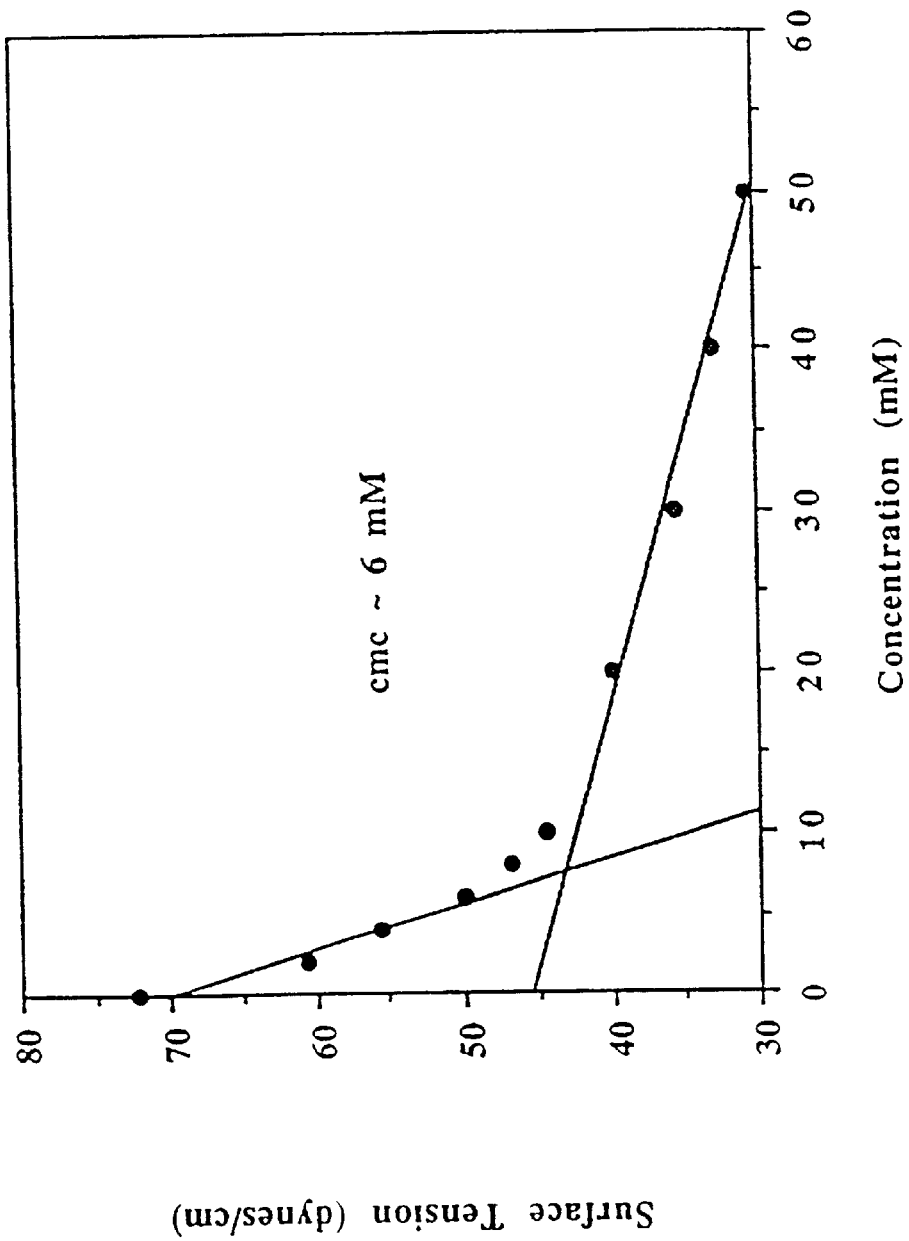
FIG. 22A is a graph of surface tension versus concentration for arginine octyl ester.
Figure 22B:
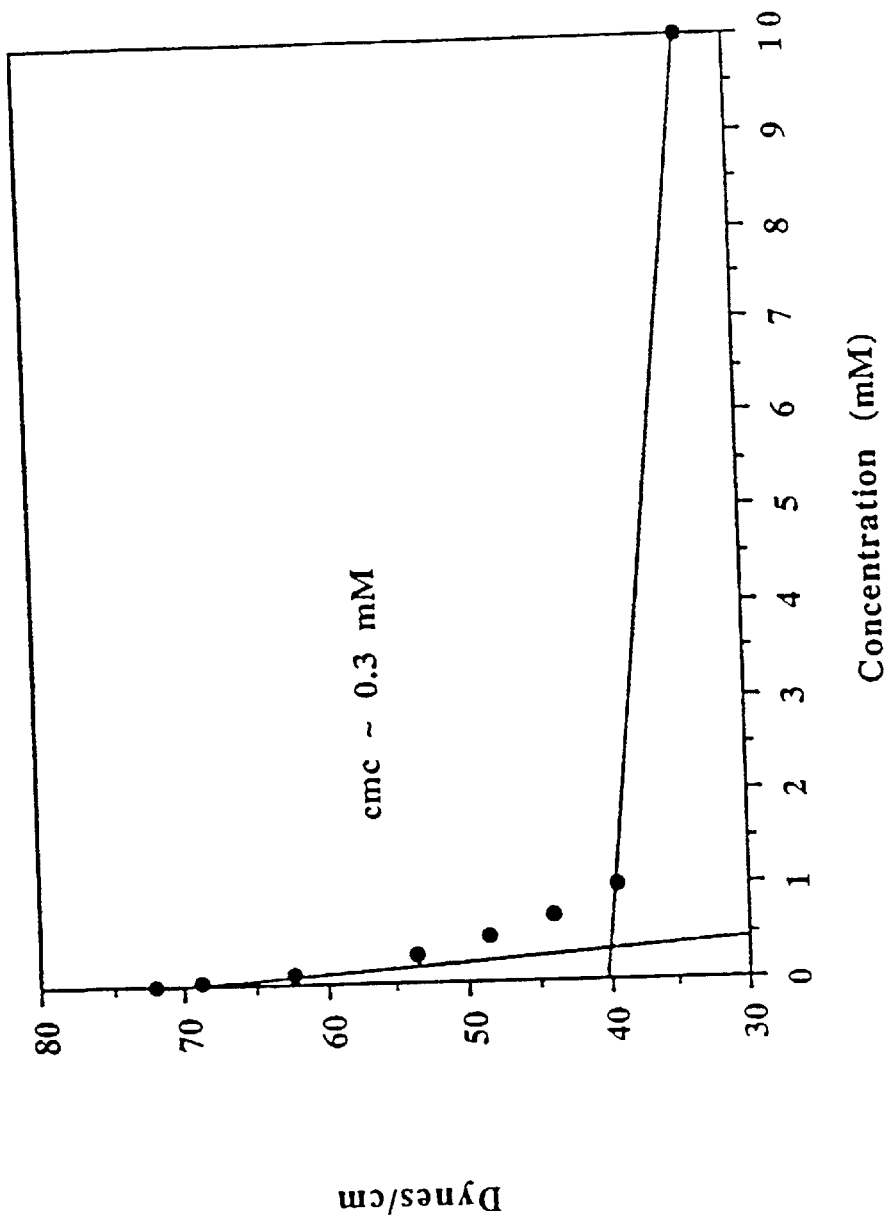
FIG. 22B is a graph of surface tension versus concentration for arginine dodecyl ester.

The results show that arginine octyl ester is a relatively poor detergent with a critical micelle concentration (cmc) of about 6 mM (2.2 mg/ml) (see FIG. 22A). However, the dodecyl ester is a much better surfactant, with a cmc of approximately 0.3 mM (0.10 mg/ml) (see FIG. 22B). Considering the better detergent properties of the dodecyl ester, all subsequent studies focused on the dodecyl ester.

C. Cytotoxicity

The cytotoxicity of arginine dodecyl ester was investigated in cell culture with two types of cells (see Cory et al, Cancer Commun., 3, 207–212 (1991)): CCRF-CEM cells, a human T-cell leukemia cell line that grows in suspension (obtained from the American Type Culture Collection, ATCC); and a green monkey kidney cell line (COS-7) that grows in monolayers (also obtained from ATCC). For comparison, the cells were also exposed to tetradecyltrimethylammonium bromide (DTAB) (Sigma).

Cells were plated into 96-well plates (Corning) in a total of 200 μL Dulbecco's modified minimal essential medium for COS-7 cells, RPMI 1640 for CEM cells, supplemented with penicillin G (50 U/ml), streptomycin sulfate (50 μg/ml), and 10% fetal calf serum, at 10,000 cells/well for COS-7 and 50,000 cells/well for CEM cells. The plates were incubated at 37° C. for 24 hours after plating. The cells were then exposed to various concentrations of the detergents. Each detergent concentration was used in 8 replicate wells. After 2–6 hours, media/detergent solutions were aspirated, and the wells were washed twice with PBS. For CEM suspension cells, centrifugation of the suspension at 1000× g for 5 min between each wash was required. After washing, 200 μL of fresh medium were added, and the cells were incubated for 72 hours. After 72 hours, cell proliferation was determined using the Promega CellTiter 96 AQueous Non-Radioactive Cell Proliferation Assay. To do so, cells were exposed to MTS substrate (3-(4,5-dimethylthiazol-2-yl)-5-(3-carboxymethoxyphenyl)-2-(4sulfophenyl)-2H-tetrazolium for 3 hours. Cellular respiration was assessed by monitoring the appearance of a soluble formazan reduction product by spectrophotometry at 490 nm. Absorbance was read using a Molecular Devices spectrophotometric plate reader. Absorbance was directly proportional to the number of living cells in each well. Survival was plotted versus detergent concentration, with the untreated control group representing 100% survival. Detergent concentrations producing half-maximal growth inhibition ($IC_{50}$ values) were extrapolated from the resulting curves.

Figure 23A:
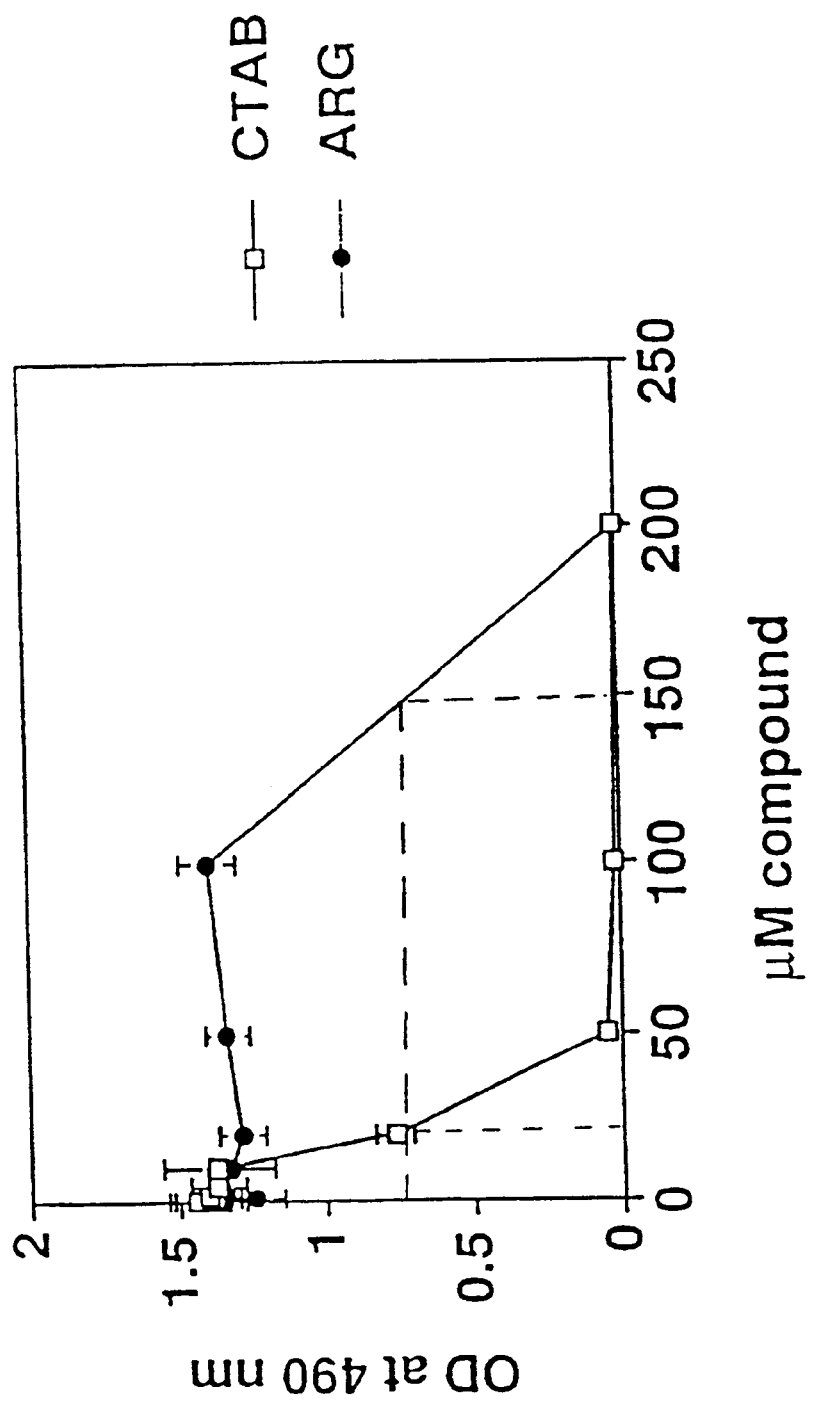
FIG. 23A is a graph of OD$_{490}$ versus concentration comparing cytotoxicity of arginine dodecyl ester and tetradecyltrimethylammonium bromide (CTAB) in CCRF-CEM cells.
Figure 23B:
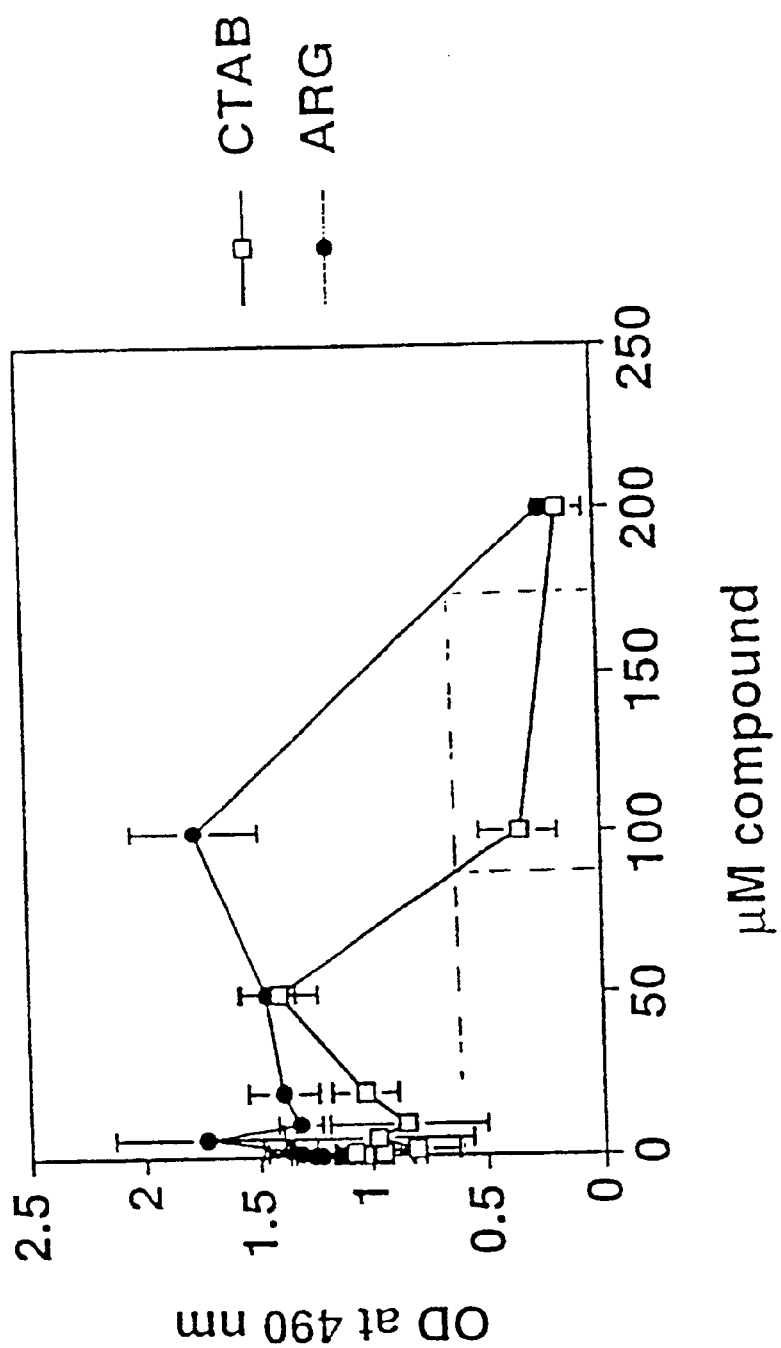
FIG. 23B is a graph of OD$_{490}$ versus concentration comparing cytotoxicity of arginine dodecyl ester and tetradecyltrimethylammonium bromide (CTAB) in COS-7 cells.

The results are shown in FIGS. 23A–B. In CCRF-CEM cells, the $IC_{50}$ for DTAB was 20 µM, whereas the arginine dodecyl ester had an $IC_{50}$ of 150 µM (FIG. 23A). This is seven-fold less toxicity for arginine dodecyl ester. Similar results were obtained in the COS-7 cells, where the $IC_{50}$ for DTAB was 80 µM, whereas the arginine dodecyl ester had an $IC_{50}$ of 175 µM (FIG. 23B). This is approximately two-fold less toxicity for arginine dodecyl ester.

Example 39

Transfection With Arginine Dodecyl Ester

The plasmid used was pRSV400luc. It was obtained from Dr. David Gordon Div. Endocrinology, University of Colorado School of Medicine, Denver, Colo. It was propagated in *Escherichia coil* strain DH5a (ATCC), isolated by a standard alkaline-SDS lysis procedure, and purified twice by isopycnic centrifugation on CsCl gradients (Sambrook et al, *Molecular Cloning: A Laboratory Manual* (Cold Spring Harbor Laboratory) (1989). COS-7 cells at approximately 50,000 cells per 60 mm diameter plate (Falcon) were used for transfection. Control experiments were done with Lipofectamine (GIBCO/Life Technologies, Gaithersburg, Md.).

In 200 total µl of serum-free medium, plasmid (20 µg) and Lipofectamine or arginine dodecyl ester were mixed and allowed to interact for 45 minutes. The volume was then brought to 1 mL with serum-free medium. Plates with cells were washed with serum-free medium. Then, 1 mL serum-free medium was added to plates already containing 2 mL serum-free medium and the plates were incubated at 37° C. for 4 hours. After 4 hours, serum was added so the final serum concentration was 10%. In another experiment, the time of incubation was varied.

After allowing cells to grow and express gene product for 36–50 hours, the cells were harvested. Harvested cells were lysed and processed for measurement of luciferase activity using potassium luciferin substrate as described in Fraser et al. *Mol. Pharmacol*, 47, 696–706 (1995). Intensity of luminescence should be proportional to the amount of expressed luciferase and, therefore, the efficiency of transfection. "Background" is the reading from just the substrate mixture on the luminometer before addition of cell lysate. Average background is approximately 50 units. Any reading over 100 units is considered significant.

Figure 24A:
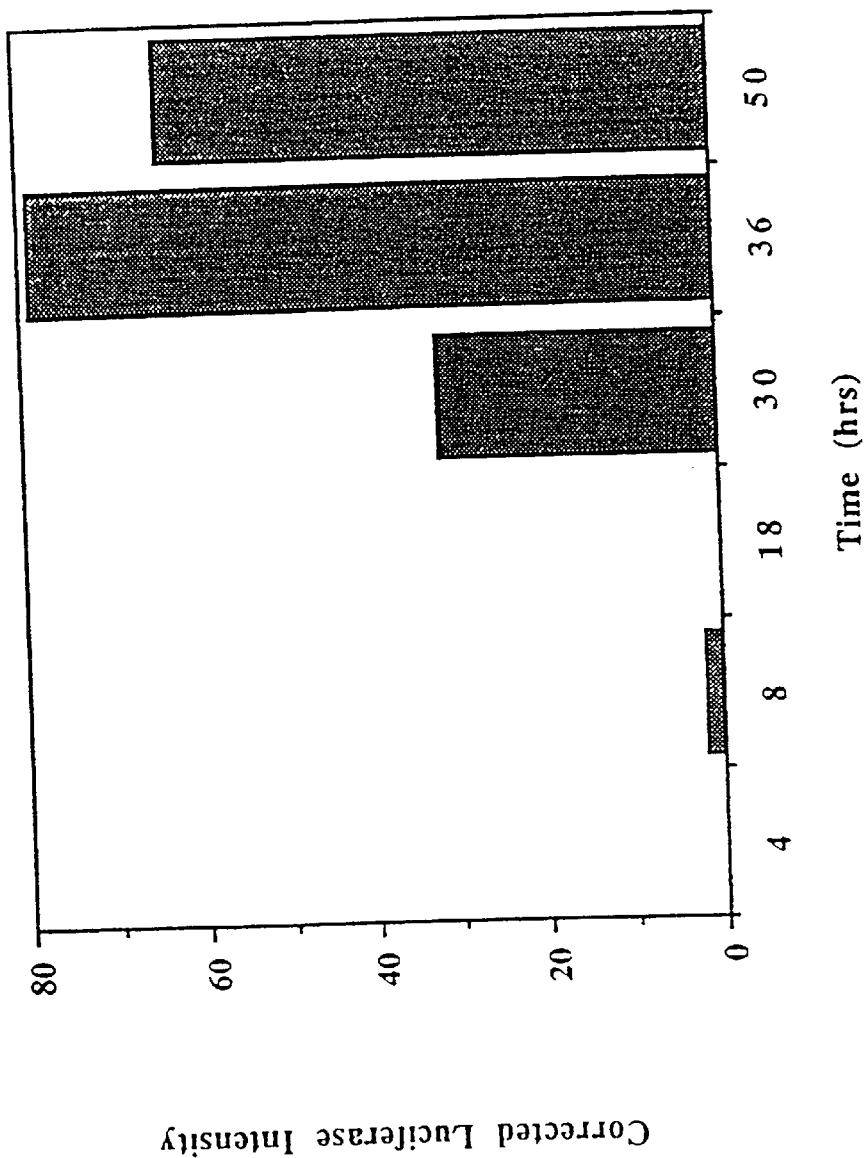
FIG. 24A is a graph showing the time dependence of DNA transfection using arginine dodecyl ester.
Figure 24B:
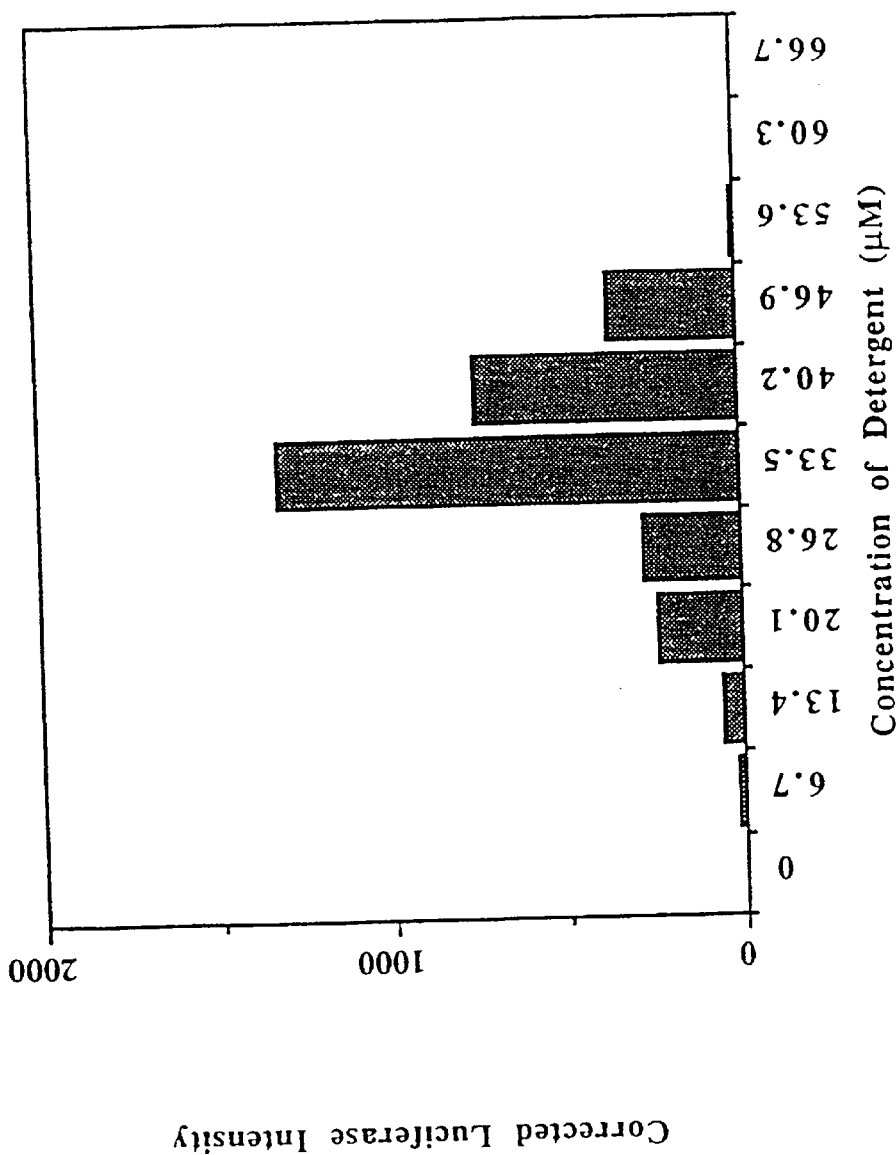
FIG. 24B is a graph of luciferase intensity versus concentration showing the effect of arginine dodecyl ester concentration on DNA transfection.

The results are shown in FIGS. 24A–B. The results demonstrate that arginine dodecyl ester promoted transfection of the plasmid in a concentration and time dependent manner. Note that the transfection studies were performed without formation of liposomes or the addition of helper lipids, which should provide a much larger increase in transfection efficiency. The intent of these experiments was to demonstrate that, even in serum-containing medium, there is sufficient interaction between the arginine esters and DNA to effect transfection of cells. The efficiency of transfection was about 100× higher for Lipofectamine than for arginine dodecyl ester.

Example 40

Characterization of CC-CHOL

CC-CHOL was tested for cytotoxicity as described in Example 38 using COS-7 and JEG-3 cells. JEG-3 cells are a human choriocarcinoma cell line available from ATCC. The culture medium was Eagle's minimum essential medium containing 10% serum.

Figure 25A:
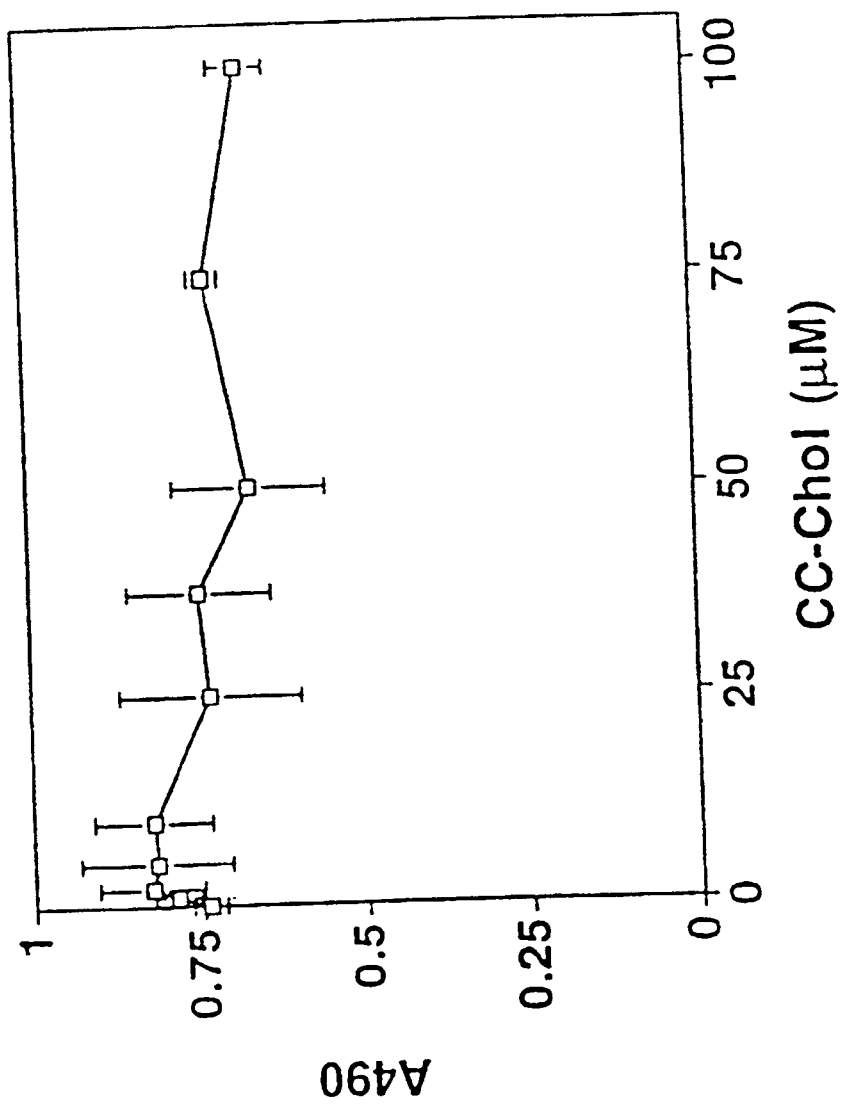
FIG. 25A is a graph of OD$_{490}$ versus concentration showing lack of cytotoxicity of CC-cholesterol in COS-7 cells.
Figure 25B:
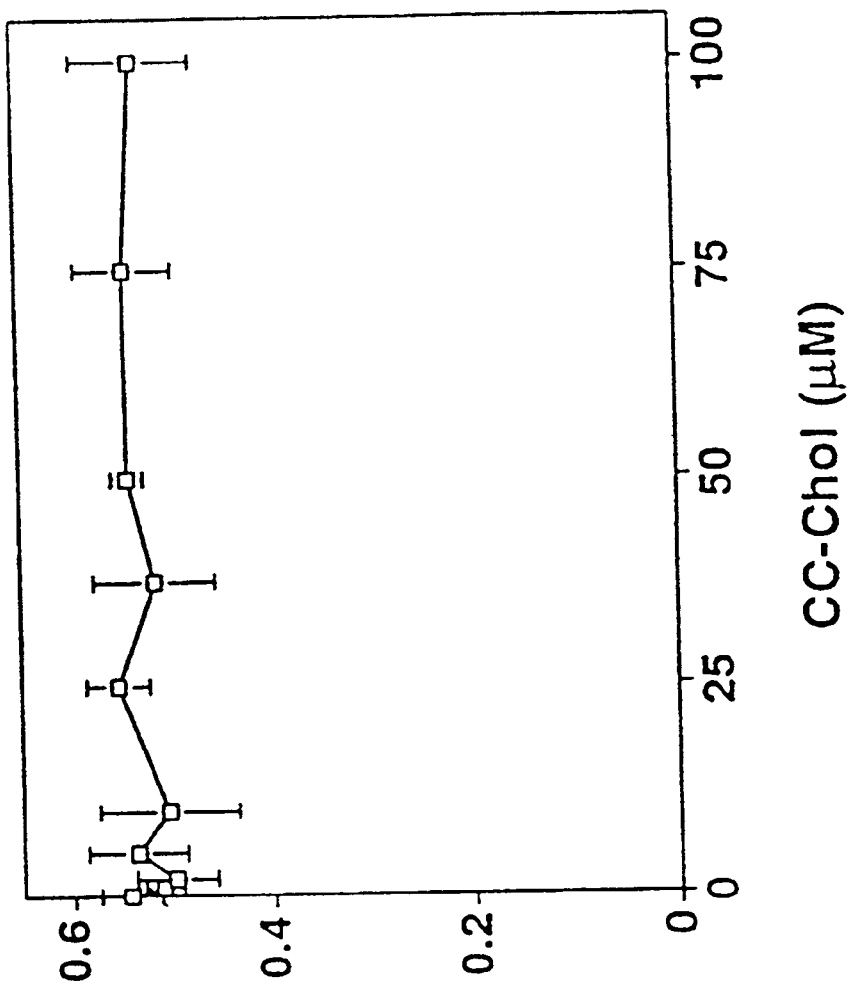
FIG. 25B is a graph of OD$_{490}$ versus concentration showing lack of cytotoxicity of CC-cholesterol in JEG-3 cells.
Figure 26:
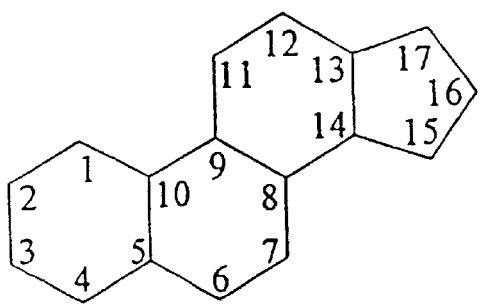
FIG. 26 shows the steroid backbone.

The results are shown in FIGS. 25A–B. The results show that CC-CHOL was not toxic to COS-7 and JEG-3 cells.

While various embodiments of the present invention have been described in detail, it should be understood that any feature of any embodiment may be combined with any other feature of any other embodiment. Any compatible combination of pharmaceutical substance, amphiphilic material, polymer and/or solvent may be used. Also, any feature of any processing method may be used with any solvent. Furthermore, the hollow, fiber-like particles may be prepared for any suitable combination of pharmaceutical substance and amphiphilic material. Moreover, the fiber-like particles may be made of a biocompatible polymer, alone or in combination with other materials, or a pharmaceutical substance, alone or in combination with other materials, which are directly soluble in the organic solvent. Such features are expressly included within the scope of the present invention.

Also, while various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for producing a biocompatible polymer particle for sustained release of a pharmaceutical substance, wherein said particle comprises substantially amorphous biocompatible polymer having a crystallinity of no more than about 25%, and wherein said particle comprises a substantially homogeneous mixture of said pharmaceutical substance and said amorphous polymer; comprising the steps of:
   a) providing:
      i) a solvent,
      ii) a pharmaceutical substance,
      iii) an amphiphilic material, selected from the group consisting of sulfates, sulfonates, phosphates, phospholipids, carboxylates, sulfosuccinates, arginine esters, cholesterol esters, carbamates, carbonates and ketals,
      iv) at least one biocompatible polymer selected from the group consisting of poly(L-lactic) acid, poly(D-lactic) acid, polyglycolic acid, polyanhydride, polycarboxyphenoxyhexane, polybutyrate, and cellulose; and
      v) an antisolvent fluid, wherein said antisolvent fluid comprises at least one antisolvent selected from the group consisting of carbon dioxide, nitrous oxide, ethane ethylene, chlorotrifluoromethane, monofluoromethane, acetylene, 1,1-difluoroethylene, hexafluoroethane, chlorotrifluorosilane and xenon;

b) combining said solvent, pharmaceutical substance and amphiphilic material to form a solution, wherein said pharmaceutical substance and amphiphilic material form a hydrophobic ion paired complex within said solution; and c) contacting at subcritical conditions said solution, said polymer, and said antisolvent fluid by concurrent flow to produce a mixture, wherein said mixture has a reduced temperature in the range of about 0.75–0.995, and wherein a reduced pressure relative to the antisolvent fluid is in the range of about 0.5–2.0, wherein the weight percentage of said hydrophobic ion paired complex to the total weight of said hydrophobic ion paired complex and said polymer is in the range of about 15% to 70%, and wherein the volumetric ratio of flow rate of said antisolvent fluid to the flow rate of said solution is in the range from about 5 to about 100.

2. The method of claim 1, wherein said amphiphilic material is further selected from the group consisting of sodium dodecyl sulfate, bis-(2-ethylhexyl) sodium sulfosuccinate, cholesterol sulfate and sodium laurate.

3. The method of claim 1, wherein said amorphous biocompatible polymer has a crystallinity of no more than about 15%.

4. The method of claim 3, wherein said amorphous biocompatible polymer has a crystallinity of no more than about 5%.

5. The method of claim 1, wherein said biocompatible polymer particle releases at least about 70% by weight of said pharmaceutical substance when immersed in a phosphate buffer solution at a temperature of 37° C.

6. The method of claim 1, wherein said particle releases less than about 15% by weight of said pharmaceutical substance during a period of 24 hours following immersing said particle in a phosphate buffer solution at a temperature of 37° C.

7. The method of claim 1, further comprising the step of washing said biocompatible polymer particle with an aqueous solution.

8. A plurality of said biocompatible polymer particles produced according to the method of claim 1, wherein said plurality of said biocompatible polymer particles are at least about 90% by weight smaller than about 10 microns.

9. A plurality of said biocompatible polymer particles produced according to the method of claim 1, wherein said plurality of said biocompatible polymer particles are at least about 90% by weight smaller than about 6 microns.

10. A plurality of said biocompatible polymer particles produced according to the method of claim 1, wherein said plurality of said biocompatible polymer particles are at least about 90% by weight smaller than about 1 micron.

11. The method of claim 1, wherein said biocompatible polymer particle is substantially spheroidal.

12. The method of claim 1, wherein said biocompatible polymer particle is elongated.

13. The method of claim 12, wherein said elongated biocompatible polymer particle has a length greater than about 0.3 millimeters.

14. The method of claim 12, wherein said elongated biocompatible polymer particle has a diameter smaller than about 100 microns.

15. The method of claim 12, wherein said elongated biocompatible polymer particle has a hollow interior.

16. The method of claim 1, wherein said particle is substantially tubular.

17. The method of claim 1, wherein said pharmaceutical substance comprises at least one substance from the group consisting of antimicrobials, antiprotozoals, chemotherapeutic agents antineoplastics, and polypeptides.

18. The method of claim 17, wherein said pharmaceutical substance is selected from the group consisting of imipramine, insulin, pentamidine and streptomycin.

19. The method of claim 1, wherein said biocompatible polymer comprises a biodegradable polymer.

20. The method of claim 1, wherein said solvent comprises at least one solvent selected from the group consisting of methylene chloride, trichloromethane and ethyl acetate.

21. The method of claim 1, wherein said biocompatible polymer particle comprises less than about 50 parts per million by weight of said solvent.

22. The method of claim 21, wherein said biocompatible polymer particle comprises less than about 10 parts per million by weight of said solvent.

23. A biocompatible polymer particle for sustained release of a pharmaceutical substance, wherein said particle comprises a substantially amorphous biocompatible polymer having a crystallinity of no more than about 25%, wherein said pharmaceutical substance is combined with an amphiphilic material to form a hydrophobic ion paired complex; wherein said biocompatible polymer comprises at least one polymer selected from the group consisting of poly(L-lactic) acid, poly(D-lactic) acid, polyglycolic acid, polyanhydride, polycarboxyphenoxyhexane, polybutyrate, and cellulose; wherein said amphiphilic material is selected from the group consisting of sodium dodecyl sulfate, bis-(2-ethylhexyl) sodium sulfosuccinate, cholesterol sulfate and sodium laurate; wherein said particle comprises a substantially homogeneous mixture of said pharmaceutical substance and said amorphous biocompatible polymer; wherein the weight percentage of said hydrophobic ion paired complex to the total weight of said hydrophobic ion paired complex and said biocompatible polymer is in the range of about 15% to 70%.

24. The biocompatible polymer particle of claim 23, wherein said particle is suspended in a liquid solvent.

25. The biocompatible polymer particle of claim 24, wherein said liquid solvent is selected from the group consisting of aqueous solvents and organic solvents.

26. The biocompatible polymer particle of claim 25, wherein said liquid solvent comprises at least one solvent selected from the group consisting of ethanol and propylene glycol.

27. A plurality of biocompatible polymer particles of claim 23, wherein at least about 90% by weight of said particles are smaller than about 10 microns.

28. A plurality of biocompatible polymer particles of claim 23, wherein at least about 90% by weight of said particles are smaller than about 6 microns.

29. A plurality of biocompatible polymer particles of claim 23, wherein at least about 90% by weight of said particles are smaller than about 1 micron.

30. The particle of claim 23, said particle is substantially spheroidal.

31. The particle of claim 23, wherein said particle is elongated.

32. The elongated particle of claim 31, wherein said elongated particle has a length greater than about 0.3 millimeters.

33. The elongated particle of claim 32, wherein said elongated particle has a diameter smaller than about 100 microns.

34. The elongated particle of claim 31, wherein said elongated particle has a hollow interior.

35. The particle of claim 31, wherein said particle is substantially tubular.

36. The particle of claim 23, wherein said pharmaceutical substance comprises at least one substance selected from the group consisting of antibiotic agents, chemotherapeutic agents, and biologic agents.

37. The particle of claim 36, said pharmaceutical substance is selected from the group consisting of isoniazid, imipramine, insulin, pentamidine and streptomycin.

38. The particle of claim 23, wherein said biocompatible polymer comprises a biodegradable polymer.

39. A method for making a composition for sustained release of a pharmaceutical substance, wherein said method comprises providing a plurality of particles of claim 23, and a means of agglomerating said particles, and forming said composition using said particles and said means, wherein said composition comprises an agglomerate of said particles.

40. The method of claim 39, said agglomerate is selected from the group consisting of cylinders, beads, pellets, discs, and combinations thereof.

41. The method of claim 39, said agglomerate has a mass of from about 0.01 grams to about 100 grams.

42. The method of claim 41, wherein said agglomerate has a mass of from about 0.5 grams to about 10 grams.

43. The method of claim 39, said agglomerate has a volume of from about 0.01 cubic centimeters to about 100 cubic centimeters.

44. The method of claim 39, said agglomerating step comprises compression agglomeration.

45. A method for sustained release of a pharmaceutical substance in a subject wherein said method comprises providing a biocompatible polymer particle of claim 23, and administering said biocompatible polymer particle to said subject.

46. The method of claim 45, wherein said biocompatible polymer particle is administered to said subject via a mode of administration selected from the group consisting of subcutaneous administration, intraperitoneal administration, intraocular administration, inhalation, injection and oral administration.

47. The method of claim 46, said subject is selected from the group consisting of human and non-human animals.

48. The method of claim 46, wherein said particle is suspended in a liquid solvent.

* * * * *

UNITED STATES PATENT AND TRADEMARK OFFICE
CERTIFICATE OF CORRECTION

PATENT NO. : 6,613,358 B2
DATED : September 2, 2003
INVENTOR(S) : Randolph et al.

It is certified that error appears in the above-identified patent and that said Letters Patent is hereby corrected as shown below:

<u>Title page,</u>
Item [60], Related U.S. Application Data, please delete "application No. 60/166,230, filed on Nov. 18, 1999, and provisional" such that item [60] reads as follows:
-- Provisional application No. 60/078,390, filed on Mar. 18, 1998. --

Signed and Sealed this

Second Day of March, 2004

JON W. DUDAS
*Acting Director of the United States Patent and Trademark Office*